US012077778B2

(12) United States Patent
Koehler et al.

(10) Patent No.: US 12,077,778 B2
(45) Date of Patent: Sep. 3, 2024

(54) METHODS OF GENERATING HUMAN INNER EAR SENSORY EPITHELIA AND SENSORY NEURONS

(71) Applicant: INDIANA UNIVERSITY RESEARCH AND TECHNOLOGY CORPORATION, Indianapolis, IN (US)

(72) Inventors: Karl R. Koehler, Indianapolis, IN (US); Eri Hashino, Indianapolis, IN (US)

(73) Assignee: INDIANA UNIVERSITY RESEARCH AND TECHNOLOGY CORPORATION, Bloomington, IN (US)

(*) Notice: Subject to any disclaimer, the term of this patent is extended or adjusted under 35 U.S.C. 154(b) by 505 days.

(21) Appl. No.: 16/989,554

(22) Filed: Aug. 10, 2020

(65) Prior Publication Data

US 2020/0370007 A1 Nov. 26, 2020

Related U.S. Application Data

(62) Division of application No. 15/769,254, filed as application No. PCT/US2016/058121 on Oct. 21, 2016, now abandoned.

(Continued)

(51) Int. Cl.
*C12N 5/0793* (2010.01)
*C12N 5/0735* (2010.01)
*C12N 5/074* (2010.01)

(52) U.S. Cl.
CPC ........... *C12N 5/062* (2013.01); *C12N 5/0606* (2013.01); *C12N 5/0607* (2013.01);
(Continued)

(58) Field of Classification Search
CPC .............. C12N 5/062; C12N 5/0606; C12N 2533/90; C12N 2501/415; C12N 2501/115;
(Continued)

(56) References Cited

U.S. PATENT DOCUMENTS 8,642,339 B2  2/2014  Sato et al.
9,624,468 B2  4/2017  Hashino et al.
(Continued)

FOREIGN PATENT DOCUMENTS

CN  102317442 A  7/2010
CN  102186969 A  9/2011
(Continued)

OTHER PUBLICATIONS

L.M. Shaw. Tumor Cell Invasion Assays. Methods in Molecular Biology (2005), v294, 97-105. (Year: 2005).*
(Continued)

*Primary Examiner* — Sean C. Barron
(74) *Attorney, Agent, or Firm* — Quarles & Brady, LLP

(57) ABSTRACT

Provided herein are methods for directing differentiation of human pluripotent stem cells into inner ear sensory epithelia and sensory neurons. More particularly, provided herein are methods for obtaining three-dimensional cultures comprising human pluripotent stem cell-derived pre-otic epithelium, otic vesicles, and inner ear sensory epithelia containing hair cells, sensory neurons, and supporting cells.

20 Claims, 37 Drawing Sheets

Specification includes a Sequence Listing.

Related U.S. Application Data

(60) Provisional application No. 62/244,568, filed on Oct. 21, 2015.

(52) U.S. Cl.
CPC .... *C12N 2501/115* (2013.01); *C12N 2501/15* (2013.01); *C12N 2501/155* (2013.01); *C12N 2501/415* (2013.01); *C12N 2506/02* (2013.01); *C12N 2533/52* (2013.01); *C12N 2533/90* (2013.01)

(58) Field of Classification Search
CPC .......... C12N 2501/155; C12N 2501/15; C12N 5/0607; C12N 2506/02; C12N 2533/52
See application file for complete search history.

(56) References Cited

U.S. PATENT DOCUMENTS

| | | | |
|---|---|---|---|
| 10,308,911 | B2 | 6/2019 | Hashino et al. |
| 11,021,688 | B2 | 6/2021 | Koehler et al. |
| 2006/0024278 | A1* | 2/2006 | Chen .................. A01K 67/0276 514/44 A |
| 2006/0035375 | A1 | 2/2006 | Head |
| 2008/0139469 | A1 | 6/2008 | Imamura |
| 2008/0171385 | A1 | 7/2008 | Bergendahl |
| 2009/0098093 | A1 | 4/2009 | Edge |
| 2009/0124568 | A1 | 5/2009 | Heller |
| 2009/0317441 | A1 | 12/2009 | Bilbo et al. |
| 2011/0097799 | A1 | 4/2011 | Stankewicz et al. |
| 2011/0165130 | A1 | 7/2011 | Guenou |
| 2011/0321180 | A1 | 12/2011 | Lee |
| 2012/0028351 | A1 | 2/2012 | Li |
| 2012/0148541 | A1 | 6/2012 | Lee et al. |
| 2014/0004556 | A1 | 1/2014 | Heller |
| 2015/0125953 | A1 | 5/2015 | Hashino et al. |
| 2016/0213717 | A1 | 7/2016 | Xu |
| 2017/0240858 | A1 | 8/2017 | Hashino et al. |
| 2018/0305671 | A1 | 10/2018 | Koehler et al. |
| 2021/0102177 | A1 | 4/2021 | Koehler et al. |

FOREIGN PATENT DOCUMENTS

| | | |
|---|---|---|
| CN | 103785064 A | 5/2014 |
| JP | 2004159471 | 6/2004 |
| JP | 2006-083082 A | 3/2006 |
| JP | 2009-512423 | 3/2007 |
| WO | 03/051419 A1 | 6/2003 |
| WO | 2008094597 | 8/2008 |
| WO | 2007033215 | 3/2009 |
| WO | 2009156398 A1 | 12/2009 |
| WO | 2010011352 A2 | 1/2010 |
| WO | 2010077955 | 7/2010 |
| WO | 2010096496 A1 | 8/2010 |
| WO | 2011149762 A2 | 12/2011 |
| WO | 2013166488 | 11/2013 |
| WO | 2015134652 | 9/2015 |
| WO | 2017070506 A1 | 4/2017 |

OTHER PUBLICATIONS

McCarty et al. The Hydraulic Conductivity of Matrigel(TM). Biorheology (2007), 44(5-6), 18 page reprint. (Year: 2007).*
Scheffer et al. Gene Expression by Mouse Inner Ear Hair Cells during Development. J Neurosci (Apr. 2015), 35(16), 6366-6380. (Year: 2015).*
Sekerková et al. Espins and the actin cytoskeleton of hair cell stereocilia and sensory cell microvilli. Cell. Mol. Life Sci. (2006), 63, 2329-2341. (Year: 2006).*
Avinash et al. 3-D analysis of F-actin in stereocilia of cochlear hair cell after loud noise exposure. Hearing Research (1993), 67, 139-146. (Year: 1993).*
Yu, J, et al. "Induced pluripotent stem cell lines derived from human somatic cells." science 318.5858 (2007): 1917-1920.
China National Intellectual Proprty Administration, First Office Action and Search Report, Application No. 201680061915.0, Apr. 26, 2021, 18 pages.
European Patent Office, Examination Report, Application No. 16858294.8, Mar. 23, 2020, 6 pages.
European Patent Office, Examination Report, Application No. 16858294.8, Jun. 2, 2021, 6 pages.
Japan Patent Office, Notice of Reasons for Rejection, Application No. 2018-520429, Jun. 8, 2021, 7 pages.
Beers, J. et al. Passaging and colony expansion of human pluripotent stem cells by enzymefree dissociation in chemically defined culture conditions. Nature Protocols 7, 2029-2040 (2012).
Burns, J. C., et al. Single-cell RNA-Seq resolves cellular complexity in sensory organs from the neonatal inner ear. Nature Communications 6, 8557 (2015).
Chambers, S. M. et al. Combined small-molecule inhibition accelerates developmental timing and converts human pluripotent stem cells into nociceptors. Nature Biotechnology 30, 715-720 (2012).
Chen, G., et al. "Chemically defined conditions for human iPSC derivation and culture." Nature methods 8.5 (2011): 424.
Chen, J.-R. et al. Effects of genetic correction on the differentiation of hair cell-like cells from iPSCs with MYO15A mutation. Cell Death & Differentiation (2016). doi:10.1038/cdd.2016.16.
Chen, W. et al. Restoration of auditory evoked responses by human ES-cell-derived otic progenitors. Nature 490, 278-282 (2012).
Dejonge, RE., et al. "Modulation of Wnt signaling enhances inner ear organoid development in 3D culture." PloS one 11.9 (2016): e0162508.
Ealy, M., et al. Single-cell analysis delineates a trajectory toward the human early otic lineage. PNAS 201605537 (2016). doi:10.1073/pnas.1605537113.
Ebert, AD., et al. "Induced pluripotent stem cells from a spinal muscular atrophy patient." Nature 457.7227 (2009): 277.
European Patent Office, European Search Report for application 16858294.8, dated Feb. 20, 2019, 12 pages.
Géléoc, G. S. G. et al. Sound strategies for hearing restoration. Science 344, 1241062 (2014).
Géléoc, G. S. G., et al. Developmental acquisition of voltage-dependent conductances and sensory signaling in hair cells of the embryonic mouse inner ear. The Journal of neuroscience : the official journal of the Society for Neuroscience 24, 11148-11159 (2004).
Groves, A. K. et al. Shaping sound in space: the regulation of inner ear patterning. Development 139, 245-257 (2012).
Hama, H. et al. ScaleS: an optical clearing palette for biological imaging. Nature Neuroscience 18, 1518-1529 (2015).
Hannan, N. R. F., et al. Production of hepatocyte-like cells from human pluripotent stem cells. Nature Protocols 8, 430-437 (2013).
Hartman, B. H., et al. Identification and characterization of mouse otic sensory lineage genes. Frontiers in cellular neuroscience 9, 79 (2015).
Howden, Sara E., et al. "Genetic correction and analysis of induced pluripotent stem cells from a patient with gyrate atrophy." Proceedings of the National Academy of Sciences 108.16 (2011): 6537-6542.
Huch, M., et al. (2015). Modeling mouse and human development using organoid cultures. Development, 142(18), 3113-3125. http://doi.org/10.1242/dev.118570.
International Search Report and Written Opinion for international application No. PCT/US2016/058121 dated Jan. 25, 2017, 9 pages.
Japan Patent Office. Office Action for application 2018-520429. Mailed on Oct. 6, 2020. With translation.
Kirby, L. A., et al. "Glycogen synthase kinase 3 (GSK3) inhibitor, SB-216763, promotes pluripotency in mouse embryonic stem cells." PloS one 7.6 (2012): e39329.
Koehler, K. R. et al. 3D mouse embryonic stem cell culture for generating inner ear organoids. Nature Protocols 9, 1229-1244 (2014).
Koehler, K. R., et al. Generation of inner ear sensory epithelia from pluripotent stem cells in 3D culture. Nature 500, 217-221 (2013).

(56) References Cited

OTHER PUBLICATIONS

Kwon, H.-J., et al. Identification of early requirements for preplacodal ectoderm and sensory organ development. PLoS genetics 6, e1001133 (2010).

Ladher, R. K., et al. From shared lineage to distinct functions: the development of the inner ear and epibranchial placodes. Development 137, 1777-1785 (2010).

Lancaster, M. A. et al. Cerebral organoids model human brain development and microcephaly. Nature 501, 373-379 (2013).

Leung, A. W., et al. Differential BMP signaling controls formation and differentiation of multipotent preplacodal ectoderm progenitors from human embryonic stem cells. Developmental biology 379, 208-220 (2013).

Lim, R. et al. Anatomical and physiological development of the human inner ear. Hearing research (2016). doi:10.1016/j.heares.2016.02.004.

Liu, X.-P., et al. Functional development of mechanosensitive hair cells in stem cell-derived organoids parallels native vestibular hair cells. Nature Communications 7, 11508 (2016).

Ludwig T, et al., "Derivation of human embryonic stem cells in defined conditions," Nat. Biotechnol. 24:185-187 (2006).

Ludwig T, et al., "Feeder-independent culture of human embryonic stem cells," Nat. Methods 3:637-646 (2006).

Maruyama, T. et al. Increasing the efficiency of precise genome editing with CRISPR-Cas9 by inhibition of nonhomologous end joining. Nature Biotechnology 33, 538-542 (2015).

McCracken, K. W. et al. Modelling human development and disease in pluripotent stemcell-derived gastric organoids. Nature (2014). doi:10.1038/nature13863.

Müller, U. et al. New treatment options for hearing loss. Nat Rev Drug Discov 14, 346-365 (2015).

Nasu, M. et al. Robust Formation and Maintenance of Continuous Stratified Cortical Neuroepithelium by Laminin- Containing Matrix in Mouse ES Cell Culture. PLoS One 7, e53024 (2012).

Ohnishi, H. et al. Limited hair cell induction from human induced pluripotent stem cells using a simple stepwise method. Neuroscience Letters 599, 49-54 (2015).

Ohyama, T., et al. Wnt signals mediate a fate decision between otic placode and epidermis. Development 133, 865- 875 (2006).

Ran, F. A. et al. Genome engineering using the CRISPR-Cas9 system. Nature Protocols 8, 2281-2308 (2013).

Roberts, R. M. et al. Differentiation of trophoblast cells from human embryonic stem cells: to be or not to be? Reproduction 147, D1-12 (2014).

Rodulfo, K. (Sep. 20, 2016). Whoa: L'Oreal is Working on 3-D Printing Hair. Retrieved from https://www.elle.com/beauty/hair/news/a39699/lorea-poietis-3d-printing-hair/ on Sep. 12, 2019.

Ronaghi, M. et al. Inner Ear Hair Cell-Like Cells from Human Embryonic Stem Cells. Stem Cells and Development 23, 1275-1284 (2014).

Sato, T., et al. (2009). Single Lgr5 stem cells build crypt-villus structures in vitro without a mesenchymal niche. Nature, 459(7244), 262-265. http://doi.org/10.1038/nature07935.

Sergeyenko, Y., et al. Age-Related Cochlear Synaptopathy: An Early-Onset Contributor to Auditory Functional Decline. 33, 13686-13694 (2013).

Shi, F., et al. (2012). Wnt-responsive Lgr5-expressing stem cells are hair cell progenitors in the cochlea., 32(28), 9639-9648. http://doi.org/10.1523/JNEUROSCI.1064-12.2012.

Tang, Z.-H. et al. Genetic Correction of Induced Pluripotent Stem Cells From a Deaf Patient With MYO7A Mutation Results in Morphologic and Functional Recovery of the Derived Hair Cell-Like Cells. Stem Cells Transl Med 5, 561-571 (2016).

Thomson, JA., et al. "Embryonic stem cell lines derived from human blastocysts." science 282.5391 (1998): 1145-1147.

Wang, T., et al. (2015). Lgr5+ cells regenerate hair cells via proliferation and direct transdifferentiation in damaged neonatal mouse utricle. Nature Communications, 6, 6613. http://doi.org/10.1038/ncomms7613.

Watanabe K, et al., "A ROCK inhibitor permits survival of dissociated human embryonic stem cells," Nat. Biotechnol. 25:681-686 (2007).

Yin, X., et al. (2014). Niche-independent high-purity cultures of Lgr5+ intestinal stem cells and their progeny. Nature Methods, 11(1), 106-112. http://doi.org/10.1038/nmeth.2737.

Yu, J, et al. "Human induced pluripotent stem cells free of vector and transgene sequences." Science 324.5928 (2009):797-801.

China National Intellectual Property Administration, Second Office Action and Search Report, Application No. 201680061915.0, Mar. 18, 2022, 15 pages.

Yannas, I. V. et al. Design of an artificial skin. I. Basic design principles. J. Biomed. Mater. Res. 14, 65-81 (1980).

Ying, Q.-L. et al., The ground state of embryonic stem cell self-renewal. Nature 453, 519 (2008).

Yizhar, O., et al. Optogenetics in neural systems. Neuron 71, 9-34 (2011).

Yurchenco et al., Basal lamina assembly, Cell Biology, 1994, 6: pp. 674-681.

Zhang et al. Distinct functions fo BMP4 during different stages of mouse ES cell neural commitment, (Development. Jul. 2010; 137(13):2095-105.

Zhang, F. et al. Optogenetic interrogation of neural circuits: technology for probing mammalian brain structures. Stem Cells 5, 439-456 (2010).

Zheng, Y. et al. Mature hair follicles generated from dissociated cells: a universal mechanism of folliculoneogenesis. Developmental dynamics : an official publication of the American Association of Anatomists 239, 2619-2626 (2010).

Ramot, Y. et al. Advanced inhibition of undesired human hair growth by PPARγ modulation? The Journal of investigative dermatology 134, 1128-1131 (2014).

Ranga, A., et al. 3D niche microarrays for systems-level analyses of cell fate. Nature Communications. Jul. 14, 2014. 5:4324.

Ranga, A., et al. Drug discovery through stem cell-based organoid models. Adv. Drug Deliv. Rev. 69-70, 19-28 (2014).

Ranga, A., et al. Neural tube morphogenesis in synthetic 3D microenvironments. Proceedings of the National Academy of Sciences, 2016. 113(44):E6831-E6839.

Reyes, J. H. et al. Glutamatergic neuronal differentiation of mouse embryonic stem cells after transient expression of neurogenin 1 and treatment with BDNF and GDNF: in vitro and in vivo studies. J Neurosci 28, 12622-12631 (2008).

Roehm, P. C. & Hansen, M. R. Strategies to preserve or regenerate spiral ganglion neurons. Curr Opin Otolaryngol Head Neck Surg 13, 294-300 (2005).

Rusznák, Z. & Szucs, G. Spiral ganglion neurones: an overview of morphology, firing behaviour, ionic channels and function. Pflugers Arch 457, 1303-1 325 (2009).

Sandoe, J. et al. Opportunities and challenges of pluripotent stem cell neurodegenerative disease models. Nature Neuroscience 16, 780-789 (2013).

Saul, S. M. et al. Math5 expression and function in the central auditory system. Mol Cell Neurosci 37, 153-1 69 (2008).

Schlaeger, T. M. et al. A comparison of non-integrating reprogramming methods. Nature Biotechnology (2014). doi:10.1038/nbt.3070.

Schlosser, E., Induction and specification of cranial placodes, Development Biology 294:303-351 (2006).

Schneider, M. R., et al. The hair follicle as a dynamic miniorgan. Current biology : CB 19, R132-42 (2009).

Sebastiano, V. et al. Human COL7A1-corrected induced pluripotent stem cells for the treatment of recessive dystrophic epidermolysis bullosa. Science translational medicine 6, 264ra163-264ra163 (2014).

Shi, F., et al. BMP4 induction of sensory neurons from human embryonic stem cells and reinnervation of sensory epithelium. EurJ Neurosci 26, 3016-3023 (2007).

Soldner, F. et al. Parkinson's disease patient-derived induced pluripotent stem cells free of viral reprogramming factors. Cell 136, 964-977 (2009).

Soma, T., et al. Hair-inducing ability of human dermal papilla cells cultured under Wnt/β-catenin signalling activation. Experimental Dermatology 21, 307-309 (2012).

(56) References Cited

OTHER PUBLICATIONS

Soma, T., et al. Involvement of transforming growth factor-beta2 in catagen induction during the human hair cycle. Journal of Investigative Dermatology 118, 993-997 (2002).
Spoendlin, H. Retrograde degeneration of the cochlear nerve. Acta Otolanyngol, 79, 266-275 (1975).
Stenn, K. S. et al. Controls of hair follicle cycling. Physiological reviews 81, 449-494 (2001).
St-Jacques, B. et al. Sonic hedgehog signaling is essential for hair development. Current biology : CB 8, 1058-1068 (1998).
Streit, A. The preplacodal region: an ectodermal domain with multipotential progenitors that contribute to sense organs and cranial sensory ganglia. Int J Dev Biol 51, 447-461 (2007).
Streit, A., The cranial sensory nervous system: specification of sensory progenitors and placodes (Dec. 15, 2008), StemBook, ed. The Stem Cell Research Community, StemBook, doi/10.3824/stembook.1.31.1, http://stembook.org.
Suga, H. et al. Self-formation of functional adenohypophysis in three-dimensional culture. Nature 480(7375), 57-62 (2011).
Sun, B. K., et al. Advances in skin grafting and treatment of cutaneous wounds. Science 346, 941-945 (2014).
Takagi, R. et al. Bioengineering a 3D integumentary organ system from iPS cells using an in vivo transplantation model. Science Advances 2, e1500887-e1500887 (2016).
Takasato, M. et al. Kidney organoids from human iPS cells contain multiple lineages and model human nephrogenesis. Nature 526, 564-568 (2015).
Thonabulsombat, C., et al. Implanted embryonic sensory neurons project axons toward adult auditory brainstem neurons in roller drum and Stoppini co-cultures. Brain Res 1170, 48-58 (2007).
Tsarovina, K. et al. The Gata3 transcription factor is required for the survival of embryonic and adult sympathetic neurons. Journal of Neuroscience 30, 10833-10843 (2010).
Tsuji, Y. et al. A potential suppressor of TGF-beta delays catagen progression in hair follicles. J. Investig. Dermatol. Symp. Proc. 8, 65-68 (2003).
Umegaki-Arao, N. et al. Induced pluripotent stem cells from human revertant keratinocytes for the treatment of epidermolysis bullosa. Science translational medicine 6, 264ra164 (2014).
Volkner, M. et al. Retinal Organoids from Pluripotent Stem Cells Efficiently Recapitulate Retinogenesis. Stem Cell Reports 6, 525-538 (2016).
Vukicevic, S., et al. "Identification of multiple active growth factors in basement membrane matrigel suggests caution in interpretation of cellular activity related to extracellular matrix components." Experimental Cell Research (1992) 202,1-8.
Warchol, M.E., Richardson, G.P., Expression of the Pax2 transcription factor is associated with vestibular phenotype in the avian inner ear. Dev Neurobiol 69, 191-202 (2009).
Watanabe, K. et al. Directed differentiation of telencephalic precursors from embryonic stem cells. Nat Neurosci vol. 8, No. 3, 288-296 (Mar. 2005).
Wataya et al., (2008), Proc. Natl. Acad. Sci. USA, 105(33): 11796-11801.
Watt, F. and Hogan BM, Out of Eden: Stem cells and their niches, Science, 287: 1427-1430 (2000).
Watt, F. M. Mammalian skin cell biology: at the interface between laboratory and clinic. Science 346, 937-940 (2014).
Wei, D. et al. Cells of adult brain germinal zone have properties akin to hair cells and can be used to replace inner ear sensory cells after damage. Proc Natl Acad Sci USA 105, 21000-21005 (2008).
Weick, J. P. et al. Functional control of transplantable human ESC-derived neurons via optogenetic targeting. Stem Cells 28, 2008-2016 (2010).
Weick, J. P., et al. Human embryonic stem cell-derived neurons adopt and regulate the activity of an established neural network. Proc Natl Acad Sci USA 108, 20189-20194 (2011).
Wenzel, D. et al. Genetically corrected iPSCs as cell therapy for recessive dystrophic epidermolysis bullosa. Science translational medicine 6, 264ra165 (2014).
Wiley et al., cGMP production fo patient-specific iPSCs and photoreceptor precursor cells to treate retinal degenerative blindness, Scientific Reports, 6:30742, Jul. 29, 2016. pp. 1-16.
Wilson, P. A. & Hemmati-Brivanlou, A. Induction of epidermis and inhibition of neural fate by Bmp-4. Nature 376, 331-333 (1995).
Wilson, P. A., et al. Concentration-dependent patterning of the Xenopus ectoderm by BMP4 and its signal transducer Smadi. Development 124, 3177-3184 (1997).
Wright, M. C., et al. (2015). Unipotent, Atoh1+ progenitors maintain the Merkel cell population in embryonic and adult mice. The Journal of Cell Biology, 208(3), 367-379.
Wu, X., et al. Full-thickness skin with mature hair follicles generated from tissue culture expanded human cells. Tissue Eng Part A 20, 3314-3321 (2014).
Xia et al., Concise review: a high-content screening approach to stem cell research and drug discovery. (2012) Stem Cells, 30(9): 1800-1807.
Xing, L. et al. Alopecia areata is driven by cytotoxic T lymphocytes and is reversed by JAK inhibition. Nature medicine 20, 1043-1049 (2014).
Yamanaka, S. Induced Pluripotent Stem Cells: Past, Present, and Future. Cell Stem Cell 10, 678-684 (2012).
Yang, R. et al. Generation of folliculogenic human epithelial stem cells from induced pluripotent stem cells : Nature Communications : Nature Publishing Group. Nature Communications 5, 3071 (2014).
Aberdam, D. et al. Key role of p63 in BMP-4-induced epidermal commitment of embryonic stem cells. Cell Cycle 6, 291-294 (2007).
Aberdam, E. et al. A pure population of ectodermal cells derived from human embryonic stem cells. Stem Cells 26, 440-444 (2008).
Aburto, M. R., et al. AKT signaling mediates IGF-I survival actions on otic neural progenitors. PLoS One 7, e30790 (2012).
Adamson, C. L., et al. Firing features and potassium channel content of murine spiral ganglion neurons vary with cochlear location. J Comp Neurol 447, 331-350 (2002).
Ahrens, K. & Schiosser, G. Tissues and signals involved in the induction of placodal Six1 expression in Xenopus laevis. Dev Biol 288, 40-59 (2005).
Appler, J. M. & Goodrich, L. V. Connecting the ear to the brain: Molecular mechanisms of auditory circuit assembly. Prog Neurobiol 93, 488-508 (2011).
Bailey, A.P., Bhattacharyya, S., Bronner-Fraser, M. & Streit, A. Lens specification is the ground state of all sensory placodes, from which FGF promotes olfactory identity. Dev Cell 11, 505-517 (2006).
Beisel, K., et al. Regenerating cochlear hair cells: quo vadis stem cell. Cell Tissue Res. 333, 373-379 (2008).
Bell, E., et al. Living tissue formed in vitro and accepted as skin-equivalent tissue of full thickness. Science 211, 1052-1054 (1981).
Bermingham-McDonogh, O. & Reh, T.A., Regulated Reprogramming in the Regneration of Sensory Receptor Cells. Neuron 71, 389-405 (2011).
Bernardo, A. S. et al. Brachyury and CDX2 mediate BMP-induced differentiation of human and mouse pluripotent stem cells into embryonic and extraembryonic lineages. Cell Stem Cell 9, 144-155 (2011).
Bhattacharyya, S. & Bronner-Fraser, M. Competence, specification and commitment to an olfactory placode fate. Development 135, 4165-4177 (2008).
Blanpain, C. et al. Stem cell plasticity. Plasticity of epithelial stem cells in tissue regeneration. Science 344, 1242281-1242281 (2014).
Bodó, E. et al. Dissecting the impact of chemotherapy on the human hair follicle: a pragmatic in vitro assay for studying the pathogenesis and potential management of hair follicle dystrophy. The American journal of pathology 171, 1153-1167 (2007).
Brigande, J. V. & Heller, S. Quo vadis, hair cell regeneration? Nat Neurosci 12, 679-685 (2009).
Brohem et al., Artificial Skin in Perspective: Concepts and Applications, Feb. 2011, vol. 24 No. 1, pp. 1-25, 25 pages.
Chambers, S. M. et al. Highly efficient neural conversion of human ES and iPS cells by dual inhibition of SMAD signaling. Nat Biotechnol 27, 275 (2009).

(56) References Cited

OTHER PUBLICATIONS

Chapman, S., et al. Human keratinocytes are efficiently immortalized by a Rho kinase inhibitor. The Journal of clinical investigation 120, 2619-2626 (2010).
Chittur et al., Inhibition of Inflammatory Gene Expression in Keratinocytes Using a Composition Containing Carnitine, Thioctic Acid and Saw Plametto Extract, Evidence Based Complementary Alternative Medicine, Jun. 8, 2011, 7 pages.
Chuong, C.-M., et al. Defining hair follicles in the age of stem cell bioengineering. The Journal of investigative dermatology 127, 2098-2100 (2007).
Coate, T.M. et al., Otic Mesenchyme Cells Regulate Spiral Ganglion Axon Fasciculation through a Pou3f4/EphA4 Signaling Pathway. Neuron 73, 49-63 (2012).
Colombe, L., et al. Prostaglandin metabolism in human hair follicle. Experimental Dermatology 16, 762-769 (2007).
Coraux, C. et al. Reconstituted skin from murine embryonic stem cells. Current biology : CB 13, 849-853 (2003).
Corrales, C. E. et al., Engraftment and differentiation of embryonic stem cell-derived neural progenitor cells in the cochlear nerve trunk: growth of processes into the organ of Corti. J Neurobiol 66, 1489-1500 (2006).
Crawford, T. Q. & Roelink, H. The notch response inhibitor DAPT enhances neuronal differentiation in embryonic stem cell-derived embryoid bodies independently of sonic hedgehog signaling. Dev Dyn 236, 886-892 (2007).
Daudet, N., et al. Notch signalling is needed to maintain, but not to initiate, the formation of prosensory patches in the chick inner ear. Development 134, 2369-2378 (2007).
Delmaghani, S. et al. Mutations in the gene encoding pejvakin, a newly identified protein of the afferent auditory pathway, cause DFNB59 auditory neuropathy. Nat Genet 38, 770-778 (2006).
Derycke, L. D. M. & Bracke, M. E. N-cadherin in the spotlight of cell-cell adhesion, differentiation, embryogenesis, invasion and signalling. Int J Dev Biol 48, 463-476 (2004).
Desai, S.S., et al. Comparative morphology of rodent vestibular periphery. I. Saccular and utricular maculae. J Neurophysiol 93, 251-266 (2005).
Driskell, R. R. et al. Distinct fibroblast lineages determine dermal architecture in skin development and repair. Nature 504, 277-281 (2013).
Driskell, R. R., et al. "Understanding fibroblast heterogeneity in the skin." Trends in cell biology 25.2 (2015): 92-99.
Driskell, R. R., et al. Defining dermal adipose tissue. Experimental Dermatology 23, 629-631 (2014).
Eiraku, M. & Sasai, Y. Mouse embryonic stem cell culture for generation of three-dimensional retinal and cortical tissues. Nat Protocol 7, 69-79 (2012).
Eiraku, M. et al. Self-organized formation of polarized cortical tissues from ESCs and its active manipulation by extrinsic signals. Cell Stem Cell 3, 519-532 (2008).
Eiraku, M. et al. Self-organizing optic-cup morphogenesis in three-dimensional culture. Nature 472, 51-56 (2011).
Eiraku, M., et al. Relaxation-expansion model for self-driven retinal morphogenesis. Bioessays34, 17-25 (2011).
European Patent Office, European Search Report for application 16858318, mailed on Feb. 25, 2019, 12 pages.
Fujiwara et al., Regulation of Mesodermal Differentiation of Mouse Embryonic Stem Cells by Basement Membranes, The Journal of Biological Chemistry, vol. 282, No. 40, pp. 29701-29711, Oct. 5, 2007.
Gaboyard et al., Three-dimensional culture of newborn rat utricle using an extracellular matrix promotes formation of a cyst. (2005) Neuroscience 133(1):253-65.
Gale, J.E., et al. FM1-43 dye behaves as a permeant blocker of the hair-cell mechanotransducer channel. Journal of Neuroscience 21, 7013-7025 (2001).
Gilhar, A., et al. Alopecia areata. N. Engl. J. Med. 366, 1515-1525 (2012).
Gjorevski, N., et al. "Designer matrices for intestinal stem cell and organoid culture." Nature. Nov. 16, 2016. 539, 560-564.
Glavaski-Joksimovic, A. et al., Morphological differentiation of tau-green fluorescent protein embryonic stem cells into neurons after co-culture with auditory brain stem slices. Neuroscience 162, 472-48 1 (2009).
Gledhill, K., et al. (2015) "Melanin transfer in human 3D skin equivalents generated exclusively from induced pluripotent stem cells." PloS one 10(8):e0136713. doi:10.1371/journal.pone.0136713.
Gnedeva, K. et al. (2015) "Derivation of hair-inducing cell from human pluripotent stem cells", PloS One 10(1):e0116892. doi:10.1371/journal.pone.0116892.
Green, H., et al. Marker succession during the development of keratinocytes from cultured human embryonic stem cells.PNAS, 100, 15625-15630 (2003).
Grocott, T., et al. The peripheral sensory nervous system in the vertebrate head: A gene regulatory perspective. Dev Biol 370, 3-23 (2012).
Groves, A. K. & Bronner-Fraser, M. Competence, specification and commitment in otic placode induction. Development 127, 3489-3499 (2000).
Guenou, H. et al. Human embryonic stem-cell derivatives for full reconstruction of the pluristratified epidermis: a preclinical study. Lancet 374, 1745-1753 (2009).
Gunaydin, L. A. et al. Ultrafast optogenetic control. Nat Neurosci 13, 387-392 (2010).
Li, H., et al. Generation of hair cells by stepwise differentiation of embryonic stem cells. Proc Natl Acad Sci USA 100, 13495-13500 (2003).
Li, L., et al. The Three-Dimensional Human Skin Reconstruct Model: a Tool to Study Normal Skin and Melanoma Progression. J Vis Exp e2937-e2937 (2011). doi:10.3791/2937.
Li, W. & Ding, S. Small molecules that modulate embryonic stem cell fate and somatic cell reprogramming. Trends Pharmacol Sd 31, 36-45 (2010).
Liakath-Ali, K. et al. Novel skin phenotypes revealed by a genome-wide mouse reverse genetic screen. Nature Communications 5, 3540 (2014).
Litsiou, A., et al. A balance of FGF, BMP and WNT signalling positions the future placode territory in the head. Development 132, 4051-4062 (2005).
Liu et al., Gene targeting in human pluripotent stem cells. (2011) Methods Mol Biol., 767:355-367.
Lu, B., et al. "Long-term safety and function of RPE from human embryonic stem cells in preclinical models of macular degeneration." Stem cells 27.9 (2009): 2126-2135.
Lu, C. C., et al. Developmental profiling of spiral ganglion neurons reveals insights into auditory circuit assembly. J Neurosci 31, 10903-10918 (2011).
Lu, C. et al. Sweat gland progenitors in development, homeostasis, and wound repair. Cold Spring Harb Perspect Med 4, a015222 (2014).
Lysakowski, A. et al., Molecular microdomains in a sensory terminal, the vestibular calyx ending. Journal of Neuroscience 31, 10101-10114 (2011).
Margulis et al., In Vitro Fabrication of Engineered Human Skin, Methods in Molecular Biology, 289:61-70 (2005).
Martin, K. & Groves, A. K. Competence of cranial ectoderm to respond to Fgf signaling suggests a two-step model of otic placode induction. Development 133, 877-887 (2006).
Martinez-Monedero, R., et al. Differentiation of inner ear stem cells to functional sensory neurons. Dev Neurobiol 68, 669-684 (2008).
Martinez-Monedero, R., et al. Reinnervation of hair cells by auditory neurons after selective removal of spiral ganglion neurons. J Neurobiol 66, 319-331 (2006).
Martinez-Monendero, R. & Edge, A. S. B. Stem cells for the replacement of inner ear neurons and hair cells. Int. J. Dev. Biol 51, 655-66 1 (2007).
McLarren, K. DLX5 positions the neural crest and preplacode region at the border of the neural plate. Dev Biol 259, 34-47 (2003).
Medvinsky, A. et al. On human development: lessons from stem cell systems. Development 142, 17-20 (2015).

(56) References Cited

OTHER PUBLICATIONS

Merkle, F. T. et al. Efficient CRISPR-Cas9-Mediated Generation of Knockin Human Pluripotent Stem Cells Lacking Undesired Mutations at the Targeted Locus. Cell Rep 11, 875-883 (2015).
Metallo, C. M., et al. Retinoic acid and bone morphogenetic protein signaling synergize to efficiently direct epithelial differentiation of human embryonic stem cells. Stem Cells 26, 372-380 (2008).
Meyer, J. S. et al. Optic Vesicle-like Structures Derived from Human Pluripotent Stem Cells Facilitate a Customized Approach to Retinal Disease Treatment. Stem Cells 29, 1206-1218 (2011).
Meyer, J. S. et al., Modeling early retinal development with human embryonic and induced pluripotent stem cells. Proc Natl Acad Sci USA 106, 16698-1 6703 (2009).
Meyers, J.R. et al., Lighting up the senses: FM1-43 loading of sensory cells through nonselective ion channels. Journal of Neuroscience 23, 4054-4065 (2003).
Mica, Y., et al. Modeling neural crest induction, melanocyte specification, and disease-related pigmentation defects in hESCs and patient-specific iPSCs. Cell Rep 3, 1140-1152 (2013).
Miyamoto, R. T., et al. Cochlear implantation in auditory neuropathy. Adv Otorhinolaryngol, 57, 160-161 (2000).
Moore, D. R. & Shannon, R. V. Beyond cochlear implants: awakening the deafened brain. Nat Neurosci 12, 686-69 1 (2009).
Moriguchi, T. et al. MafB is essential for renal development and F4/80 expression in macrophages. Mol Cell Biol 26, 571 5-572 7 (2006).
Mort, R. L., et al. Ex vivo culture of mouse embryonic skin and live-imaging of melanoblast migration. J Vis Exp (87), e51352, doi:10.3791/51352 (2014).
Moscona, A. et al. The dissociation and aggregation of cells from organ rudiments of the early chick embryo. Journal of Anatomy 86, 287-301 (1952).
Moscona, A. Rotation-mediated histogenetic aggregation of dissociated cells. A quantifiable approach to cell interactions in vitro. Experimental cell research 22, 455-475 (1961).
Muguruma, K., et al. Self-Organization of Polarized Cerebellar Tissue in 3D Culture of Human Pluripotent Stem Cells. Cell Rep 10, 537-550 (2015).
Nakano, T. et al. Self-Formation of Optic Cups and Storable Stratified Neural Retina from Human ESCs. Cell Stem Cell 10, 771-785 (2012).
Narisawa, Y., et al. (1994). Merkel Cells of the Terminal Hair Follicle of the Adult Human Scalp. Journal of Investigative Dermatology, 102(4), 506-510.
Nose, A. & Takeichi, M. A novel cadheriri cell adhesion molecule: its expression patterns associated with implantation and organogenesis of mouse embryos. J Cell Biol 103, 2649-2658 (1986).
Odorico J, et al., Multilineage differentiation from human embryonic stem cell lines, Stem Cells 19: 193-204 (2001).
Oesterle, E.C., et al. Sox2 and Jagged1 Expression in Normal and Drug-Damaged Adult Mouse Inner Ear. J Assoc Res Otolaryngol 9, 65-89 (2007).
Oh, J. W. et al. A Guide to Studying Human Hair Follicle Cycling In Vivo. The Journal of investigative dermatology 136, 34-44 (2016).
Oh, J. W., et al. Organotypic skin culture. The Journal of investigative dermatology 133, e14 (2013).
Ohyama, T., et al. The first steps towards hearing: mechanisms of otic placode induction. Int J Dev Biol 51, 463-472 (2007).
Oshima, K. et al. Mechanosensitive Hair Cell-like Cells from Embryonic and Induced Pluripotent Stem Cells. Cell 141, 704-716 (2010).
Ouji, Y., et al. In vitro differentiation of mouse embryonic stem cells into inner ear hair cell-like cells using stromal cell conditioned medium. Cell Death Dis 3, e314 (2012).
Padanad, M. S. & Riley, B. B. Pax2/8 proteins coordinate sequential induction of otic and epibranchial placodes through differential regulation of foxi1, sox3 and fgf24. Dev Biol 351, 90-98 (2011).

Paladini, R. D., et al. Modulation of hair growth with small molecule agonists of the hedgehog signaling pathway. Journal of Investigative Dermatology 125, 638-646 (2005).
Parker, M., et al. Primary culture and plasmid electroporation of the murine organ of Corti. JoVE (2010). doi: 10.3791/1685.
Patthey, C. & Gunhaga, L. Specification and regionalisation of the neural plate border. Eur J Neurosci 34, 1516-1528 (2011).
Patthey, C., et al. Wnt-regulated temporal control of BMP exposure directs the choice between neural plate border and epidermal fate. Development 136, 73-83 (2009).
Paus, R. et al. A comprehensive guide for the recognition and classification of distinct stages of hair follicle morphogenesis. The Journal of investigative dermatology 113, 523-532 (1999).
Philpott, M. P. et al. Effects of EGF on the morphology and patterns of DNA synthesis in isolated human hair follicles. Journal of Investigative Dermatology 102, 186-191 (1994).
Philpott, M. P., et al. Human hair growth in vitro. Journal of cell science 97 ( Pt 3), 463-471 (1990).
Pieper, M., et al. Differential distribution of competence for panplacodal and neural crest induction to non-neural and neural ectoderm. Development 139, 1175-1187 (2012).
Prasain, N., et al. "Differentiation of human pluripotent stem cells to cells similar to cord-blood endothelial colony-forming cells." Nature biotechnology 32.11 (2014): 1151.
Guo et al., Building a Microphysiological Skin Model from Induced Pluripotent Stem Cells, Stem Cell Research and Therapy, Dec. 20, 2013, pp. 1-7, 7 pages.
Han, S. S. W., et al. Constructing and Deconstructing Stem Cell Models of Neurological Disease. Neuron 70, 626-644 (2011).
Hanna, J. H., et al. Pluripotency and cellular reprogramming: facts, hypotheses, unresolved issues. Cell 143, 508-525 (2010).
Hansen, D. V., et al. Deriving Excitatory Neurons of the Neocortex from Pluripotent Stem Cells. Neuron 70, 645-660 (2011).
Hardy, M. H. The development of mouse hair in vitro with some observations on pigmentation. Journal of Anatomy 83, 364-84- 3 pl (1949).
Harel, S. et al. Pharmacologic inhibition of JAK-STAT signaling promotes hair growth. Science Advances 1, e1500973-e1500973 (2015).
Harvey et al. Nresponse to BMP4 signaling during ES cell differentiation defines intermediates of the ectoderm lineage, J Cell Sci. May 15, 2010; 123(pt 10): 1796-1804.
Hideyuki et al., (2014) The Minipig—A New Tool in Stem Cell Research, Pluripotent Stem Cell Biology—Advances in Mechanisms, Methods and Models, Prof. Craig Atwood (Ed.), ISBN: 978-953-51-1590-8, InTech, DOI:10.5772/57603.
Hiler, D. et al. Quantification of Retinogenesis in 3D Cultures Reveals Epigenetic Memory and Higher Efficiency in iPSCs Derived from Rod Photoreceptors. Cell Stem Cell 17, 101-115 (2015).
Hockemeyer, D. et al. (2011) "Genetic engineering of human pluripotent cells using TALE nucleases", Nature Biotechnology 29(8): 731-734 doi: 10.1038/nbt.1927.
Honda et al., Generation of induced pluripotent stem cells in rabbits: potential experimental models for human regenerative medicine, J. Biol Chem. Oct. 8, 2010; 285(41):31362-9.
Hsu, Y.-C., et al. Emerging interactions between skin stem cells and their niches. Nature medicine 20, 847-856 (2014).
Hu, B.-Y. & Zhang, S-C. Differentiation of spinal motor neurons from pluripotent human stem cells. PNAS, 4, 1295-1 304 (2009).
Hu, Z., Corwin, J.T., Inner ear hair cells produced in vitro by a mesenchymal-to-epithelial transition, PNAS, 2007, 104(42):16675-166800.
Hu, Z., et al. Functional evaluation of a cell replacement therapy in the inner ear. Otol Neurotol 30, 55 1-558 (2009).
Hughes, J. N., et al. A novel role for gamma-secretase in the formation of primitive streak-like intermediates from ES cells in culture. Stem Cells 27, 2941-2951 (2009).
International Search Report and Written Opinion for International Application No. PCT/US2013/039686, dated Jul. 17, 2013.
International Search Report and Written Opinion for international application No. PCT/US2016/058174 dated Jan. 17, 2017, 13 pages.

(56) References Cited

OTHER PUBLICATIONS

Ito, T. et al. Interferon-gamma is a potent inducer of catagen-like changes in cultured human anagen hair follicles. Br. J. Dermatol. 152, 623-631 (2005).

Itoh, M. et al. Generation of 3D skin equivalents fully reconstituted from human induced pluripotent stem cells (iPSCs). PLoS One 8, e77673 (2013).

Itoh, M., et al. Generation of keratinocytes from normal and recessive dystrophic epidermolysis bullosa-induced pluripotent stem cells. PNAS 108, 8797-8802 (2011).

Jegalian, B.G., De Robertis, E.M., Homeotic transformations in the mouse induced by overexpression of a human Hox3.3 transgene. Cell 71, 901-910 (1992).

Jeon, S.-J., et al. Notch signaling alters sensory or neuronal cell fate specification of inner ear stem cells. J Neurosci 31, 8351-8358 (2011).

Jindo, T. et al. The effect of hepatocyte growth factor/scatter factor on human hair follicle growth. Journal of Dermatological Science 10, 229-232 (1995).

Kamiya, D. et al. Intrinsic transition of embryonic stem-cell differentiation into neural progenitors. Nature 470, 503-509 (2011).

Kandárová, H., et al. An In Vitro Skin Irritation Test (SIT) using the EpiDerm Reconstructed Human Epidermal (RHE) Model. J Vis Exp e1366-e1366 (2009). doi:10.3791/1366.

Keefer et al., Challenges and prospects for the establishment of embryonic stem cell lines of domesticated ungulates, Anim Reprod Sci. Mar. 2007; 98(1-2): 147-68.

Kleinman et al., Matrigel: Basement membrane matrix with biological activity, Seminars in Cancer Biology 15 (2005) pp. 378-386.

Kleinman, H.K., et al. "Basement membrane complexes with biological activity." Biochemistry 1986, 25, 312-318.

Kloepper, J. E. et al. Methods in hair research: how to objectively distinguish between anagen and catagen in human hair follicle organ culture. Experimental Dermatology 19, 305-312 (2010).

Kodaira, K. et al. Purification and identification of a BMP-like factor from bovine serum. Biochem Biophys Res Commun 345, 1224-1231 (2006).

Koehler et al., "Recapitulating Inner Ear Development with Pluripotent Stem Cells: Biology and Translation", In Development of Auditory and Vestibular Systems: Fourth Edition (2014) pp. 213-247, doi.org/10.1016/B978-0-12-408088-1.00008-7.

Koehler et al., Generating inner ear organoids from human pluripotent stem cells, abstract (2015).

Koehler, K. R. et al. Extended passaging increases the efficiency of neural differentiation from induced pluripotent stem cells. BMC Neurosci 12, 82 (2011).

Kondo, T. et al. Tlx3 exerts context-dependent transcriptional regulation and promotes neuronal differentiation from embryonic stem cells. Proc Natl Acad Sci USA 105, 5780-5785 (2008).

Kondo, T. et al. Wnt Signaling Promotes Neuronal Differentiation From Mesenchymal Stem Cells Through Activation of Tlx3. Stem Cells 29, 836-846 (2011).

Kopecky et al., Regeneration of Hair Cells: Making Sense of All the Noise, Pharmaceuticals, vol. 4, No. 12, (2011).

Kriks, S. et al. Dopamine neurons derived from human ES cells efficiently engraft in animal models of Parkinson's disease. Nature 480, 547-551 (2011).

Kwack, M. H., et al. Dihydrotestosterone-inducible IL-6 inhibits elongation of human hair shafts by suppressing matrix cell proliferation and promotes regression of hair follicles in mice. The Journal of investigative dermatology 132, 43-49 (2012).

Kwon, H.-J. & Riley, B. B. Mesendodermal signals required for otic induction: Bmp-antagonists cooperate with Fgf and can facilitate formation of ectopic otic tissue. Dev Dyn 238, 1582-1594 (2009).

Laine, H. et al. Cell cycle regulation in the inner ear sensory epithelia: role of cyclin D1 and cyclin-dependent kinase inhibitors. Dev Biol 337, 134-146 (2010).

Lancaster, M. A. et al. Organogenesis in a dish: modeling development and disease using organoid technologies. Science 345, 1247125 (2014).

Langan, E. A., et al. Human hair follicle organ culture: theory, application and perspectives. Experimental Dermatology 24, 903-911 (2015).

Lee, J., et al. "Hair follicle development in mouse pluripotent stem cell-derived skin organoids." Cell reports 22.1 (2018): 242-254.

Lee, L. F., et al. A simplified procedure to reconstitute hair-producing skin. Tissue Eng Part C Methods 17, 391-400 (2011).

Lee, S. H., et al. Efficient generation of midbrain and hindbrain neurons from mouse embryonic stem cells. Nat Biotechnol 18, 675-679 (2000).

Lee, Y. R., et al. Hepatocyte growth factor (HGF) activator expressed in hair follicles is involved in in vitro HGF- dependent hair follicle elongation. Journal of Dermatological Science 25, 156-163 (2001).

Lesko, M. H., et al. (2013) "Sox2 modulates the function of two distinct cell lineages in mouse skin", Developmental biology 382, pp. 15-26, doi:10.1016/j.ydbio.2013.08.004.

Li, A., et al. Architecture of the mouse utricle: macular organization and hair bundle heights. J Neurophysiol 99, 718-733 (2008).

Li, H. et al. Differentiation of neurons from neural precursors generated in floating spheres from embryonic stem cells. BMC Neurosci 10, 122 (2009).

\* cited by examiner

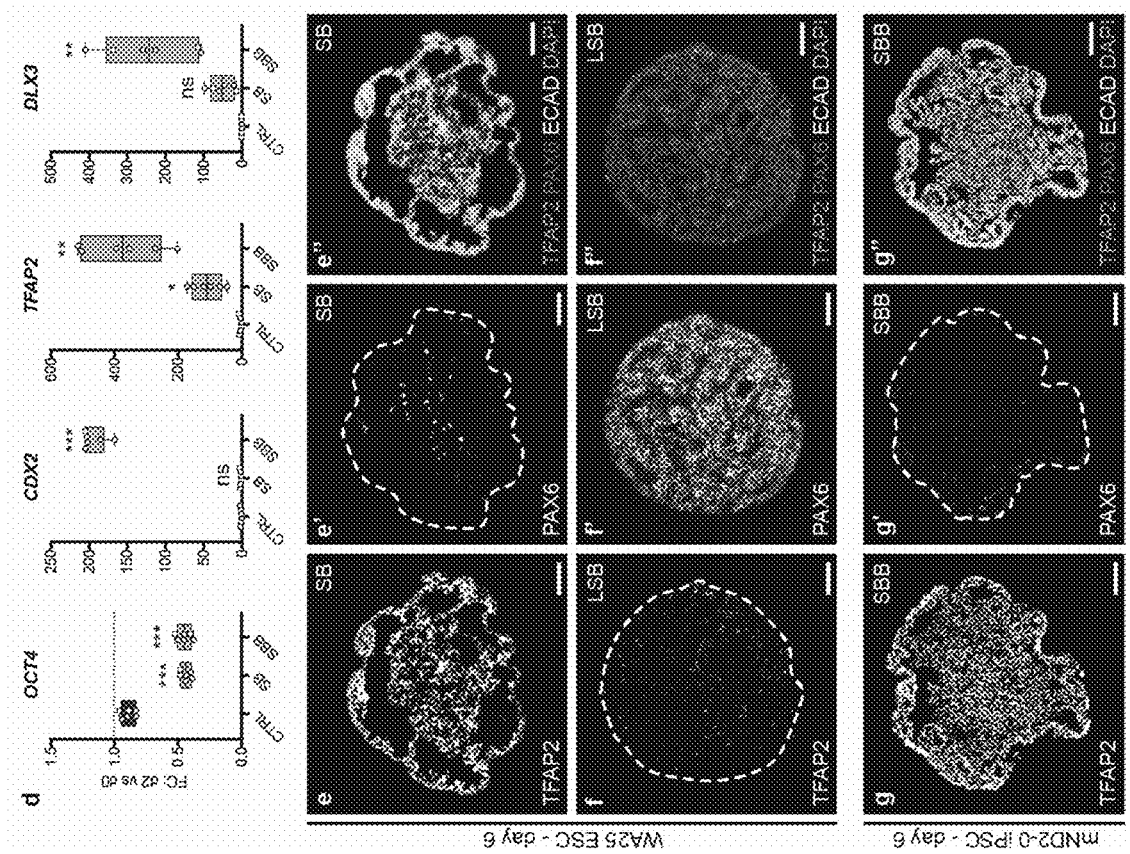
FIGS. 1A-1N, CONTINUED

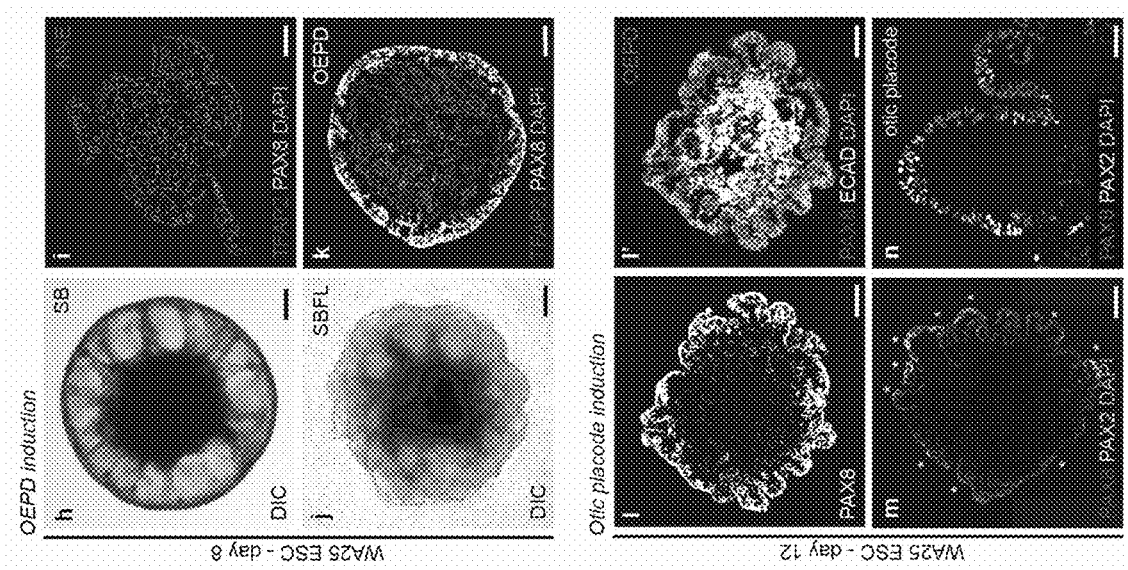
FIGS. 1A-1N, CONTINUED

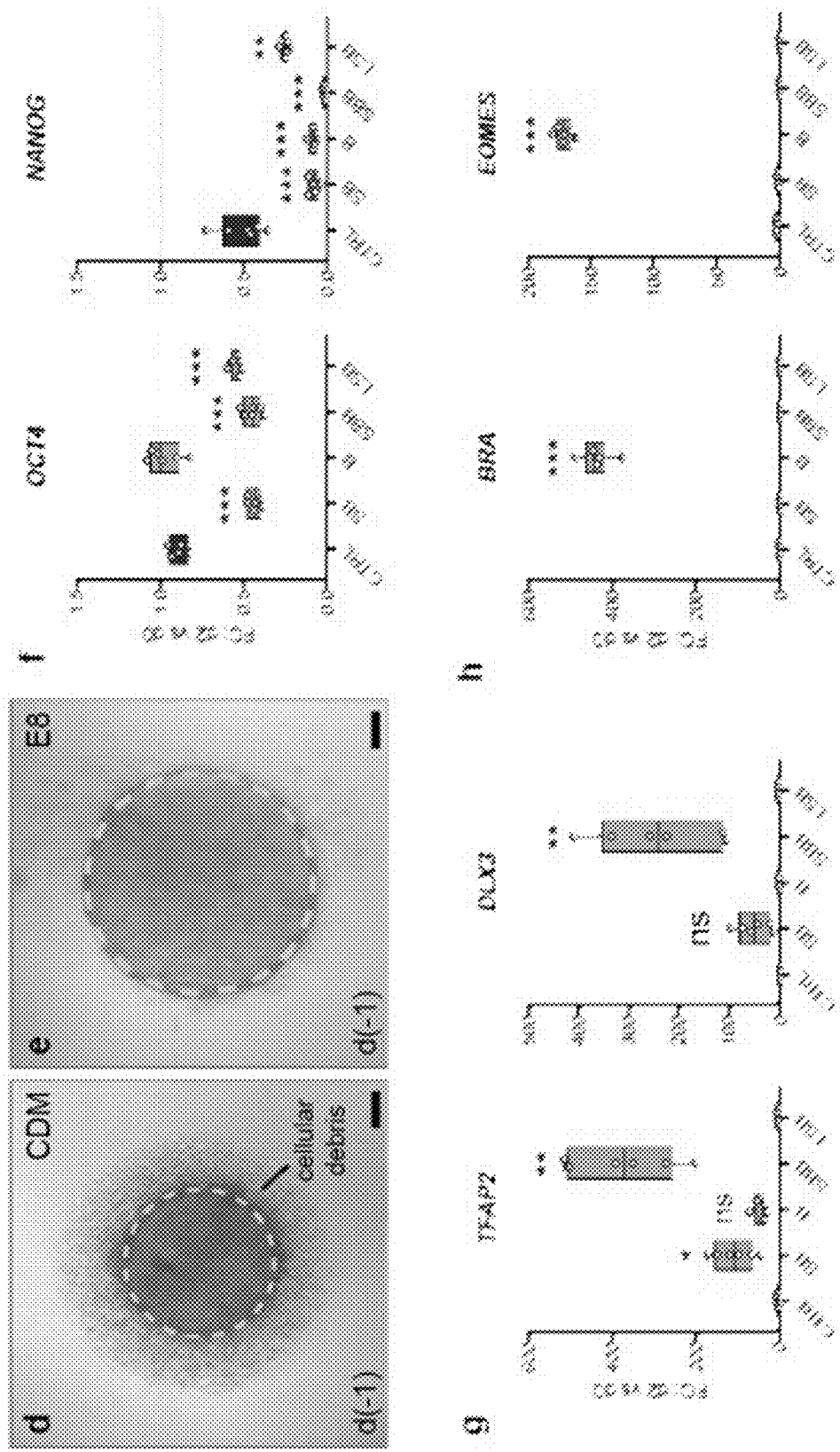
FIGS. 2A-2H, CONTINUED

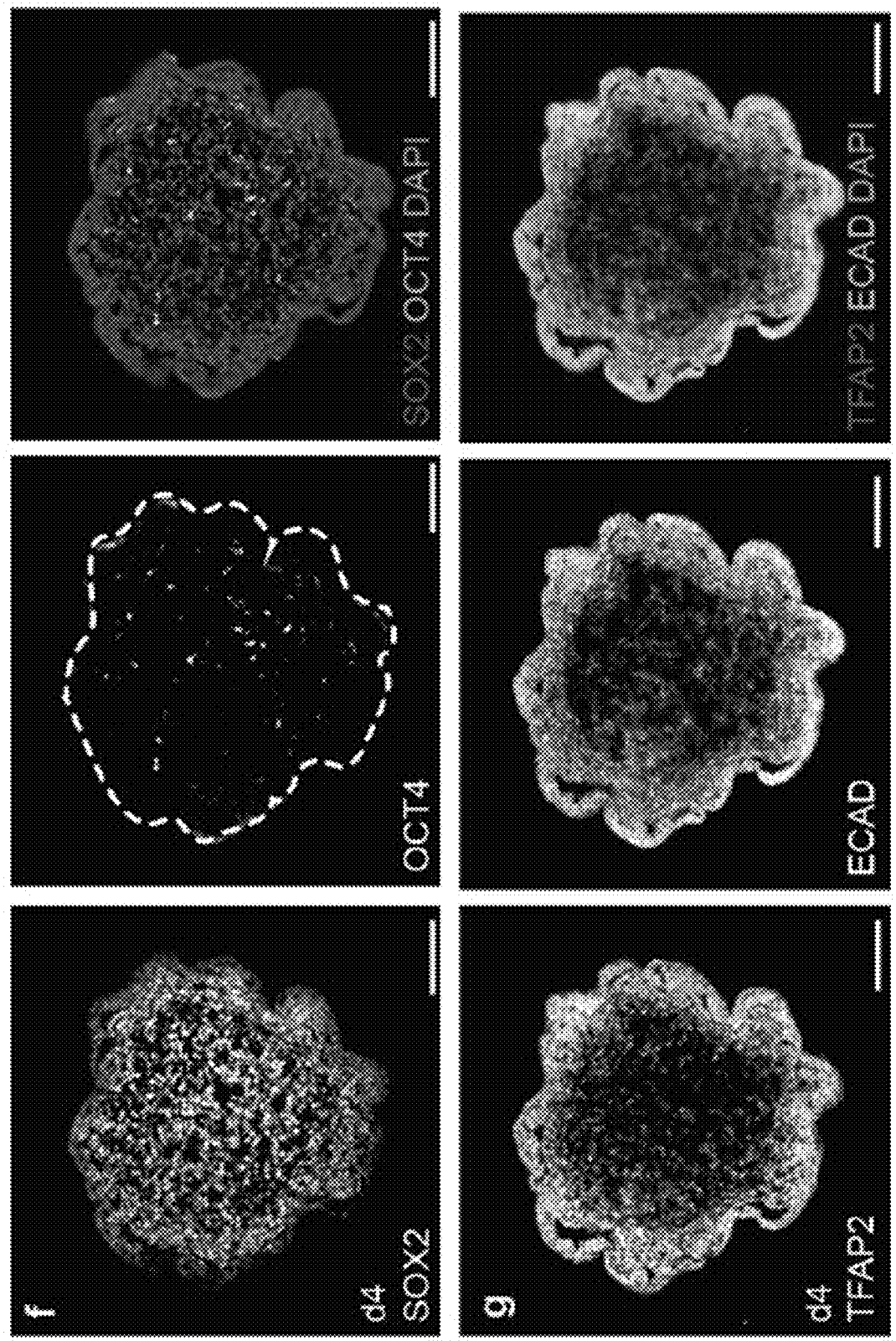
FIGS. 3A-3G, CONTINUED

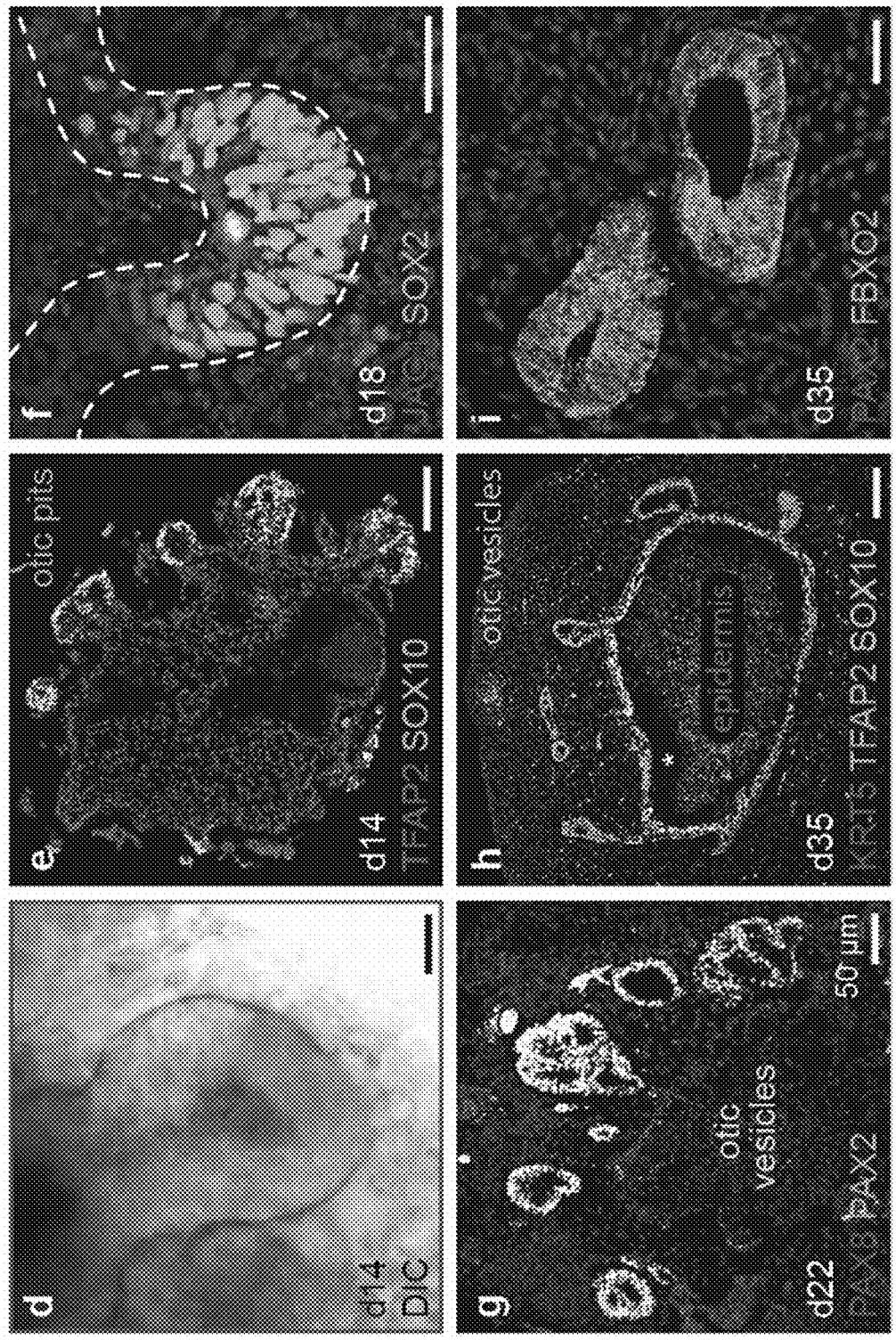
FIGS. 4A-4R, CONTINUED

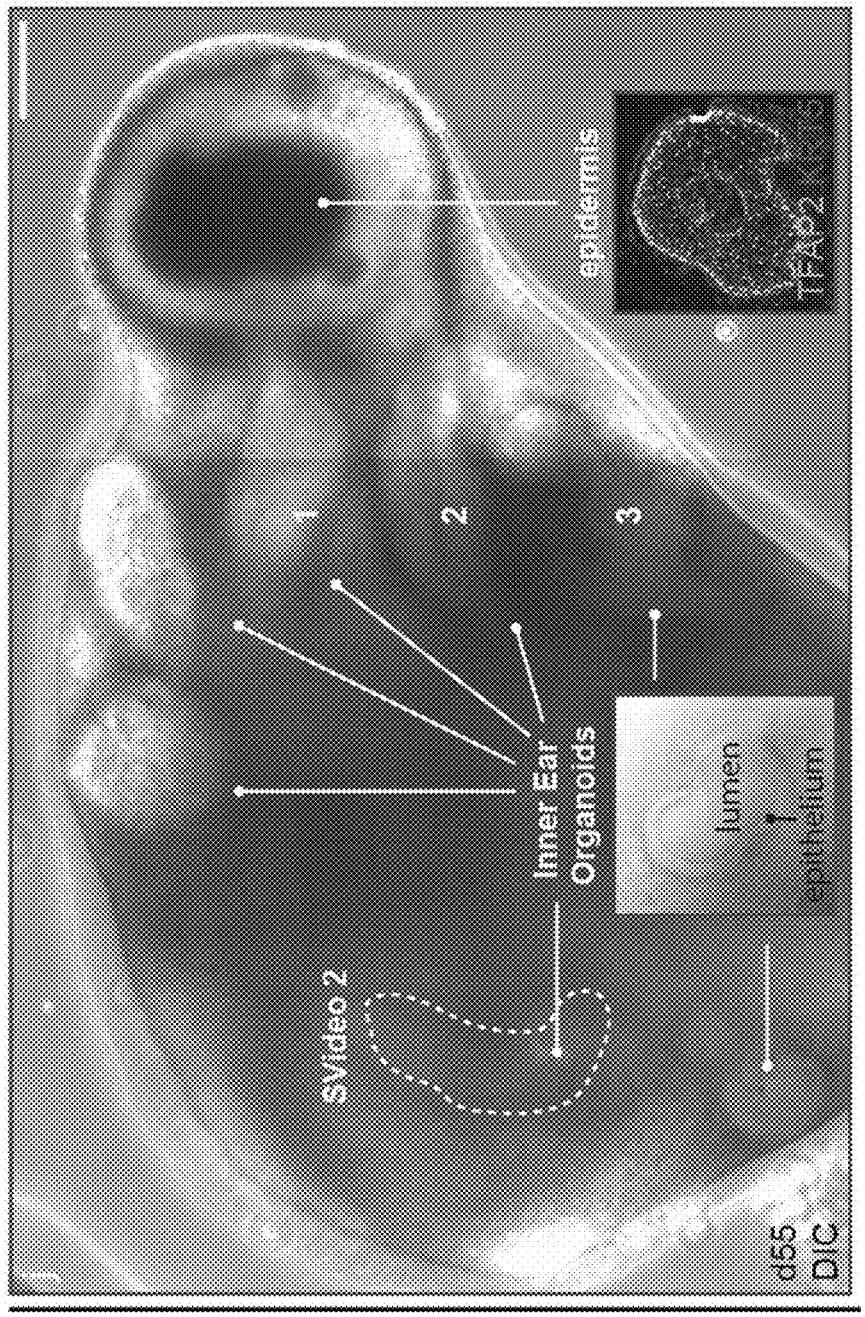
FIGS. 4A-4R, CONTINUED

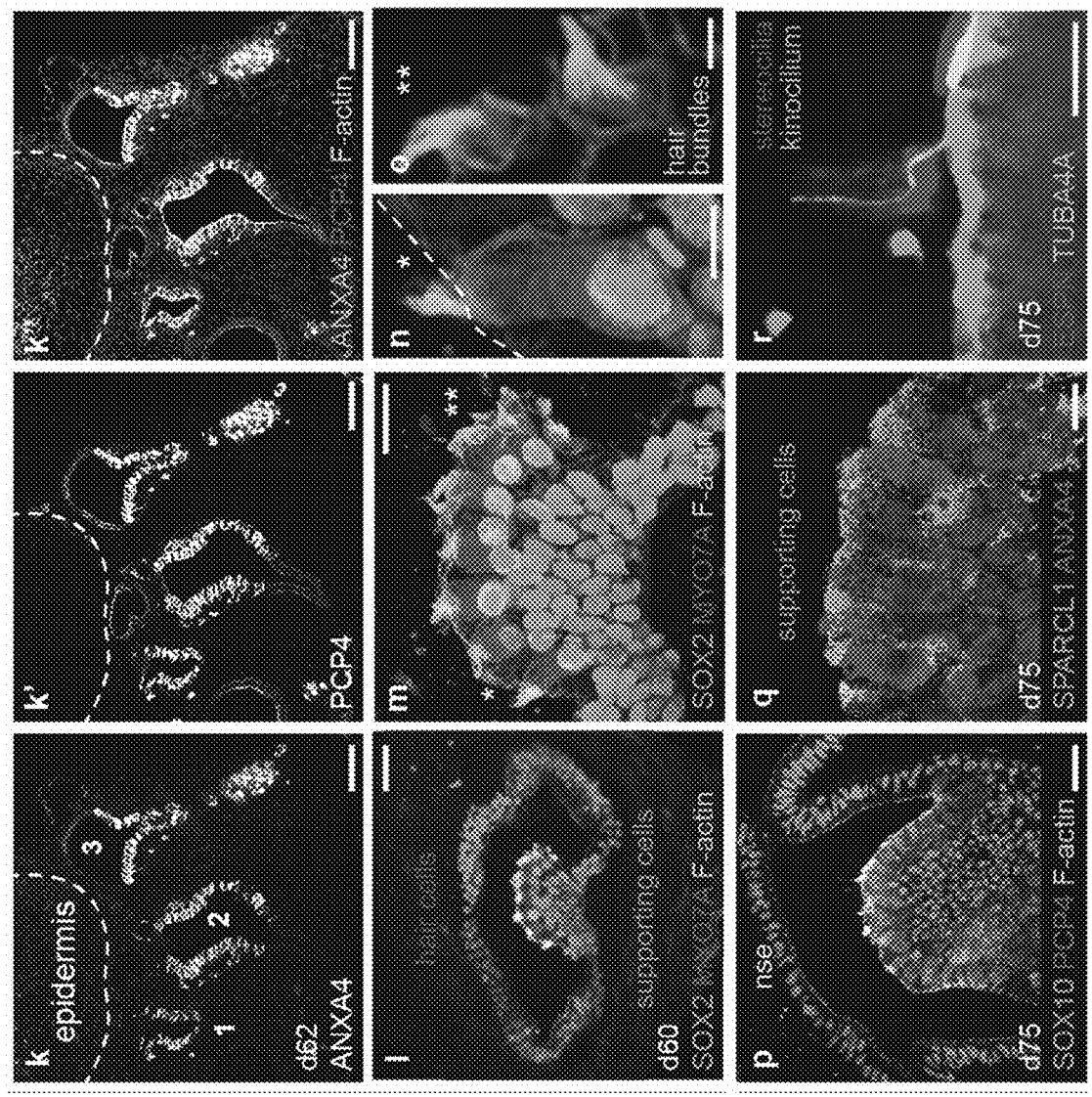
FIGS. 4A-4R, CONTINUED

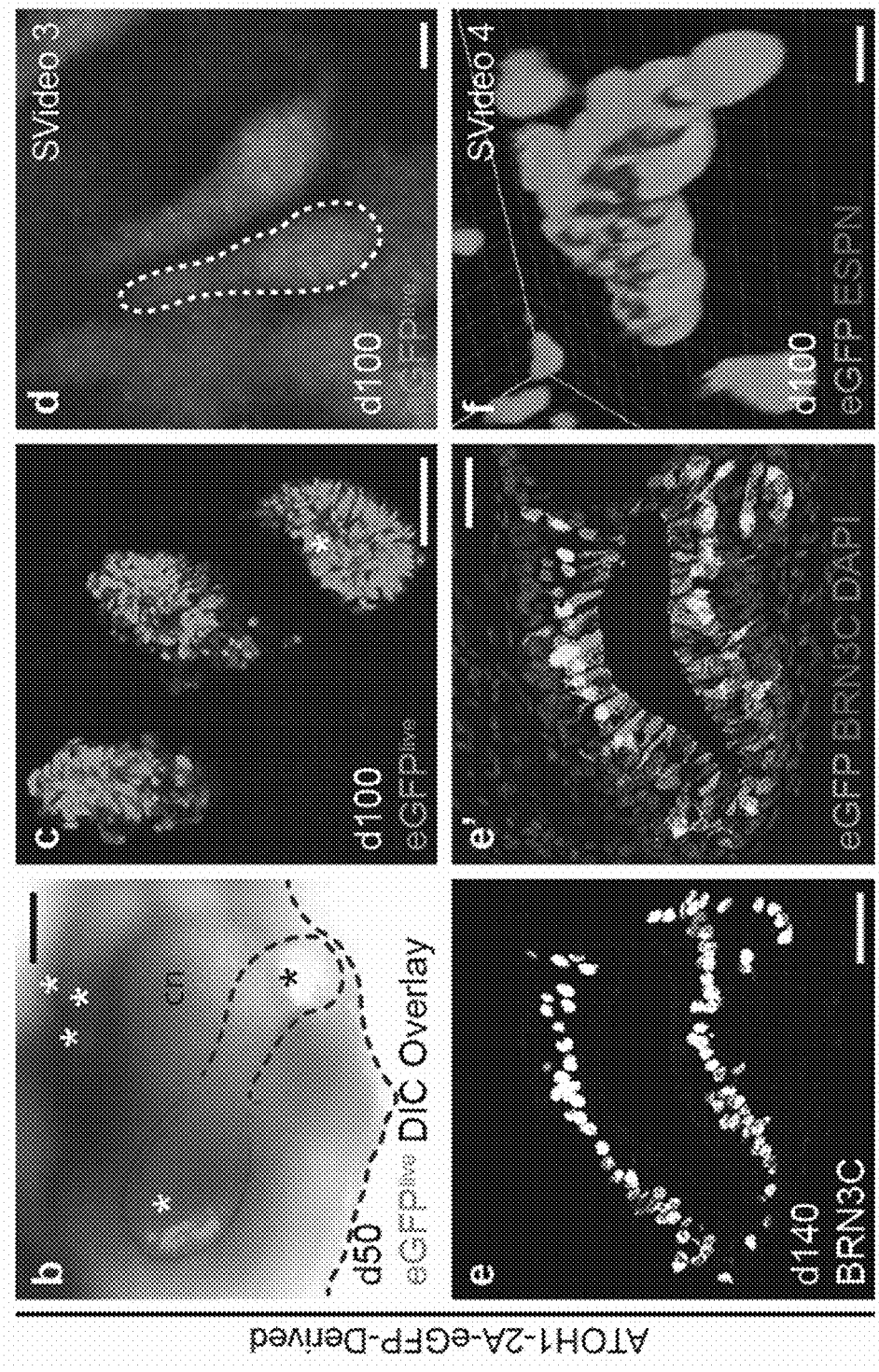
FIGS. 5A-5K, CONTINUED

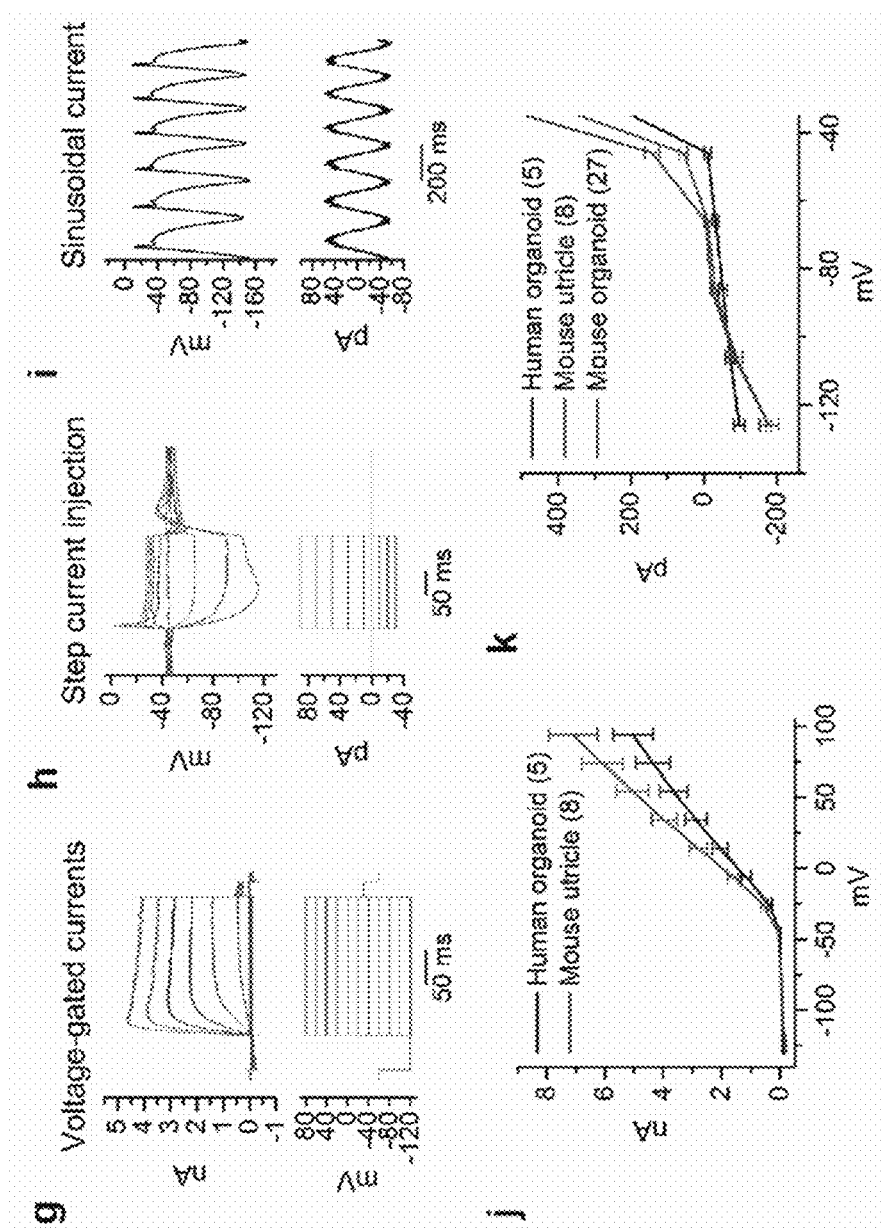
FIGS. 5A-5K, CONTINUED

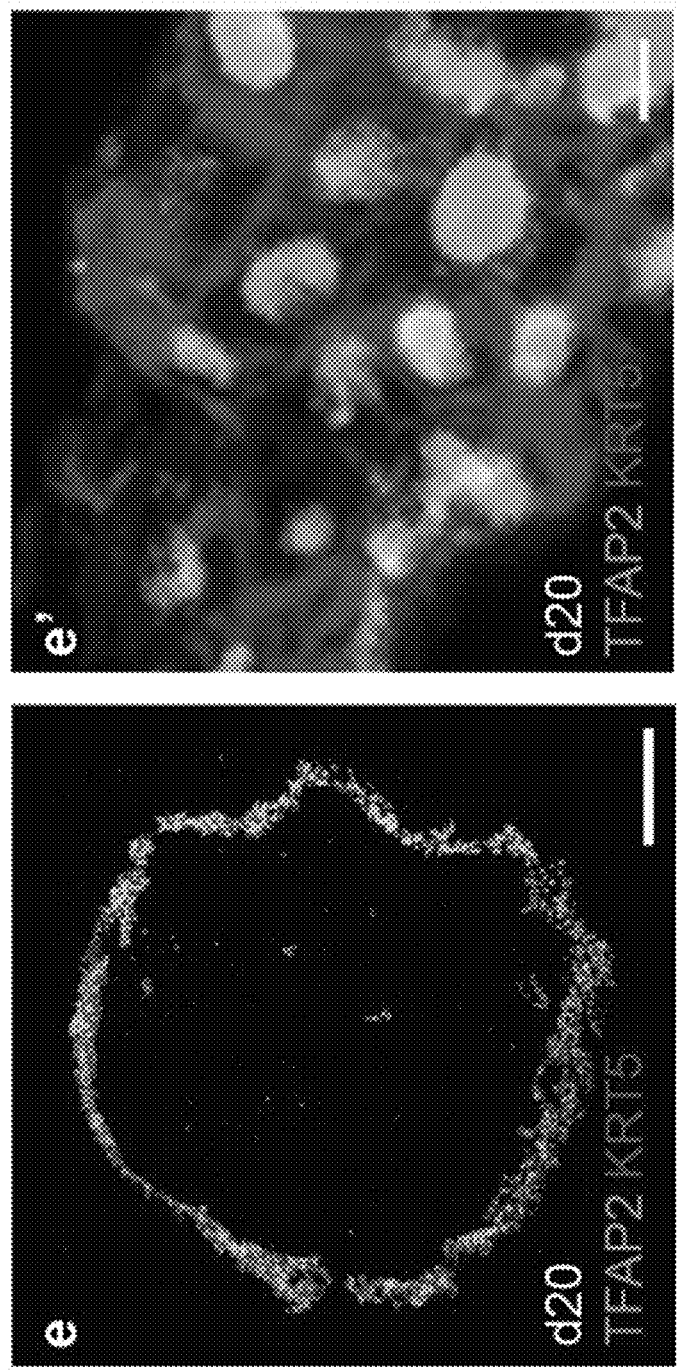
FIGS. 6A-6E, CONTINUED

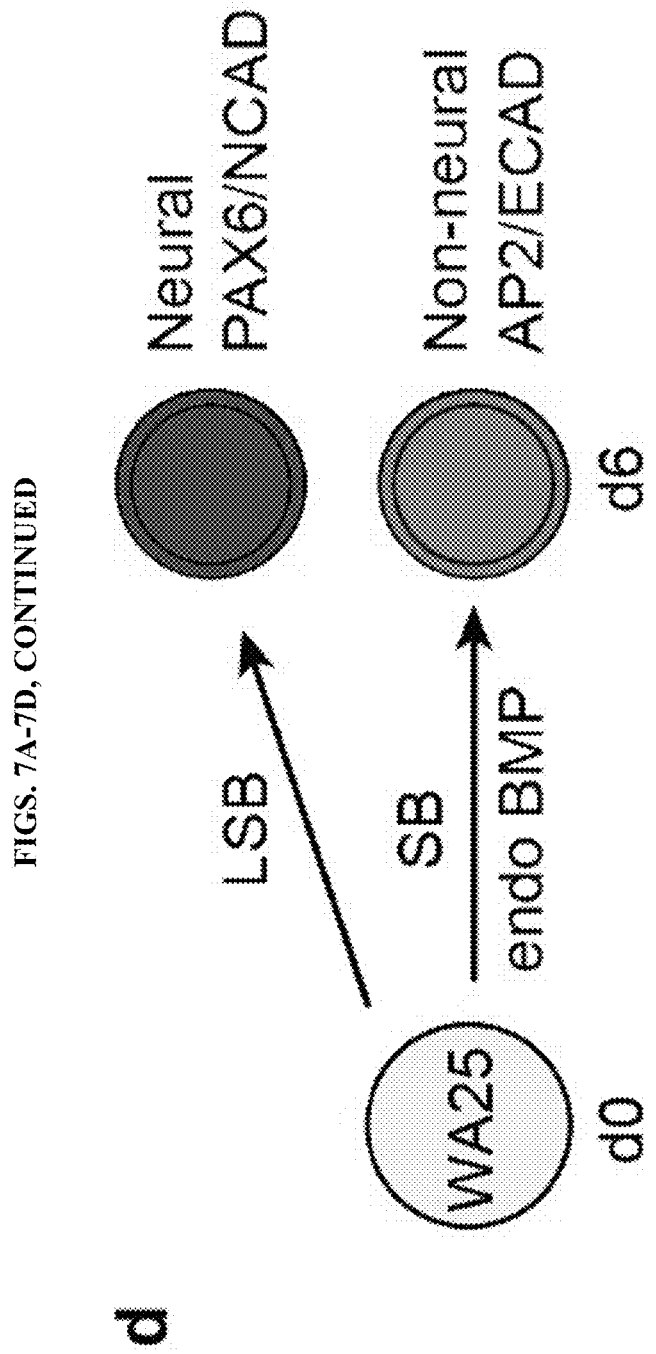
FIGS. 7A-7D, CONTINUED

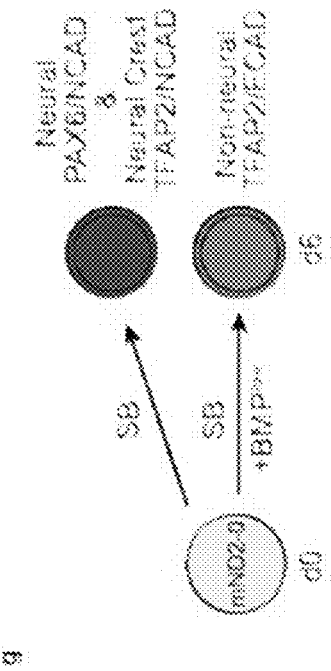
FIGS. 8A-8G
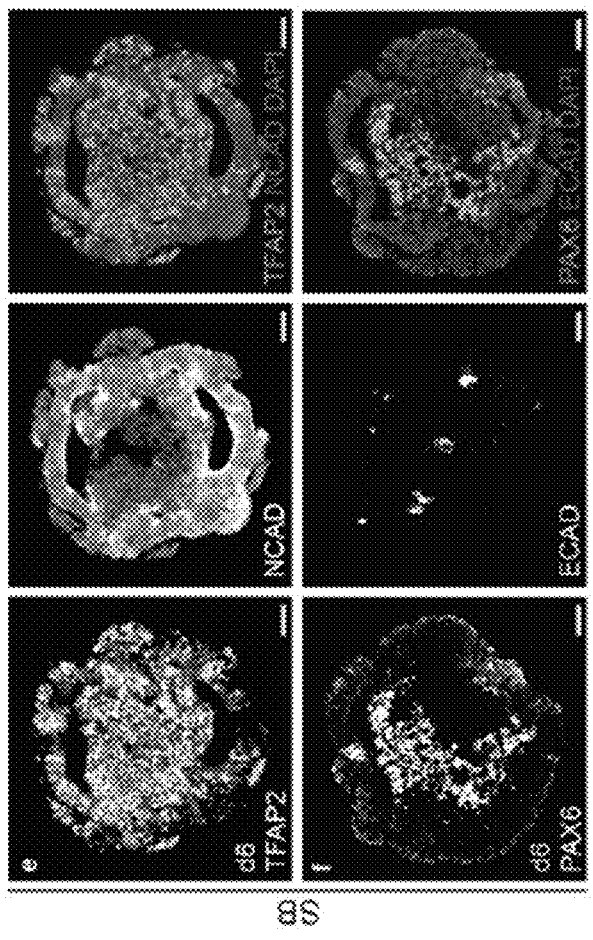

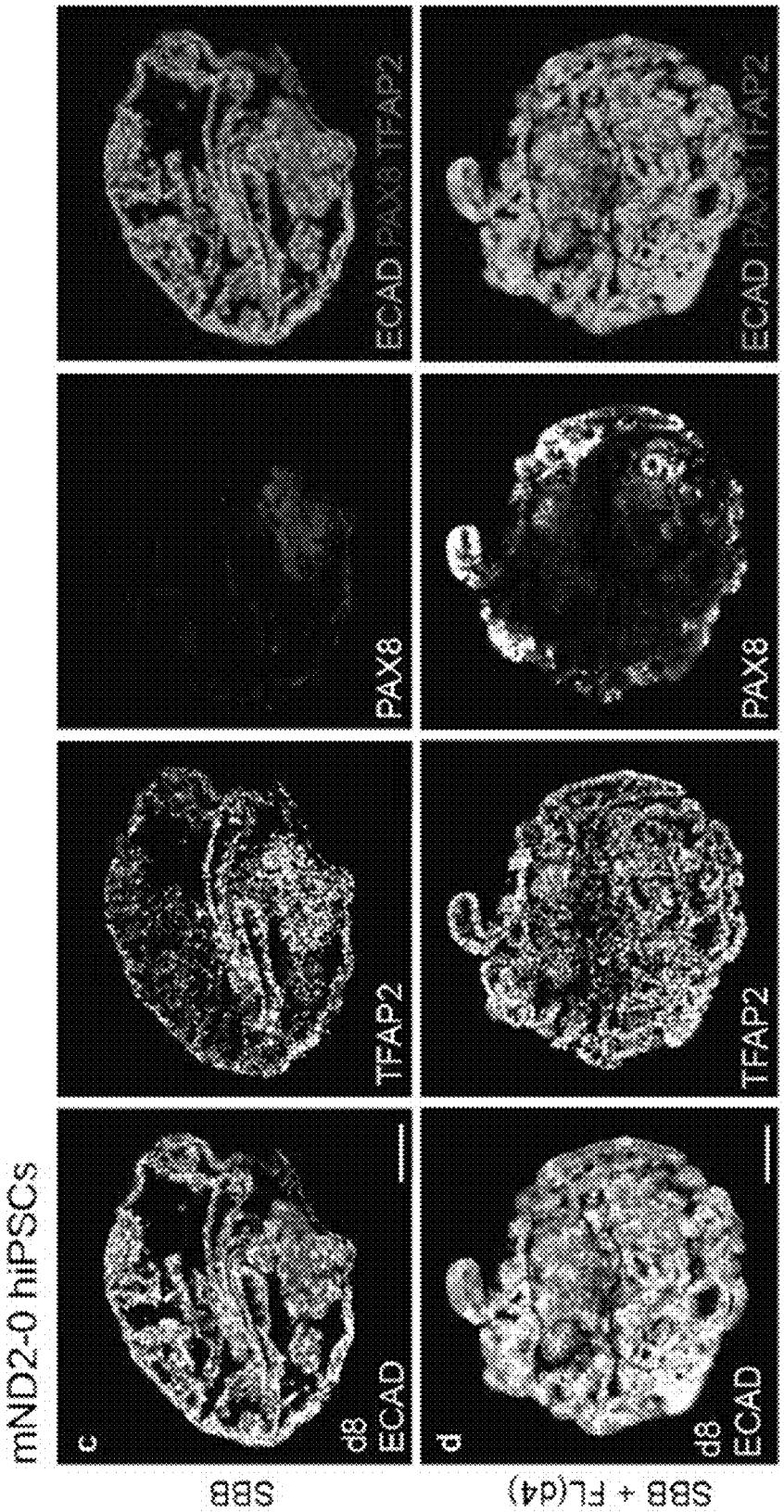
FIGS. 10A-10D, CONTINUED

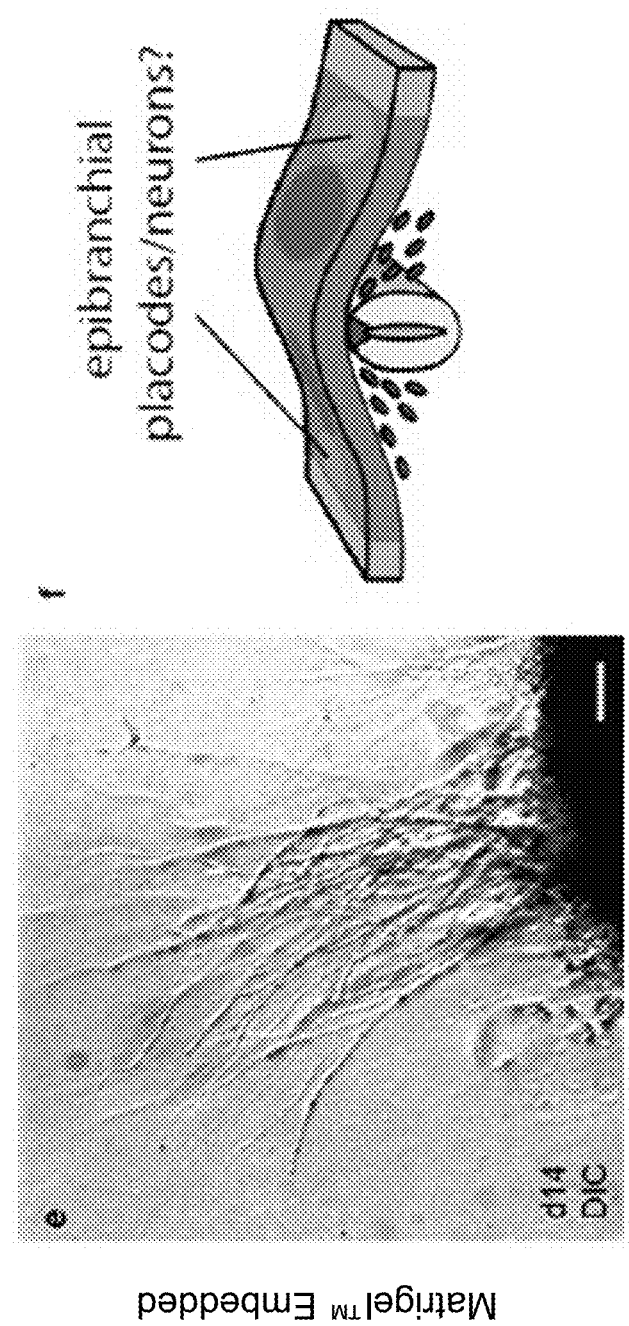
FIGS. 11A-11F, CONTINUED

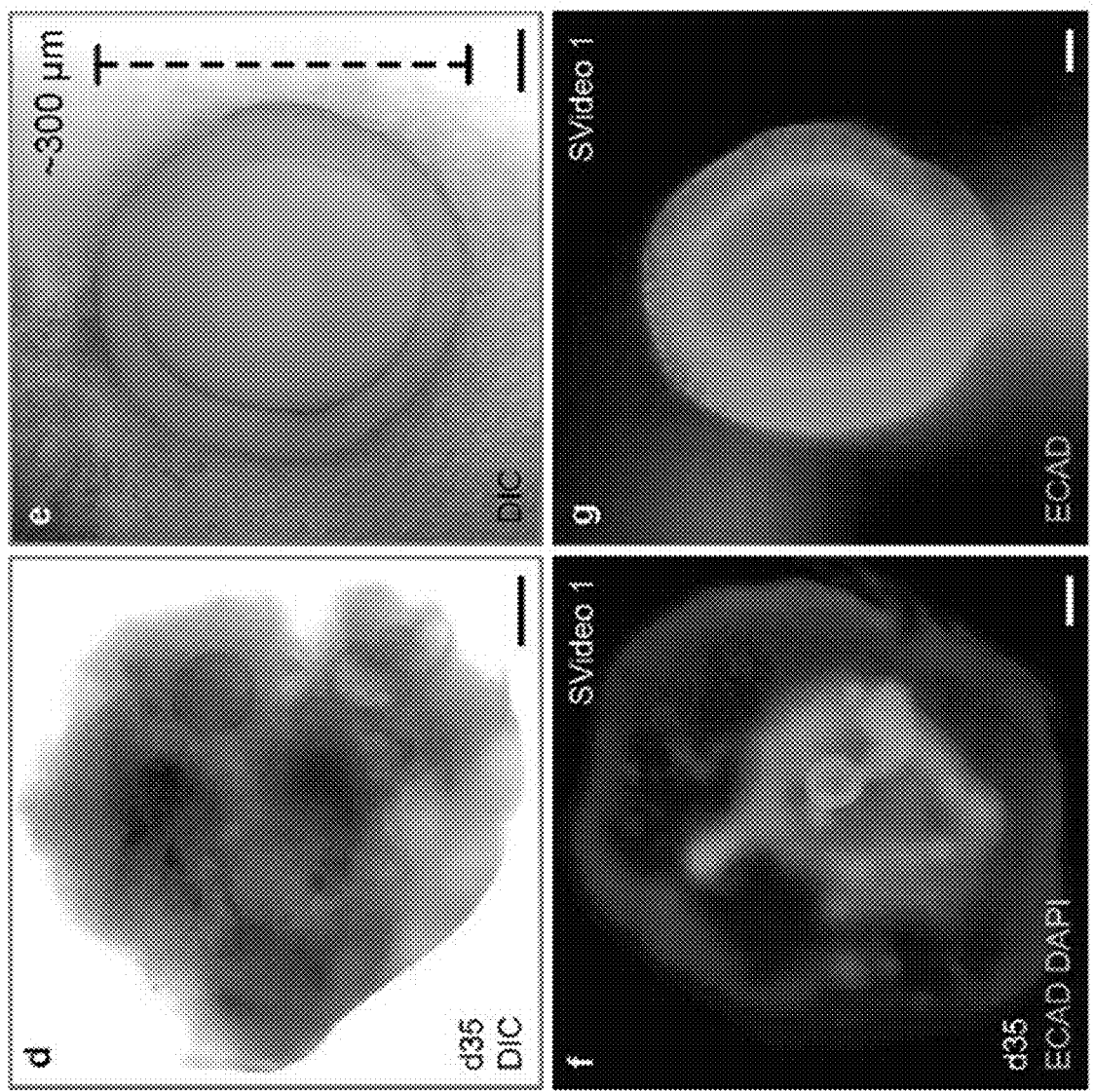
FIGS. 13A-13G, CONTINUED

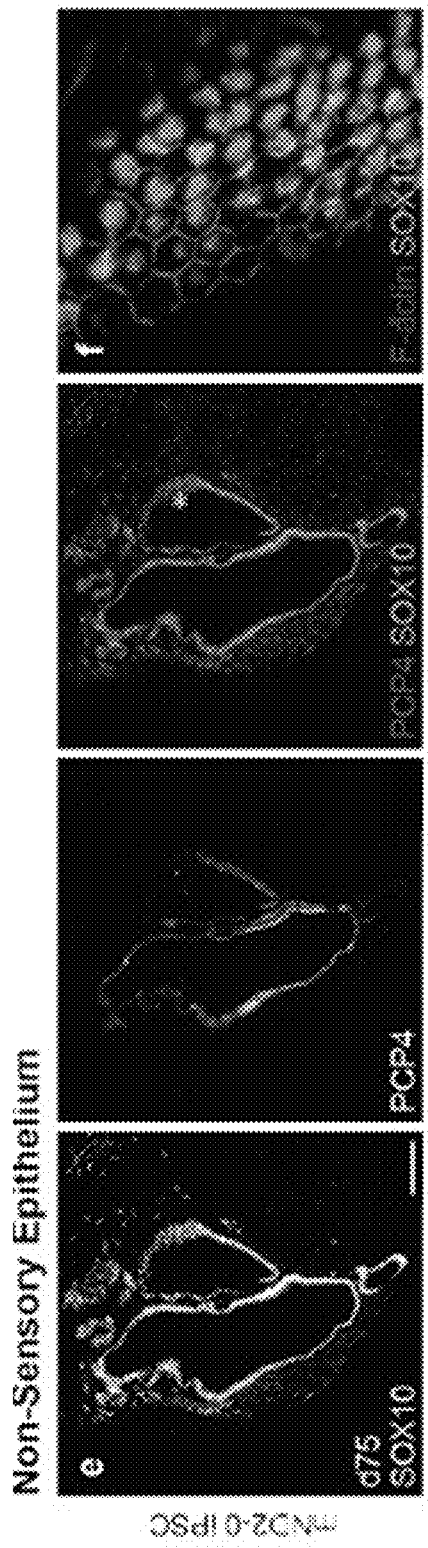
FIGS. 14A-14E, CONTINUED

FIG. 15

| Study Name | Chen et al. protocol (Nature, 2012)[2] | Ronaghi et al. protocol (Stem Cells Dev., 2014)[3] | Ealy et al. protocol (PNAS, 2016)[9] | Koehler et al. protocol (Current) |
|---|---|---|---|---|
| Culture format | 2D | 3D to 2D | 2D | 3D |
| Demonstration of non-neural induction | (Not shown) | Yes | Yes | Yes |
| Analysis of "off-target" lineages included (e.g. mesoderm, neuroectoderm, etc.) to confirm proper lineage commitment | (Not shown) | Yes | Yes | Yes |
| Demonstration of pre-placodal or otic-epibranchial progenitor domain induction | (Not shown) | Yes | Yes | Yes |
| Expression of hair cell marker genes | Yes | Yes | Yes | Yes |
| Multiple hair cell marker genes co-expressed in the same cells | Yes | Yes | (Not shown) | Yes |
| Hair bundle morphology | Disorganized | Mostly disorganized. Organized morphology "in rare instances" | (Not shown) | Organized |
| Electrophysiological responses | Yes | (Not shown) | (Not shown) | Yes |
| Presence of supporting cells | (Not shown) | Yes | (Not shown) | Yes |
| Correct spatial relationship between supporting cells and hair cells | (Not shown) | No | (Not shown) | Yes |
| Presence of sensory neurons | Yes | (Not shown) | (Not shown) | Yes |
| Hair cell or hair cell-like cell generation efficiency | "A small subset" of cells differentiated from the OEPs population | 1.79% – 5.89% | (Not shown) | Hair cells present in ~17% of aggregates |

ATOH1-2A-eGFP-PGK-Puro donor plasmid (SEQ ID NO:21)

FIG. 19, CONTINUED

```
                              gcccgcccaagaccgcagcgccgaccgaaaggagcgcacgacccatgcatcgatg
atatcagatcccggt ctcgagatccgaaccttaat                                agctc
cctcgaagaggttcactaGGCGCGCC
```

```
TCTAGAGTCGACCTGCAGGCATGCAAGCTTGGCGTAATCATGGTCATAGCTGTTT
CCTGTGTGAAATTGTTATCCGCTCACAATTCCACACAACATACGAGCCGGAAGCATAAAGTGTAAAGCCTG
GGGTGCCTAATGAGTGAGCTAACTCACATTAATTGCGTTGCGCTCACTGCCCGCTTTCCAGTCGGGAAAC
CTGTCGTGCCAGCTGCATTAATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCGAGCGGTATCAGCTCACTCA
AAGGCGGTAATACGGTTATCCACAGAATCAGGGGATAACGCAGGAAAGAACATGTGAGCAAAAGGCCAG
CAAAAGGCCAGGAACCGTAAAAAGGCCGCGTTGCTGGCGTTTTTCCATAGGCTCCGCCCCCCTGACGAG
CATCACAAAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACTATCGT
CTTGAGTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGCAGAAAAAAAGGATC
TCAAGAAGATCCTTTGATCTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACCTATCTCAGCGATCT
GTCTATTTCGTTCATCCATAGTTGCCTGACTCCCCGTCGTGTAGATAACTACGATACGGGAGGGCTTACCA
TCTGGCCCCAGTGCTGCAATGATACCGCGAGACCCACGCTCACCGGCTCCAGATTTATCAGCAATAAACC
AGCCAGCCGGAAGGGCCGAGCGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTCCCAACGATCAAGGCGAGTTA
CATGATCCCCCATGTTGTGCAAAAAAGCGGTTAGCTCCTTCGGTCCTCCGATCGTTGTCAGAAGTAAGTT
GGCCGCAGTGTTATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGACCGAGTTGCTCT
TGCCCGGCGTCAATACGGGATAATACCGCGCCACATAGCAGAACTTTAAAAGTGCTCATCATTGGAAAAC
GTTCTTCGGGGCGAAAACTCTCAAGGATCTTACCGCTGTTGAGATCCAGTTCGATGTAACCCACTCGTGC
ACCCAACTGATCTTCAGCATCTTTTACTTTCACCAGCGTTTCTGGGTGAGCAAAAACAGGAAGGCAAAATG
CCGCAAAAAAGGGAATAAGGGCGACACGGAAATGTTGAATACTCATACTCTTCCTTTTTCAATATTATTGA
GCATTTATCAGGGTTATTGTCTCATGAGCGGATACATATTTGAATGTATTTAGAAAAATAAACAAATAGGGG
TTCCGCGCACATTTCCCCGAAAAGTGCCACCTGACGTCTAAGAAACCATTATTATCATGACATTAACCTAT
AAAAATAGGCGTATCACGAGGCCCTTTCGTC
```

FIG. 20

Genomic sequence of the homozygous/bi-allelic ATOH1-2A-eGFP cell line at the ATOH1 locus (SEQ ID NO:22)

Elements:
ATOH1 exon 1/1 without the stop codon
GFP

```
CTTTGATTGGCTGCTCGCACGCGCCTGCCCGCGCCCTCCATTGGCTGAGAAGACACGCGACCGGCGCG
AGGAGGGGGTTGGGAGAGGAGCGGGGGGAGACTGAGTGGCGCGTGCCGCTTTTTAAAGGGGCGCAGC
GCCTTCAGCAACCGGAGAAGCATAGTTGCACGCGACCTGGTGTGTGATCTCCGAGTGGGTGGGGGAGG
GTCGAGGAGGGAAAAAAAAATAAGACGTTGCAGAAGAGACCCGGAAAGGGCCTTTTTTTTGGTTGAGCTG
GTGTCCCAGTGCTGCCTCCGATCCTGAGCCTCCGAGCCTTTGCAGTGCAATGTCCCGCCTGCTGCATGC
AGAAGAGTGGGCTGAAGTGAAGGAGTTGGGAGACCACCATCGCCAGCCCCAGCCGCATCATCTCCCGCA
ACCGCCGCCGCCGCAGCCACCTGCAACTTTGCAGGCGAGAGAAGCATCCCGTCTACCCGCCTGAGC
TGTCCCTCCTGGACAGCACCGACCCACGCGCCTGGCTGGCTCCCACTTTGCAGGGCATCTGCACGGCAC
GCGCCGCCCAGTATTTGCTACATTCCCCGGAGCTGGGTGCCTCAGAGGCCGCTGCGCCCCGGGACGAG
GTGGACGGCCGGGGGGAGCTGGTAAGGAGGAGCAGCGGCGGTGCCAGCAGCAGCAAGAGCCCCGGGC
CGGTGAAAGTGCGGGAACAGCTGTGCAAGCTGAAAGGCGGGGTGGTGGTAGAGAGCTGGGCTGCAGC
CGCCAACGGGCCCCTTCCAGCAAACAGCTGAATGGGGTGCAGAAGCAGAGACGGCTAGCAGCCAACGC
CAGGGAGCGCGCAGGATGCATGGGCTGAACCACGCCTTCGACCAGCTGCGCAATGTTATCCCGTCGTT
CAACAACGACAAGAAGCTGTCCAAATATGAGACCCTGCAGATGGCCCAAATCTACATCAACGCCTTGTCC
GAGCTGCTACAAACGCCCAGCGGAGGGGAACAGCCACCGCCGCCTCCAGCCTCCTGCAAAAGCGACCA
CCACCACCTTCGCACCGCGGCCTCCTATGAAGGGGGCGCGGCCAACGGACCGCAGCTGGGGCTCAGC
AGGCTTCCGGAGGGAGCCAGCGGCCGACCCCGCGGAGTTGCCGGACTCGCTTCTCAGCCCCAGCT
TCTGCGGGAGGGTACTCGGTGCAGCTGGACGCTCTGCACTTCTCGACTTTCGAGGACAGCGCCCTGACA
GCGATGATGGCGCAAAAGAATTTGTCTCCTTCTCTCCCCGGGAGCATCTTGCAGCCAGTGCAGGAGGAAA
ACAGCAAAACTTCGCCTCGGTCCCACAGAAGCGACGGGGAATTTTCCCCCCATTCCCATTACAGTGACTC
GGATGAGGCAAGTGCTAGC
[...GFP sequence...]
GAATTCcgatcatattcaataaccccttaa[...]aggtccctcgaagaggttca
ctaGGCGCGCCGAAGGTGACAGAAGCCTGAAAACTGAGACAGAAACAAAACTGCCCTTTCCCAGTGCGCG
GGAAGCCCCGCGGTTAAAGATCCCCGCACCCTTTAATTTTTGCTCTGCGATGGTCGTTGTTTAGCAACGA
CTTGGCTTCAGATGGCAGCTACATTTGATGGTTTGCAAATGCCGCCGCTGTTCCAAACTTCCTACGGTCCA
TATTGTTTGATGAAAACTTTCTGTTAAAATTGTGTCCTTTCCGCCCACCTTCTGCTCCCCCTTTAGATAGAT
ACGGTATAATTGTAGGTACCCGTATATGGCATCATTATTCTAGTTCCCTGCTGCCAATACGCTGCTAAAAC
GTCGCATCTTCTCTGTCACTGGTTTGGGTTTAATTTATTTTACGCCCTGGGCATCCATCCTTGTGTGTTGC
GCACTCAAGTGTGGGAGATTTAGTCTTCCGAAGTTGTTTTCCAAAATGCACAATGAAACGCAAAATTAGTG
CTTCCAAAGTGGATAACTTTTGACTATGGAATTGTTAGAAAACAAGAAACTTTAAGGTTTATATATTGTATAA
ACATACCCAGTATGTGCATCCGATCGCGAGAACGTTGGCGTCTTTTAGGAAACTCCGCGCACGCACTTTA
TCAGCCGCTGCTGCGGTGGTGGCTCCAGGAGAAACTCAACTGCCAATTGCAGACCAGTTTTTTTTTTTTTA
AACACAGCCACTTATAATTCTTAAGCTCTTTGCAAATGTTTGTTTAAAAAATGAAAAATTAAAAAAAAATCTAG
TAGTGTCAAACGCATTTGGTCAATTTTATTTTGCTTTGTTAATATTAGAAAACTTATTTATTATTGTTTGCTAC
CATTTCTACTTATCTTGATTCATTTTTTACGTTTTCTACTCGAGATCATTTTATTTTAATTTAGCAAAGCCAAC
TGCCCTTGTTTAATGTATTTTGTTTGCAAATGATTAAAATAAATGTGAAAAGAAGCCTTTTGTCACTTATTC
CTTGAGTATAACTACTGAAAACAATTTTCAAATGAATGACTTTGAAGAATTGAGTTAAGTCTTCTATTCAATG
TCATTTATGCGATCTTACAGTTTTGAAGAAAAATGTTGTAAACTTGGTGCCTTCAGGTAGTATCAAAACCCC
TTCAAAGAAAAGCACTCAAGTCAATAATTAAATTGTGAGATAAAACTTCTTCCAAATTTGCAGCACAGTTTT
GCCTCTTTGATGGCCAGGATCTT
```

METHODS OF GENERATING HUMAN INNER EAR SENSORY EPITHELIA AND SENSORY NEURONS

CROSS-REFERENCE TO RELATED APPLICATIONS

This application is a division of U.S. patent application Ser. No. 15/769,254, filed Apr. 18, 2018, which represents the U.S. National Stage of International Application No. PCT/US2016/058121, filed Oct. 21, 2016, which claims the benefit of U.S. Provisional Application No. 62/244,568, filed Oct. 21, 2015, all of which are herein incorporated by reference in full.

STATEMENT REGARDING FEDERALLY SPONSORED RESEARCH OR DEVELOPMENT

This invention was made with government support under DC015624, DC012617, and DC013294 awarded by the National Institutes of Health. The government has certain rights in the invention.

FIELD OF THE INVENTION

Provided herein are methods for directing differentiation of human pluripotent stem cells into inner ear sensory epithelia and sensory neurons. More particularly, provided herein are methods for obtaining three-dimensional cultures comprising human pluripotent stem cell-derived pre-otic epithelium, otic vesicles, and inner ear sensory epithelia containing hair cells and supporting cells as well as sensory neurons innervating the sensory epithelia.

REFERENCE TO A SEQUENCE LISTING SUBMITTED VIA EFS-WEB

The content of the ASCII text file of the sequence listing named "144578_00297_seq_listing. TXT" which is 18.2 kb in size was created on Aug. 10, 2020 and electronically submitted via EFS-Web herewith is incorporated herein by reference in its entirety.

BACKGROUND OF THE INVENTION

Nearly half a billion people have hearing loss world-wide, yet there are no pharmacological, genetic, or cell therapies that can treat hearing loss. This method could be used to generate human inner ear stem cells, supporting cells, hair cells and neurons for cell therapies or for use in drug discovery.

Accordingly, there remains a need in the art, for efficient, reproducible, and xenogeneic material-free methods for differentiating human pluripotent stem cells into inner ear sensory tissue suitable for clinical cell therapies.

SUMMARY OF THE INVENTION

In a first aspect, provided herein is a method of obtaining human pre-otic epithelial cells. As described herein, the method comprises (a) culturing human pluripotent stem cell aggregates in a culture medium comprising a Bone Morphogenetic Protein (BMP) and an inhibitor of Transforming Growth Factor Beta (TGFβ) signaling for about eight to about 10 days; (b) further culturing the cultured aggregates of (a) in the presence of a Fibroblast Growth Factor (FGF) and an inhibitor of BMP signaling for about 4 days; and (b) contacting the further cultured aggregates of (b) to a Wnt agonist for about 4 days; whereby cells within the contacted aggregates differentiate into pre-otic epithelial cells. The FGF can be FGF-2. The BMP can be BMP2, BMP4, or BMP7. The inhibitor of BMP signaling can be LDN-193189. The inhibitor of TGFβ1-mediated signaling can be selected from the group consisting of SB431542 and A-83-01. The Wnt agonist can be an inhibitor of GSK3. The inhibitor of GSK3 is selected from the group consisting of CHIR99021, lithium chloride (LiCl), and 6-bromoindirubin-3'-oxime (BIO).

In another aspect, provided herein is a method of obtaining a three-dimensional composition comprising human inner ear sensory tissue, the method comprising the steps of (a) embedding human pre-otic epithelial cells obtained according to the method of claim 1 in a semi-solid culture medium comprising extracellular matrix protein; and (b) culturing the embedded pre-otic epithelial cells in the presence of a Wnt agonist for about 40 to about 60 days under conditions that promote self-assembly of embedded pre-otic epithelial cells into otic vesicles, whereby a three-dimensional composition comprising human inner ear sensory tissue is obtained. The Wnt agonist can be an inhibitor of GSK3, where the inhibitor of GSK3 is selected from the group consisting of CHIR99021, lithium chloride (LiCl), and 6-bromoindirubin-3'-oxime (BIO). The extracellular matrix can be a basement membrane extract (BME). The three-dimensional composition can comprise one or more mechanosensory cells. The three-dimensional composition can comprise one or more sensory neuron cells. The three-dimensional composition cam comprise one or more sensory neuron cells that form synaptic connections with mechanosensory cells.

These and other features, aspects, and advantages described herein will become better understood upon consideration of the following drawings, detailed description, and appended claims.

BRIEF DESCRIPTION OF THE DRAWINGS

FIG. 15 presents a comparison of human inner ear induction studies. 2D, two dimensional. 3D, three dimensional. OEPs: otic epithelial progenitors. Note: In Chen et al. (2012) protocol, the efficiency of OEPs generation is dependent on the cell line, plating density and the degree of cell separation. In Ronaghi et al. (2014) protocol, the 1.79% hair cell-like cell generation efficiency was calculated from cells with mid-level Atoh1-nGFP expression (19.8%× 9.03%=1.79%), which is believed to be "an indicator of a potential hair cell phenotype". If also considering cells with high Atoh1-nGFP expression and cells negative for Atoh1-nGFP expression, the hair cell-like cell generation efficiency is 5.89% (77.1%×5.24%+19.8%×9.03%+3.1%× 2.08%=5.89%).

FIG. 20 depicts the genomic sequence of the homozygous/bi-allelic ATOH1-2A-eGFP cell line at the ATOH1 locus (SEQ ID NO:22).

DETAILED DESCRIPTION

Figures 1A, 1N:
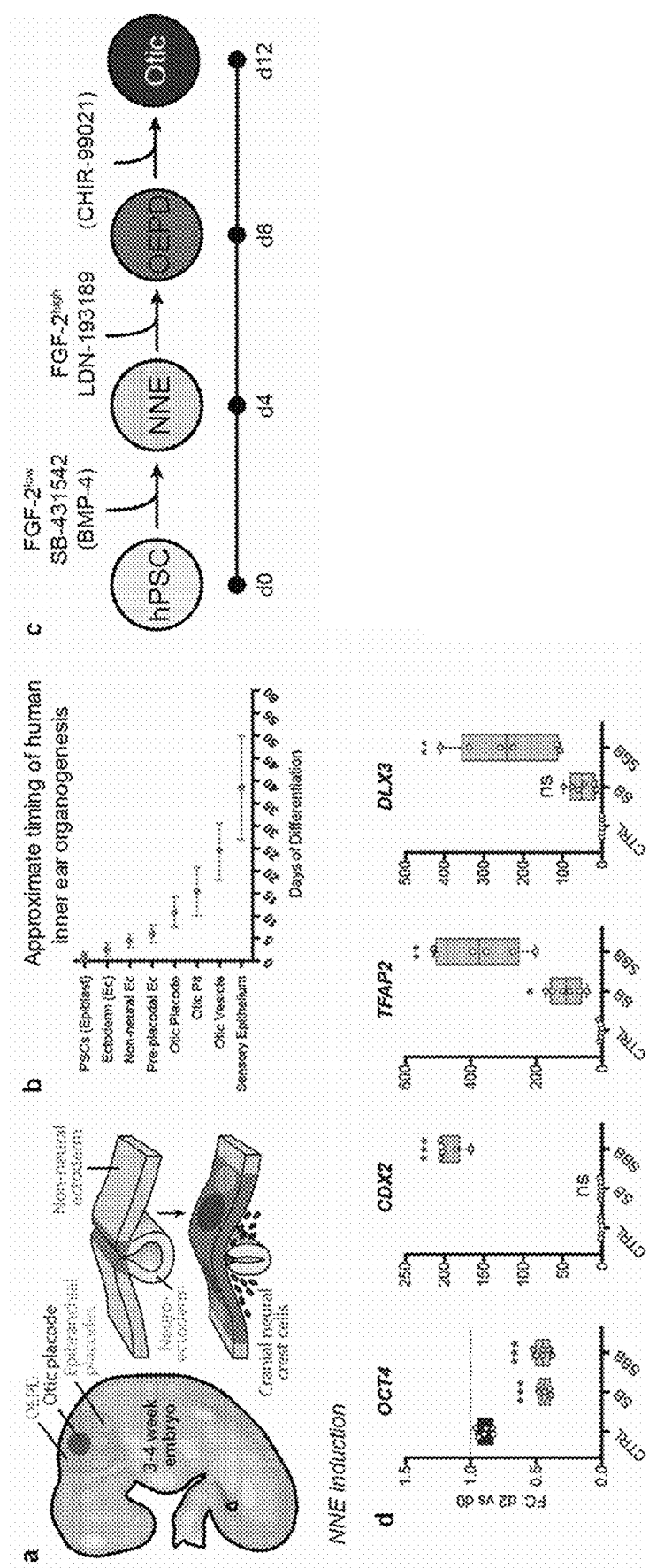
FIGS. 1A-1N demonstrate an exemplary protocol for step-wise induction of otic placode-like epithelia. a, Overview of mammalian ectoderm development in the otic placode cranial region. b, Timeline for key events of human otic induction. Day 0 on the timeline indicates the approximate stage of development represented by hPSC: ~12 dpc. c, Differentiation strategy for non-neural ectoderm (NNE), otic-epibranchial progenitor domain (OEPD), and otic placode induction. Potentially optional or cell line-dependent treatments are denoted in parentheses. d, qPCR analysis on day 2 of differentiation of WA25 cell aggregates treated with DMSO (Control), 10 µM SB, or 10 µM SB+10 ng/ml BMP4, denoted as SBB. Gene expression was normalized to undifferentiated hESCs; n=3 biological samples, 2 technical repeats; *P<0.05, P<0.01, *P<0.001; error bars=max/min. e, f, Representative TFAP2, ECAD, and PAX6 expression in WA25 aggregate treated with 10 µM SB or with 200 nM LDN+10 µM SB for 6 days. g, TFAP2, ECAD, and PAX6 expression in mND2-0 iPSCs treated with 10 µM SB+2.5 ng/ml BMP4 (SBB) on day 6. h, i, Representative image of a SB-treated WA25 aggregate on day 8: live (h) and immunostained with PAX8 and TFAP2 antibodies (i). When comparing morphology in panels (h) and (1) note that the outer-epithelium crumples into the aggregate core during the cryosectioning process. j, k, Representative image of a SB-treated WA25 aggregate on day 8 after treatment with 50 ng/ml FGF-2 and 200 nM LDN (SBFL) on day 4: live (j) and immunostained with PAX8 and TFAP2 antibodies (k). 1-n, WA25 SBFL-treated aggregates on day 12. The outer-epithelium contains PAX8$^+$ ECAD$^+$ cells (1) and occasional patches of PAX8$^+$ PAX2$^+$ otic placode-like cells (m, n). The specimens shown were treated with 25 µl of additional CDM on day 8. Scale bars, 100 µm (e-m), 50 µm (n).

All publications, patents, and patent applications mentioned in this specification are herein incorporated by reference in their entirety as if each individual publication, patent, and patent application was specifically and individually indicated to be incorporated by reference.

The present invention is based at least in part on the Inventors' discovery that human pluripotent stem cell-derived precursor cells cultured under conditions that are permissive towards differentiation and remodeling form highly uniform compositions of inner ear tissue that recapitulate the complexity and organization of human inner ear sensory epithelia and include functional hair cells. The Inventors discovered that it was possible to produce complex human tissues having the uniformity necessary for large-scale, quantitative in vitro modeling and screening applications.

Accordingly, the present invention relates to compositions including three-dimensional tissue constructs and cultures and methods of using such compositions as highly uniform models of human inner ear tissue and for screening drug candidates. In particular, provided herein are methods of efficiently and reproducibly producing and expanding complex, organized human inner ear sensory tissue suitable as a source of human hair cells for transplantation, as a model for understanding sensory deficits, and as a platform for screening drug candidates. An important advantage of the methods and systems provided herein is the ability to generate complex tissue constructs comprising multiple functional cell types from a single cell source. In addition, the methods and systems provided herein faithfully recapitulate in vivo development of complex, organized inner ear structural layers. The present invention provides a scalable and robust system for generating human inner ear sensory tissue as well as an important opportunity to study such tissues in an in vitro human model. In addition, methods of the present invention are useful for identifying materials and combinatorial strategies for human tissue engineering.

Methods

In exemplary embodiments, the methods provided herein comprise differentiating human pluripotent stem cells under conditions that promote differentiation of the pluripotent stem cells into inner ear sensory tissue. Generally, cells of inner ear sensory tissue are identified by their surface phenotype, by the ability to respond to growth factors, and being able to differentiate in vivo or in vitro into particular cell lineages.

In a first aspect, a method of obtaining human inner ear sensory tissue comprises aggregating human pluripotent stem cells into spheroids and culturing the spheroids for about three to four days in the presence of in a culture medium comprising factors that promote induction of non-neural epithelium (NNE). Such a culture medium comprises or consists essentially of the following chemically defined components: bone morphogenetic protein-4 (BMP4) and an inhibitor of transforming growth factor beta (TGFβ) signaling such as, for example, SB-431542 ("SB"), whereby at least a subset of the pluripotent stem cells are induced to differentiate to form a core of mesodermal cells within each aggregate. Preferably, aggregates comprising a core of mesodermal cells are cultured in the presence of BMP4 and an inhibitor of TGFβ signaling (e.g., SB) for about 8 days to about 10 days. SB-431542 is a specific inhibitor of the activin receptor-like kinase receptors ALK5, ALK4, and ALK7. Following the 8 to 10 day culture, cells of the mesodermal core migrate to the surface of the aggregates and produce a layer of non-neural epithelium within which inner ear organoids will develop. The non-neural epithelium that produces inner ear organoids, now lining the core of the aggregate, can eventually differentiate into epidermal tissue.

Referring to FIG. 1, NNE cells formed according to the culture step outlined above are cultured in the presence of a combination of Fibroblast Growth Factor (FGF) (e.g., FGF-2) and an inhibitor of bone morphogenetic protein (BMP) signaling, whereby the NNE cells differentiate into a pre-otic epithelium, also known as a otic-epibranchial progenitor domain (OEPD), from which the otic placode is derived. The OEPD is thickened relative to NNE cells cultured in the presence of a TGFB-signaling inhibitor alone and expresses a combination of posterior placode markers, such as PAX8, SOX2, TFAP2, ECAD, and NCAD. Inhibitors of BMP signaling appropriate for use according to the methods provided herein include, without limitation, LDN-193189 and SB-431542. LDN-193189 is a selective BMP signaling inhibitor that inhibits the transcriptional activity of the BMP type I receptors ALK2 and ALK3.

Next, aggregates comprising pre-otic epithelium (i.e., OEPD) are embedded in a semi-solid culture medium such as, for example, a semi-solid composition of extracellular matrix proteins. The embedded aggregates are then cultured in the presence of a Wnt agonist until pre-otic epithelium self-assembles into organized otic vesicles. In some cases, aggregates comprising pre-otic epithelium are cultured in the presence of a Wnt agonist for about 10 days to about 14 days (e.g., about 10, 11, 12, 13, or 14 days).

Otic vesicle-laden aggregates are further cultured for at least about 40 days (e.g., about 40 days, about 45 days, about 50 days, about 60 days, about 65 days, about 70 days, about 75 days, or more), during which inner ear organoids comprising mechanosensory cells (e.g., hair cells) are obtained. Hair cells are specialized mechanosensory receptor cells of the vertebrate inner ear and lateral line organs that mediate hearing and balance.

To form aggregates, a confluent culture of pluripotent stem cells can be chemically, enzymatically or mechanically dissociated from a surface, such as Matrigel® into clumps, aggregates, or single cells. In exemplary embodiments, the dissociated cells (as clumps, aggregates, or single cells) are plated onto a surface in a protein-free basal medium such as Dulbecco's Modified Eagle's Medium (DMEM)/F12, mTeSR™ (StemCell Technologies; Vancouver, British Columbia, Canada), and TeSR™. The full constituents and methods of use of TeSR™ are described in Ludwig et al. See, e.g., Ludwig T, et al., "Feeder-independent culture of human embryonic stem cells," *Nat. Methods* 3:637-646 (2006); and Ludwig T, et al., "Derivation of human embryonic stem cells in defined conditions," *Nat. Biotechnol.* 24:185-187 (2006), each of which is incorporated herein by reference as if set forth in its entirety. Other DMEM formulations suitable for use herein include, e.g., X-Vivo (BioWhittaker, Walkersville, MD) and StemPro® (Invitrogen; Carlsbad, CA).

In some cases, aggregates of pluripotent stem cells are cultured in the presence of a Rho kinase (ROCK) inhibitor. Kinase inhibitors, such as ROCK inhibitors, are known to protect single cells and small aggregates of cells. See, e.g., US Patent Application Publication No. 2008/0171385, incorporated herein by reference as if set forth in its entirety; and Watanabe K, et al., "A ROCK inhibitor permits survival of dissociated human embryonic stem cells," *Nat. Biotechnol.* 25:681-686 (2007). ROCK inhibitors are shown below to significantly increase pluripotent cell survival on chemically defined surfaces. ROCK inhibitors suitable for use herein include, but are not limited to, (S)-(+)-2-methyl-1-[(4-methyl-5-isoquinolinyl)sulfonyl]homopiperazine dihydrochloride (informal name: H-1152), 1-(5-isoquinolinesulfonyl)piperazine hydrochloride (informal name: HA-100), 1-(5-isoquinolinesulfonyl)-2-methylpiperazine (informal name: H-7), 1-(5-isoquinolinesulfonyl)-3-methylpiperazine (informal name: iso H-7), N-2-(methylamino)ethyl-5-isoquinoline-sulfonamide dihydrochloride (informal name: H-8), N-(2-aminoethyl)-5-isoquinolinesulphonamide dihydrochloride (informal name: H-9), N-[2-p-bromo-cinnamylamino)ethyl]-5-isoquinolinesulfonamide dihydrochloride (informal name: H-89), N-(2-guanidinoethyl)-5-isoquinolinesulfonamide hydrochloride (informal name: HA-1004), 1-(5-isoquinolinesulfonyl) homopiperazine dihydrochloride (informal name: HA-1077), (S)-(+)-2-Methyl-4-glycyl-1-(4-methylisoquinolinyl-5-sulfonyl)homopiperazine dihydrochloride (informal name: glycyl H-1152) and (+)-(R)-trans-4-(1-aminoethyl)-N-(4-pyridyl)cyclohexanecarboxamide dihydrochloride (informal name: Y-27632). The kinase inhibitor can be provided at a concentration sufficiently high that the cells survive and remain attached to the surface. An inhibitor concentration between about 3 µM to about 10 µM can be suitable. At lower concentrations, or when no ROCK inhibitor is provided, undifferentiated cells typically detach, while differentiated cells remain attached to the defined surface.

FGF-2 is an agonist of FGF signaling, and FGF signaling can be antagonized using, for example, the small molecule inhibitor PD-173074. BMP4 is an agonist of BMP signaling, and BMP signaling can be antagonized using, for example, the small molecule inhibitor LDN-193189. TGFβ-1 and Activin A are agonists of TGFβ signaling, and TGFβ signaling can be antagonized using, for example, the small molecule inhibitor SB-431542. CHIR-99021 is an agonist of the Wnt/β-catenin signaling pathway, and Wnt/β-catenin signaling can be antagonized using, for example, the small molecule inhibitor XAV-939. Other Wnt agonists include inhibitors/antagonists of the molecule Glycogen Synthase Kinase 3 (GSK3).

In some cases, the semi-solid composition of extracellular matrix proteins is a commercially available product such as Geltrex® basement membrane matrix. Geltrex® basement membrane matrix is suitable for use with human pluripotent stem cell applications using StemPro® hESC SFM or Essential 8™ media systems. In other cases, the semi-solid composition comprises two or more extra cellular matrix proteins such as, for example, laminin, entactin, vitronectin, fibronectin, a collagen, or combinations thereof.

Preferably, human pluripotent stem cells are cultured in a chemically-defined basal culture medium formulation comprising the defined components of culture medium "DF3 S" as set forth in Chen et al., *Nature Methods* 8:424-429 (2011), which is incorporated by reference herein as if set forth in its entirety. As used herein, the terms "E7 culture medium" and "E7" are used interchangeably and refer to a chemically defined culture medium comprising or consisting essentially of DF3S supplemented to further comprise insulin (20 µg/mL), transferrin (10.67 ng/mL) and human Fibroblast Growth Factor 2 (FGF2) (100 ng/mL). As used herein, the terms "E8 culture medium" and "E8" are used interchangeably and refer to a chemically defined culture medium comprising or consisting essentially of DF3S supplemented by the addition of insulin (20 µg/mL), transferrin (10.67 ng/mL), human FGF2 (100 ng/mL), and human TGFβ1 (Transforming Growth Factor Beta 1) (1.75 ng/mL).

Any appropriate method can be used to detect expression of biological markers characteristic of cell types described herein. For example, the presence or absence of one or more biological markers can be detected using, for example, RNA sequencing, immunohistochemistry, polymerase chain reaction, qRT-PCR, or other technique that detects or measures gene expression. In exemplary embodiments, a cell population obtained according to a method provided herein is evaluated for expression (or the absence thereof) of biological markers of pre-otic epithelial cells and otic placode such as Foxi1, Dlx genes, Pax8, Pax2, Sox3, Eya1, Gata3, Gbx2, and Sox9. Quantitative methods for evaluating expression of markers at the protein level in cell populations are also known in the art. For example, flow cytometry is used to determine the fraction of cells in a given cell population that express or do not express biological markers of interest. Differentiated cell identity is also associated with downregulation of pluripotency markers such as NANOG and OCT4 (relative to human ES cells or induced pluripotent stem cells).

As used herein, "pluripotent stem cells" appropriate for use according to a method of the invention are cells having the capacity to differentiate into cells of all three germ layers. Suitable pluripotent cells for use herein include human embryonic stem cells (hESCs) and human induced pluripotent stem (iPS) cells. As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60 and TRA-1-81, and appear as compact colonies having a high nucleus to cytoplasm ratio and prominent nucleolus. ESCs are commercially available from sources such as WiCell Research Institute (Madison, Wis.). As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007).

Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

Human iPS cells can be used according to a method described herein to obtain primitive macrophages and microglial cells having the genetic complement of a particular human subject. For example, it may be advantageous to obtain inner ear sensory cells that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, Yu et al., *Science* 324(5928):797-801 (2009); Chen et al., *Nat. Methods* 8(5):424-9 (2011); Ebert et al., *Nature* 457(7227):277-80 (2009); Howden et al., *Proc. Natl. Acad. Sci. U.S.A.* 108(16):6537-42 (2011). Induced pluripotent stem cell-derived inner ear sensory tissues can be used to screen drug candidates in tissue constructs that recapitulate inner ear sensory tissue in an individual having, for example, a particular disease. Subject-specific somatic cells for reprogramming into induced pluripotent stem cells can be obtained or isolated from a target tissue of interest by biopsy or other tissue sampling methods. In some cases, subject-specific cells are manipulated in vitro prior to use in a three-dimensional tissue construct of the invention. For example, subject-specific cells can be expanded, differentiated, genetically modified, contacted to polypeptides, nucleic acids, or other factors, cryo-preserved, or otherwise modified prior to introduction to a three-dimensional tissue construct.

Preferably, human pluripotent stem cells (e.g., human ESCs or iPS cells) are cultured in the absence of a feeder layer (e.g., a fibroblast layer), a conditioned medium, or a culture medium comprising poorly defined or undefined components. As used herein, the terms "chemically defined medium" and "chemically defined cultured medium" also refer to a culture medium containing formulations of fully disclosed or identifiable ingredients, the precise quantities of which are known or identifiable and can be controlled individually. As such, a culture medium is not chemically defined if (1) the chemical and structural identity of all medium ingredients is not known, (2) the medium contains unknown quantities of any ingredients, or (3) both. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that are free of serum obtained from animal (e.g., fetal bovine) blood. In general, culturing cells or tissues in the absence of animal-derived materials (i.e., under xenogen-free conditions) reduces or eliminates the potential for cross-species viral or prion transmission.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

As used herein, "a medium consisting essentially of" means a medium that contains the specified ingredients and those that do not materially affect its basic characteristics.

As used herein, "effective amount" means an amount of an agent sufficient to evoke a specified cellular effect according to the present invention.

As used herein, "about" means within 5% of a stated concentration range, density, temperature, or time frame.

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Example 1—Generation of Inner Ear Organoids with Functional Hair Cells from Human Pluripotent Stem Cells The human inner ear contains approximately 20,000 sensory hair cells that detect sound and movement via mechanosensitive stereocilia bundles[1]. Genetic mutations or environmental insults, such as loud noises, can cause irreparable damage to these hair cells, leading to dizziness or hearing loss[2,3]. We previously demonstrated how to generate inner ear organoids from mouse pluripotent stem cells (PSCs) using timed manipulation of the FGF, TGFβ, BMP, and Wnt signaling pathways in a 3D culture system[4-6]. We have shown that mouse inner ear organoids contain sensory hair cells with similar structure and function to native vestibular hair cells in the mouse inner ear[7]. Moreover, our past findings bolstered a working model of otic induction signaling dynamics, wherein BMP signaling activation and TGFβ inhibition initially specifies non-neural ectoderm and subsequent BMP inhibition and FGF activation induces a pre-otic fate[8,9]. Despite several recent attempts, a developmentally faithful approach for deriving functional hair cells from human PSCs (hPSC) has yet to be described[10-15]. Here, to generate human inner ear tissue from hPSCs, we first established a timeline of in vitro human inner ear organogenesis (FIGS. 1A, 1B). The inner ear arises from the ectoderm layer and, in humans, produces the first terminally differentiated hair cells by ~52 days post conception (dpc)[16]. Beginning with pluripotent cells in the epiblast, inner ear induction is initiated ~12 dpc with formation of the ectoderm epithelium. Then, the epithelium splits into the non-neural ectoderm (also known as surface ectoderm) and the neuroectoderm (FIGS. 1A, 1B). The non-neural ectoderm ultimately produces the inner ear as well as the epidermis of the skin; thus, in our initial experiments, we sought to establish a chemically defined 3D culture system for targeted derivation of non-neural ectoderm epithelia, from which we could derive inner ear organoids (FIGS. 1A-1C).

We first confirmed that dissociated human embryonic stem cells (hESCs; WA25 cell line, WiCell) aggregated well in E8 Medium containing a ROCK inhibitor, Y-27632, and displayed superior uniformity and cell-survival compared to cells aggregated in a chemically-defined differentiation medium (hereafter, CDM; FIGS. 2A-2H and Table 1).

TABLE 1

Chemically-Defined Differentiation Medium (CDM)

| Component | Supplier | Cat. No. | Stock Concentration | Final Concentration | Volume (200 ml) |
|---|---|---|---|---|---|
| F-12 Nutrient Mixture | Gibco | 31765-035 | — | 49% (v/v) | 100 ml |
| IMDM | Gibco | 31980-030 | — | 49% (v/v) | 100 ml |
| CD Lipid Conc. | Invitrogen | 11905-031 | 100X | 1X | 2 ml |
| BSA | Sigma | A1470 | — | 5 mg/ml | 1 g |
| Insulin | Sigma | I9278 | 10 mg/ml | 7 ug/ml | 140 ul |
| Transferrin | Sigma | T8158 | 20 mg/ml | 15 ug/ml | 150 ul |
| Thioglycerol | Sigma | M6145 | 11.5M | 450 uM | 8 ul |
| Normocin | Invitrogen | Ant-nr-1 | 50 mg/ml | 100 ug/ml | 400 ul |

Following a 2-day incubation in E8 Medium, we transferred aggregates to CDM containing a low concentration of Matrigel and FGF-2 to stimulate epithelization and ectoderm differentiation on the aggregate surface. We previously showed that a combination of BMP4 and the TGFβ inhibitor SB-431542 (hereafter, "SB") promoted non-neural induction from mouse PSCs (mPSCs)[6]. We found that combining 10 ng/ml BMP4 and 10 μM SB (dual SB/BMP4 treatment referred to as "SBB") induces not only non-neural marker genes, such as TFAP2 and DLX3, but also the extraembryonic marker CDX2 (FIG. 1D; FIGS. 3A-3G)[17]. In contrast, SB treatment alone led to an increase in TFAP2 and DLX3 expression with no corresponding CDX2 expression (FIG. 1D). Remarkably, 100% of SB treated aggregates generated TFAP2$^+$ E-cadherin (ECAD)$^+$ epithelium with a surface ectoderm-like morphology by days 4-6 of differentiation—a time scale consistent with human embryogenesis (n=15 aggregates, 3 experiments; FIGS. 1B-1E; FIGS. 3A-3G). Over a period of 20 days, the epithelium expanded into a cyst composed of TFAP2$^+$ Keratin-5 (KRT5)$^+$ keratinocyte-like cells (FIGS. 6A-6E). From these findings, we concluded that treating WA25 cell aggregates with SB is sufficient to induce a non-neural epithelium.

Figures 9A, 9B, 9C:
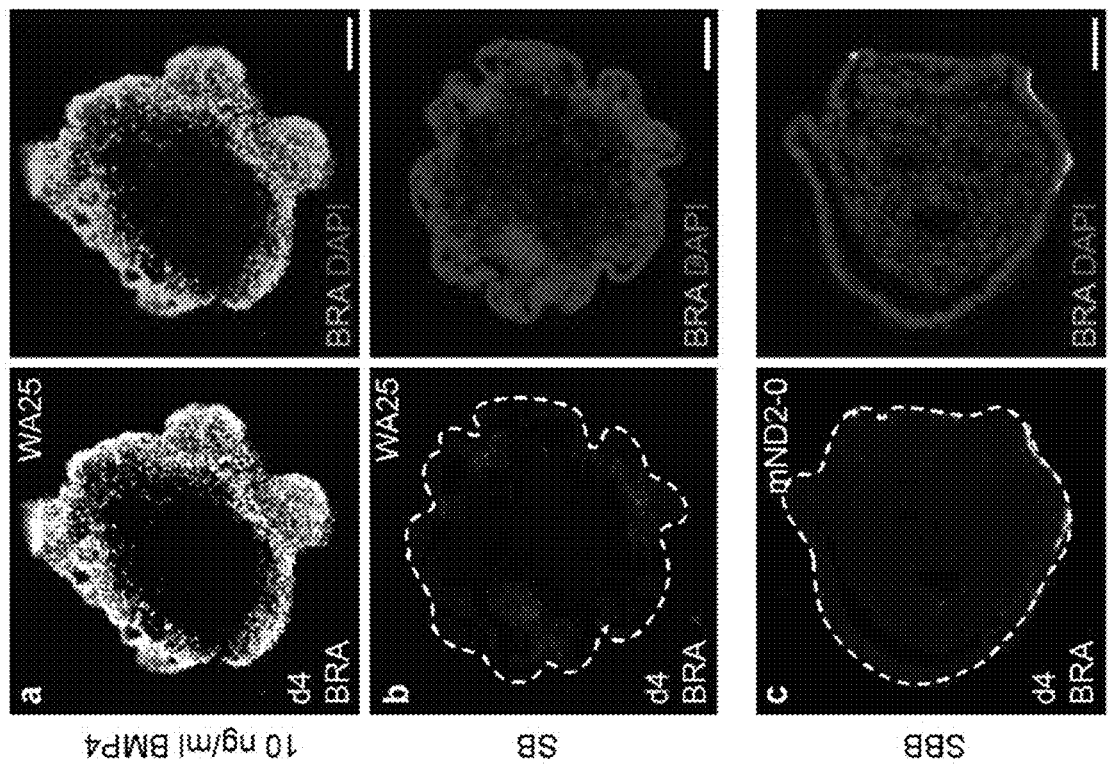
Figures 10A, 10B, 10C, 10D:
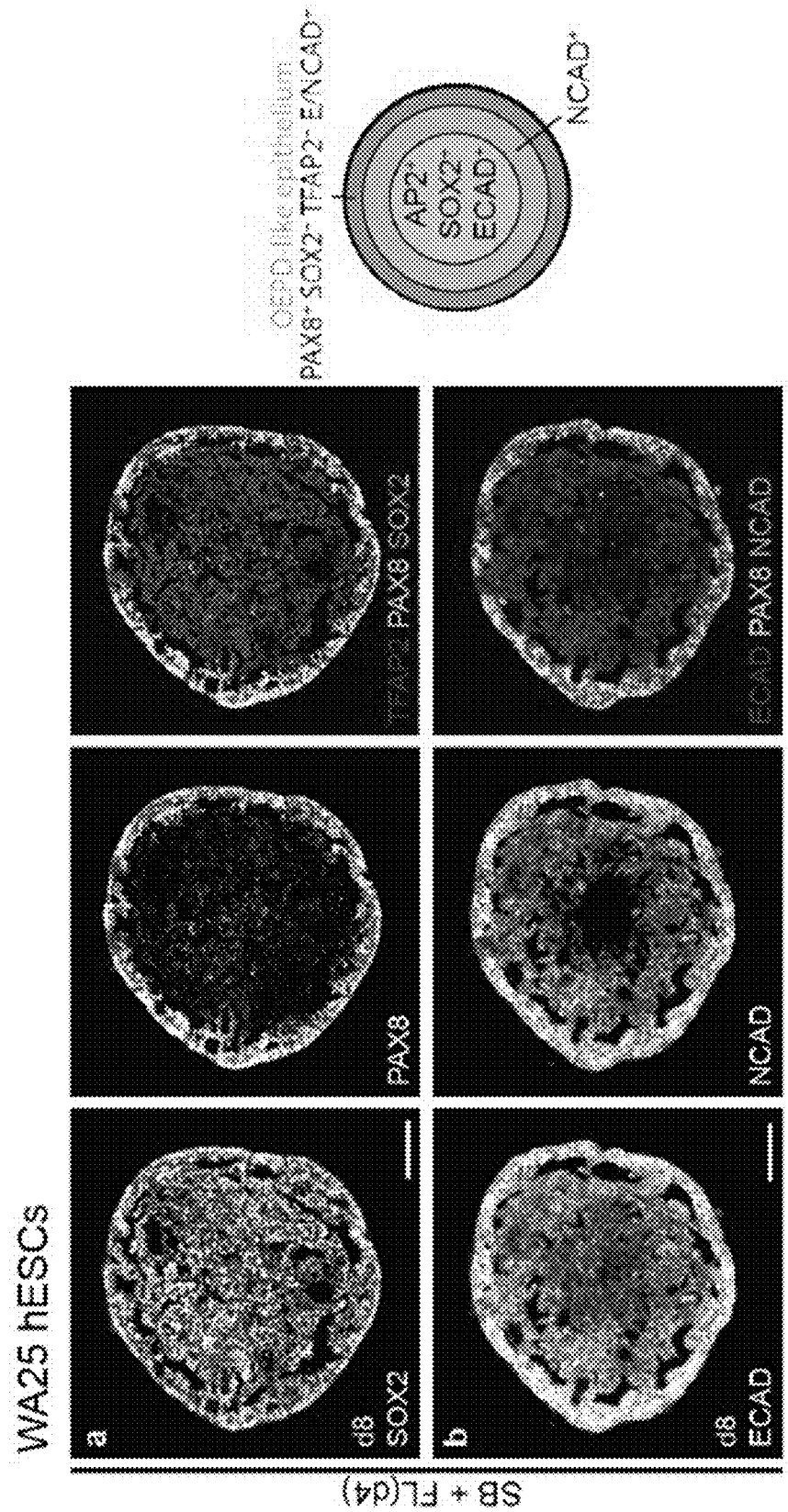
FIGS. 10A-10D demonstrate induction of OEPD-like epithelium in WA25 hESC and mND2-0 iPSC aggregates by FGF-2 and LDN ("FL") treatment. a, b, SOX2, TFAP2, and ECAD are expressed throughout SB-treated WA25 aggregates on day 8 following FL treatment on day 4. PAX8 expression is restricted to the outer-epithelium. A unique characteristic of the epibranchial and otic placodes is the co-expression of ECAD and NCAD. Here, NCAD expression was observed throughout the aggregate, except for the interior-most core. c, d, iPSCs treated with SBB never express PAX8. FL treatment on day 4 induces a thicker outer-epithelium morphology and expression of PAX8. ECAD and TFAP2 are expressed throughout the SBB+FL (d4)-treated iPSC aggregates. Scale bars, 100 μm.
Figures 11A, 11B, 11C, 11D, 11E, 11F:
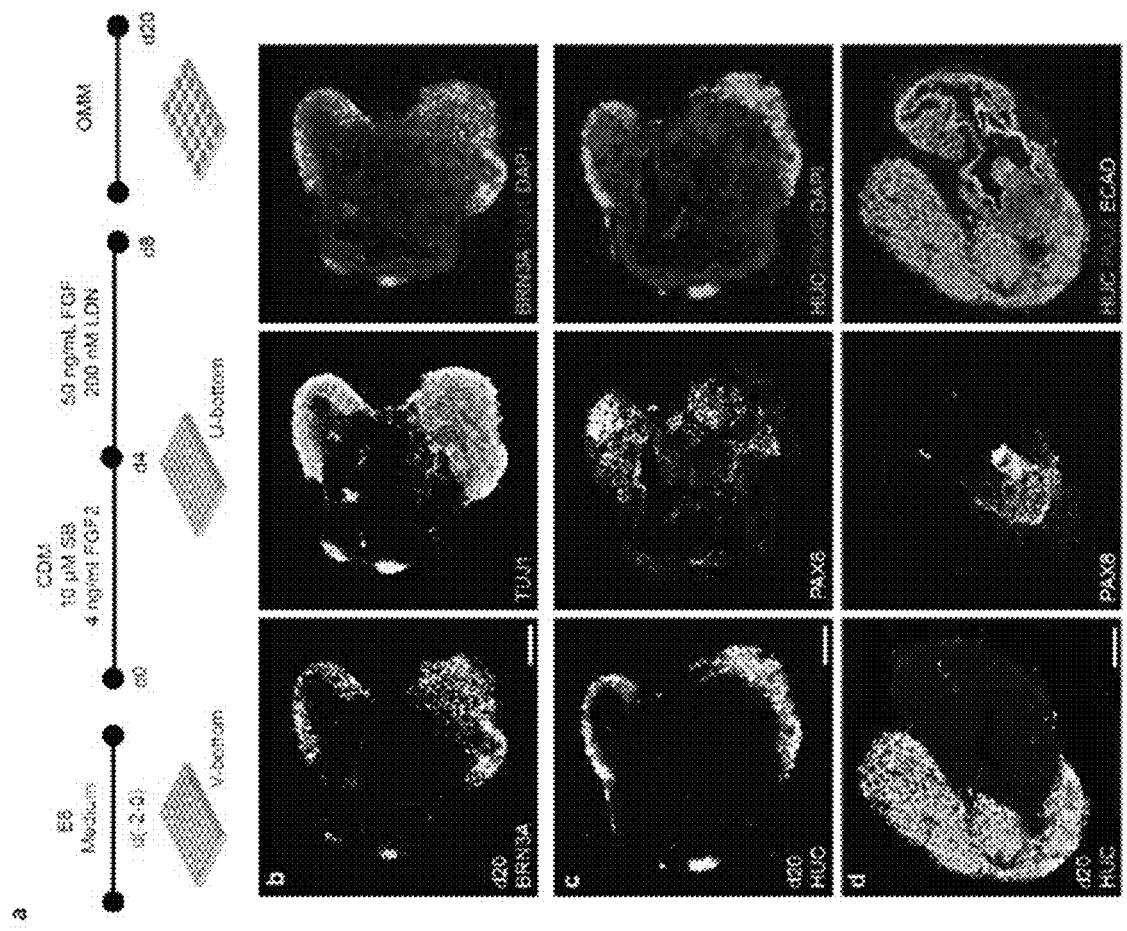
FIGS. 11A-11F demonstrate that OEPD induced aggregates spontaneously generate sensory-like neurons in a minimal medium floating culture. a, Overview of the experiment. SBFL-treated aggregates were transferred to OMM on day 8 of differentiation. b-d, On day 20, the aggregates are composed of patches of BRN3A+ TUJ1+ HUC+ neurons surrounding a ECAD+ epithelium. Neuronal patches were typically associated with PAX8+ epithelium. When aggregates were plated in Matrigel™ droplets they produced neurite outgrowths (e). f, BRN3A+ neurons emerging from a PAX8+ ECAD+ epithelium is consistent with epibranchial placode neurogenesis; however, these data do not directly establish the PAX8+ ECAD+ epithelium as the origin of the sensory neurons. Scale bars, 100 um (b, c, d), 50 μm (e).

Curious whether endogenous BMP activity is sufficient for non-neural specification, we performed a co-treatment with the BMP inhibitor, LDN-193189 (hereafter, LSB; dual LDN/SB treatment referred to as LSB). As previously shown in hESC monolayer cultures[18], LSB treatment to WA25 aggregates up-regulated neuroectoderm markers, such as PAX6 and N-cadherin (NCAD), and abolished TFAP2 and ECAD expression, suggesting that endogenous BMP signals drive non-neural conversion (FIG. 1F; FIGS. 7A-7D). To further validate our approach, we treated human iPSCs (mND2-0, WiCell) with SB and found, contrary to our results with WA25 hESCs, SB-only conditions generated PAX6$^+$ neuroectoderm and TFAP2$^+$ ECAD$^-$ neural crest-like cells (FIGS. 8A-8G). We reasoned that variation in endogenous BMP levels may underlie the different outcomes and the BMP concentration may need to be fine-tuned for each cell line. Accordingly, a low concentration of BMP4 (2.5 ng/ml) in addition to SB (SBB) could generate TFAP2$^+$ ECAD$^+$ non-neural epithelium from mND2-0 iPSCs (FIG. 1G; FIGS. 8A-8G). With either the SB or SBB approaches, the resulting epithelium closely resembled non-epithelia generated with mPSCs[5,6]. In contrast to our mouse culture, non-neural conversion occurs without off-target induction of Brachyury (BRA)$^+$ mesendoderm cells (FIGS. 9A-9C). The following data were generated using either the SB (WA25) or SBB (mND2-0) approaches.

Next, we attempted to convert the non-neural epithelium into otic placode epithelium prior to keratinocyte commitment. Human cranial placodes arise at approximately 18-24 dpc; thus, assuming hPSCs represent cells at ~12 dpc, otic placodes would develop in our culture within the first 6-12 days of differentiation with proper signaling modulation (FIG. 1B). Drawing on our previous finding that FGF activation and BMP inhibition are essential for pre-placode and otic induction from mPSC cultures, we treated day 4 aggregates with a combination of FGF-2 and LDN (hereafter, "SBFL"). With SBFL treatment, the outer-epithelium thickened relative to SB-treated samples and expressed a combination of posterior placode markers, such as PAX8, SOX2, TFAP2, ECAD, and NCAD, indicating a phenotype similar to the otic-epibranchial progenitor domain (OEPD) from which the otic placode arises (FIGS. 1H-1K; FIGS. 10A-10D). When allowed to undergo self-guided differentiation in a minimal medium, we found that SBFL aggregates generated BRN3A$^+$ TUJ1$^+$ sensory-like neurons between days 10-30 (FIGS. 11A-11F). Since both the epibranchial placodes and the otic vesicles produce sensory neurons, we wondered which tissue type had developed. Notably, we did not detect expression of the otic marker PAX2 nor did we observe any vesicles in SBFL-treated aggregates, which would signify otic induction (data not shown). Thus, we concluded that SBFL treatment may be sufficient to induce epibranchial neurons, yet fails to initiate otic induction.

Figures 2A, 2B, 2C, 2D, 2E, 2F, 2G, 2H:
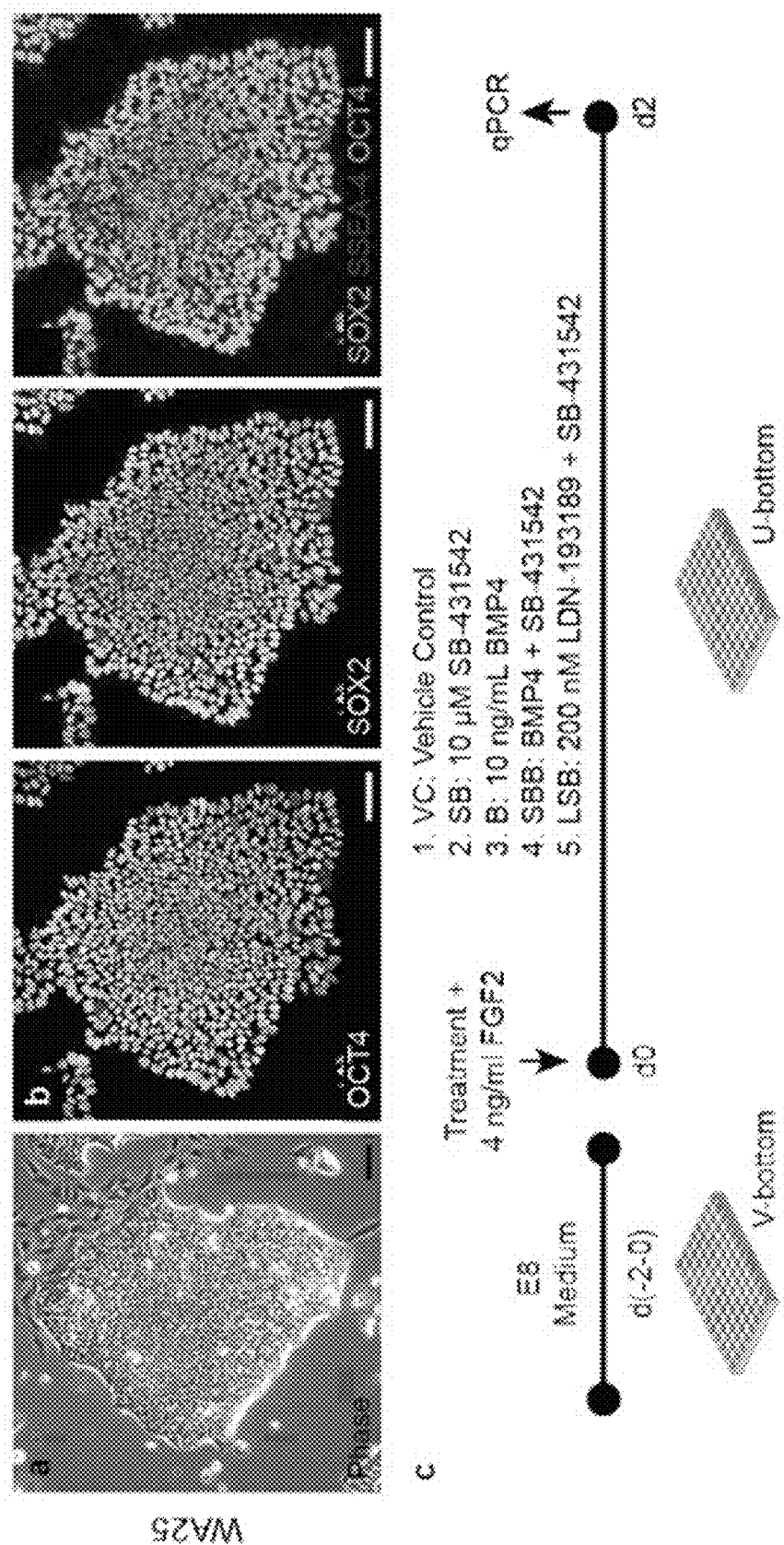
FIGS. 2A-2H demonstrate undifferentiated WA25 hESCs, cell aggregation, and initial non-neural ectoderm differentiation analysis. a, b, WA25 cells maintained on Vitronectin-N-coated plates in E8 medium express markers of primed pluripotent stem cells. c, Overview of differentiation strategy and experimental conditions. d, e, Aggregation of single-celled hESCs in E8+20 µM Y-27632 produced less cellular debris than aggregation in CDM+20 µM Y-27632. f, Relative to undifferentiated cells, pluripotency markers were significantly down-regulated by day 2 in all conditions except vehicle control. g, The non-neural markers TFAP2 and DLX3 were upregulated in SB and SBB conditions. h, The mesendoderm markers BRA and EOMES were upregulated by BMP4 (B) treatment. Gene expression was normalized to d0 aggregates. For statistical tests treatment values were compared to control (CTRL) values; n=3 biological samples, 2 technical replicates; *P<0.05, P<0.01, *P<0.001, ns=not significant; error bars are max/min. Scale bars, 100 µm (a, d, e), 25 µm (b).
Figures 3A, 3B, 3C, 3D, 3E, 3F, 3G:
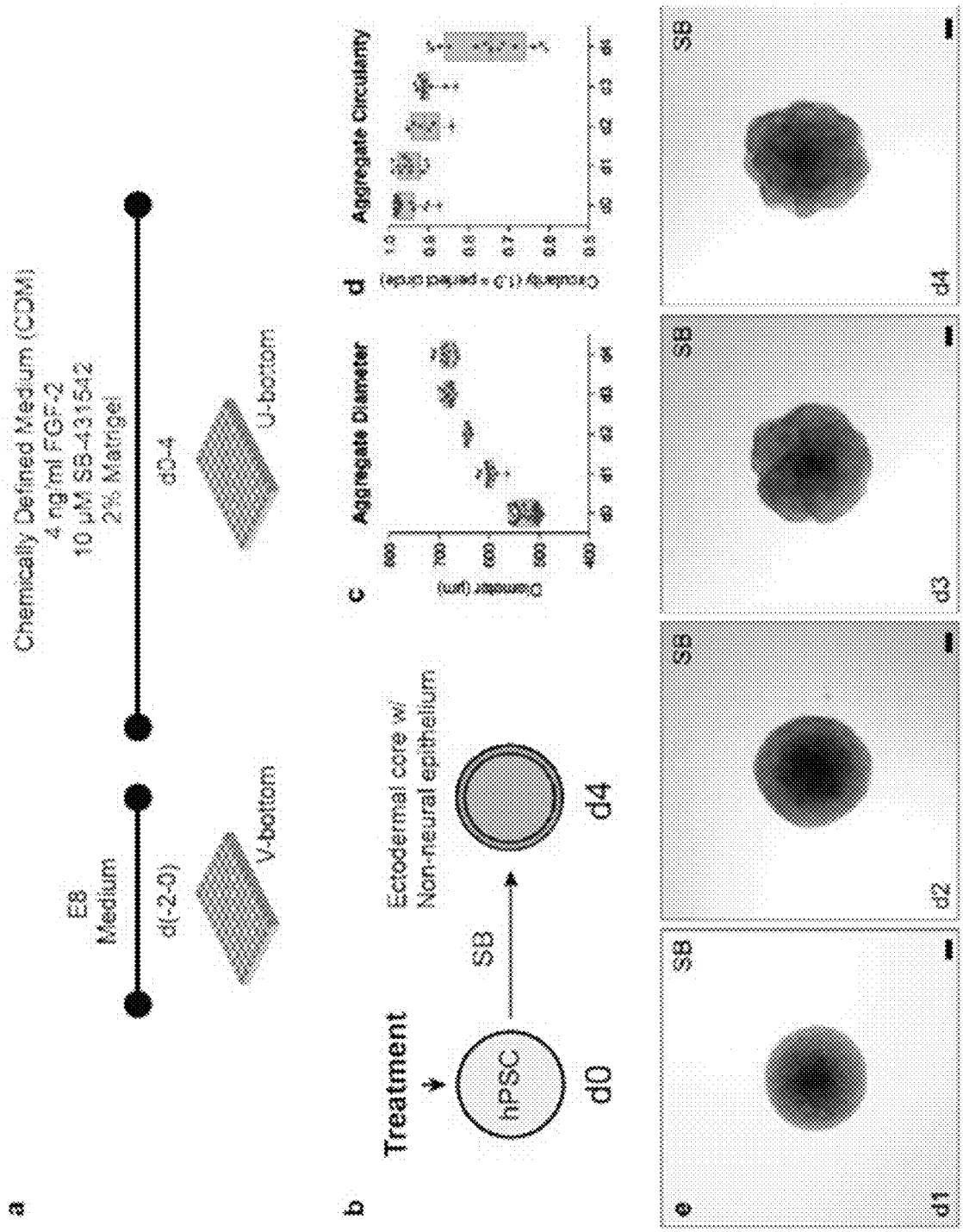
FIGS. 3A-3G demonstrate non-neural induction using WA25 hESCs. a, b, Overview of differentiation strategy. c-e, Aggregate diameter (c) and circularity (d) over time in culture. The circularity of the aggregates decreases overtime as the outer epithelium crumples (e). f, g, Representative day 4 aggregate showing a nearly complete lack of OCT4-expressing cells, SOX2/ECAD-expressing cells in the core, and TFAP2/ECAD-expressing cells in the outer-core and epithelium. Error bars are max/min. Scale bars, 100 µm.
Figures 4A, 4R:
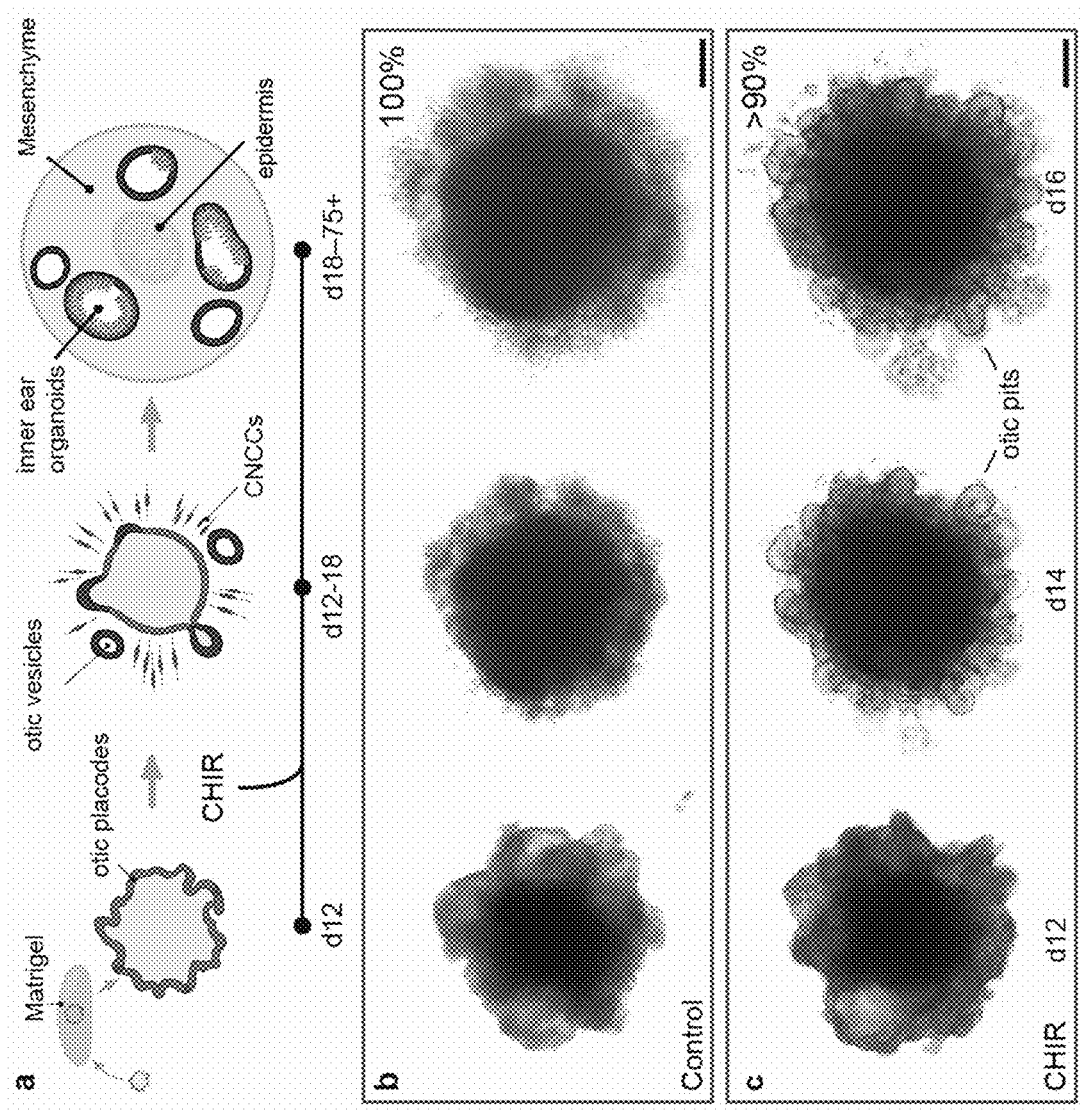
FIGS. 4A-4R demonstrate that Wnt signaling activation initiates self-organization and maturation of inner ear organoids containing vestibular-like hair cells. a, Inner ear organoid induction strategy. Day 12 aggregates were embedded in Matrigel droplets to support vesicle formation. b-d, In CHIR-treated samples, but not DMSO (Control) samples, otic pit-like structures evaginate from the outer-epithelium (d). e-i, Between days 14-35, pits and vesicles expressed otic specific markers, such as SOX10, SOX2, JAG1, PAX8, PAX2, and FBXO2. The epithelium from which vesicles arise begins to express the epidermal keratinocyte marker KRT5 by day 35 (h). j, By day 40-60, the aggregates contain multiple organoids and, typically, a single epidermal unit visible under DIC imaging. Inner ear organoids are distinguishable by a defined epithelium with ~25-40 µm apparent thickness and a lumen (j inset). k, Inner ear organoids are typically oriented around the epidermal unit and contain sensory epithelia with ANXA4$^+$ PCP4$^+$ hair cells. The luminal surface of organoids is actin-rich, as denoted by phalloidin staining (k"). l-o, Hair cells are MYO7A$^+$ SOX2$^+$, and supporting cells are SOX2$^+$. F-actin-rich hair bundles protrude from the hair cells into the lumen (n, o; asterisks denote hair bundle location in m). p, q, mND2-0 iPSC-derived sensory epithelia have a similar morphology to WA25 hESC-derived sensory epithelia and contain PCP4$^+$ ANXA4$^+$ hair cells. SOX10 is expressed throughout the supporting and non-sensory epithelial cell populations, but not in hair cells (p). Supporting cells express the utricle supporting cell marker SPARCL1 (q). r, Hair cells in organoids have ESPN$^+$ hair bundles with a single acetylated-tubulin (TUBA4A)$^+$ kinocilium. Scale bars, 200 µm (j), 100 µm (b, c, e), 50 µm (g, h, k), 25 µm (d, f, l, m, p), 10 µm (n, q), 5 µm (r), 2.5 µm (o).
Figures 12A, 12B, 12C:
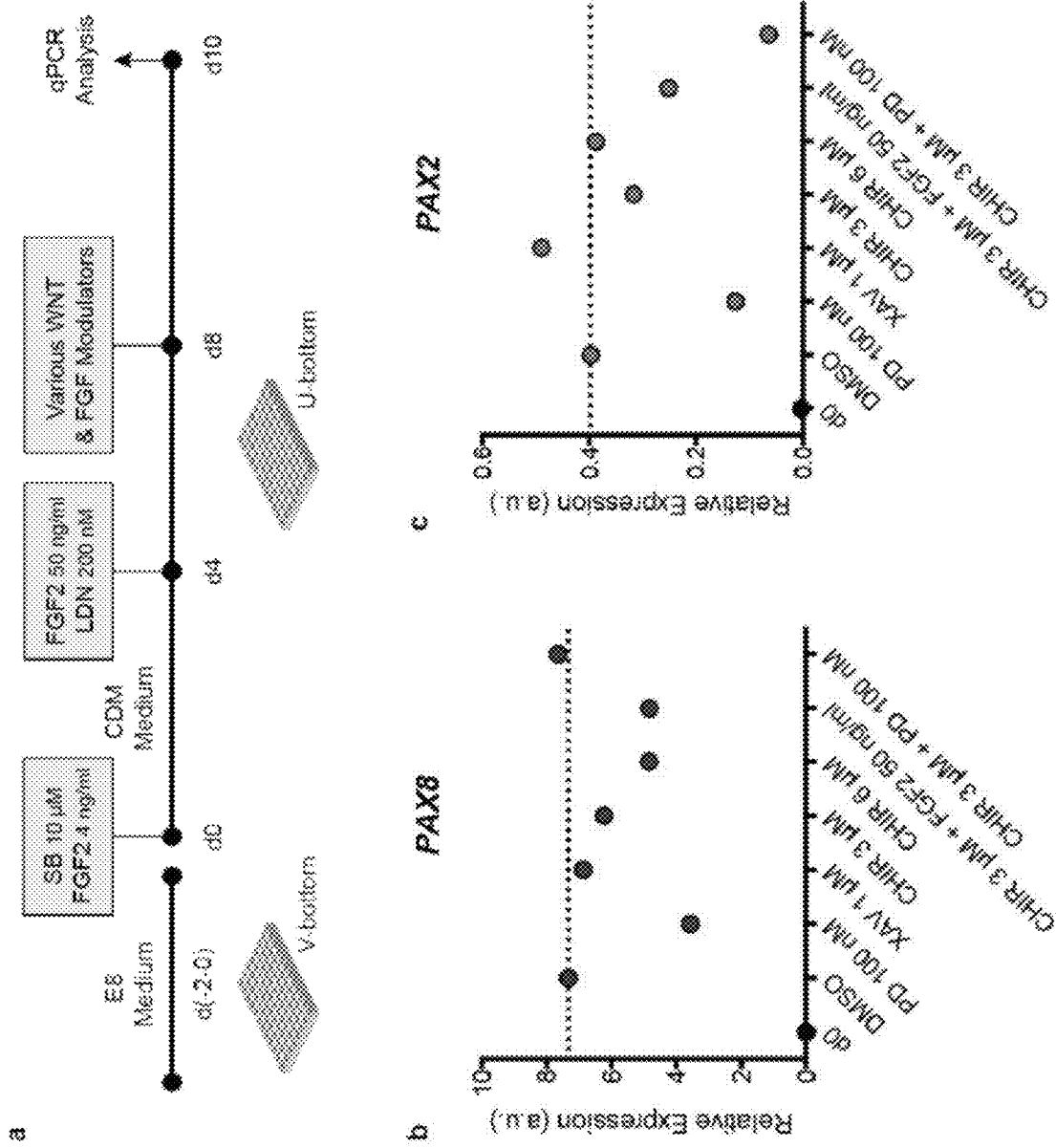
FIGS. 12A-12C demonstrate WNT and FGF signaling modulation and PAX8/PAX2 expression during days 8-10 of differentiation. a, These qPCR data are representative of one exploratory experiment focused on identifying signaling modulators that could increase PAX2 expression following OEPD induction. b, c, FGF inhibition using, PD-173074 likely inhibits PAX2 expression, as would be expected based on developmental studies (Groves et al., Development 139, 245-257 (2012)). By contrast, the WNT inhibitor, XAV939, and WNT agonist, CHIR99021, only had a modest positive or negative impact on PAX2 expression compared to a DMSO controls. Based on these results and extensive immunostaining for PAX2 expression, we reasoned that the OEPD epithelium may require more time before it will be responsive to otic inductive cues. Thus, we changed strategies by lengthening the initial culture phase to 12 days (with addition of fresh media on day 8) and testing the effect of transitioning the aggregates to Matrigel™ droplets.
Figures 13A, 13B, 13C, 13D, 13E, 13F, 13G:
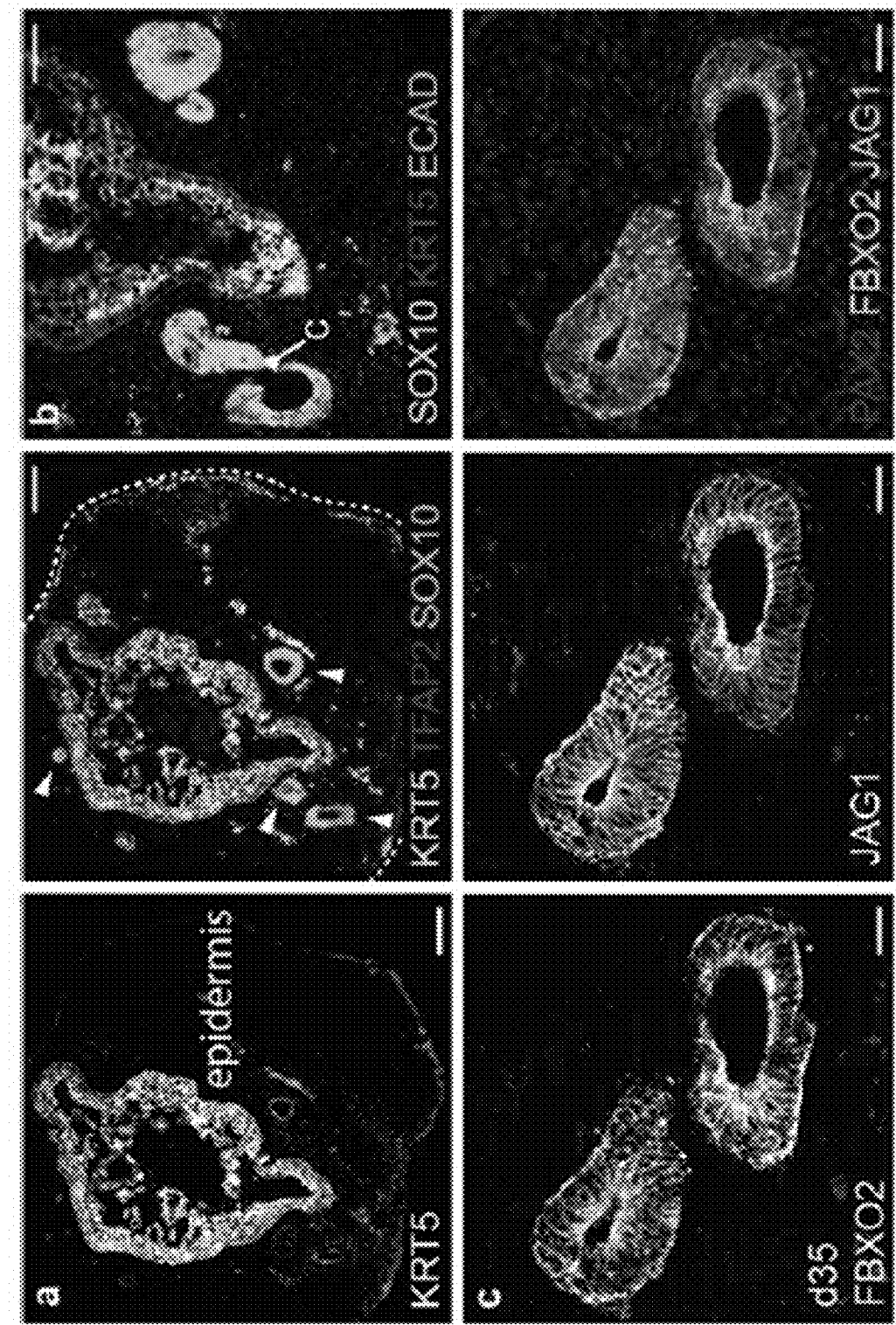
FIGS. 13A-13G demonstrate that otic vesicles evaginate radially around a core epithelium of epidermal keratinocytes. a-c, Serial sections through a day 35 aggregate showing the internal organization of epidermal and otic vesicle epithelia. KRT5 expression is restricted to the epidermis, whereas ECAD is expressed in both epidermis and otic vesicle epithelial cells. Arrowheads label SOX10+ otic vesicles in (a). Note the CNC-like SOX10+ TFAP2− and SOX10+ TFAP2+ cells in the mesenchymal layer of the aggregate. The pair of vesicles highlighted in panel (c) are labeled, at lower magnification and different orientation, in panel (b). The vesicles seen in (c) were shown to co-express the otic vesicle markers SOX10, PAX2, FBXO2, JAG1, and ECAD. d-g, A day 35 aggregate that was wholemount immunostained for ECAD to reveal the epidermal core and surrounding otic vesicles. Scale bars, 250 μm (d, f), 100 μm (a, b), 25 μm (c, g).

To promote PAX2 expression and vesicle formation, we began testing various signaling modulators (FIGS. 12A-12C). Although none of the conditions we tested had a detectable effect on PAX2 gene expression using qPCR analysis, extensive immunostaining drew our attention to a small population of PAX2$^+$ PAX8$^+$ ECAD$^+$ cells in the epithelia of aggregates of control samples on day 12, reminiscent of the otic placodes in vivo (FIGS. 1L-1N). We suspected that extracellular matrix could provide structural support for vesicle formation; thus, we transferred day 12 aggregates to Matrigel droplets in a minimal media (FIG. 4A). In these cultures, we observed radial production of migratory cells, but no vesicle-like structures or PAX2$^+$ cells were apparent (FIG. 2B). Wnt activation seems to be essential for otic, but not epibranchial development, in vivo and can enhance the production of mouse inner ear organoids in vitro[4,19-21]. Remarkably, in 90.9±5.2% of Matrigel®-embedded aggregates treated with a Wnt signaling agonist, CHIR99021, between days 12-16 (n=84, 7 experiments), we witnessed epithelial protrusions reminiscent of the otic pits that precede vesicle development in vivo (FIG. 4C). We determined that the otic pit-like structures were PAX2$^+$ PAX8$^+$ SOX2$^+$ SOX10$^+$ JAG1$^+$, confirming otic identity (FIGS. 4D-4H). Interestingly, the otic pits were accompanied by migrating TFAP2$^+$ SLUG$^+$ SOX10$^+$ cranial neural crest-like cells that formed a mesenchyme around the otic pits, similar to the peri-otic mesenchyme in vivo (FIGS. 4C-4F).

We cultured the aggregates in stationary droplets until day 18, then transferred them to a 24-well plate on an orbital shaker or a spinner flask for further self-organized maturation—both formats produced comparable results. At 20-30 days in culture, vesicles remained visible through the surface of 71.7±23.3% aggregates examined (n=37, 3 experiments; FIGS. 13A-13G). In each aggregate we immunostained, we found multiple otic vesicles surrounding a central core epithelium that expressed the basal keratinocyte markers TFAP2 and KRT5 (FIGS. 4G-4I). As late as day 35, we observed vesicles and otic placode-like epithelia that appeared to be partially attached or incorporated into the epidermal epithelium (FIG. 4H). In addition, older vesicles (>30 days) expressed the transcription factor FBXO2, which was recently shown to be highly specific to developing inner ear epithelia in mice (FIG. 4I)[22].

After 40-60 days of incubation, vesicles with complex multi-chambered morphologies were visible through the aggregate surface (FIG. 4J). Remarkably, we found that a subset of vesicles in both WA25 and mND2-0 derived aggregates developed epithelia containing cells expressing multiple hair cell markers, including MYO7A, PCP4, ANXA4, SOX2, and CALB2 (FIGS. 4K-Q; FIGS. 14A-14E). The sensory-like epithelia also contained SOX2$^+$ SOX10$^+$ SPARCL1$^+$ cells, reminiscent of supporting cells in the mammalian utricle[23]. The luminal cells in these epithelia had elongated morphologies with F-actin-rich apical junctions characteristic of inner ear sensory epithelia (FIGS. 4L-4O). The cells expressing hair cell markers also had F-actin-rich and espin (ESPN)$^+$ apical stereocilia bundles protruding into the vesicle lumen that were associated with an acetylated-alpha-Tubulin (TUBA4A)$^+$ kinocilium (FIGS. 4M-4P, 4R). Together, these findings confirm that the hPSC-derived otic vesicles generate inner ear organoids with sensory epithelia containing hair cells and supporting cells.

Figures 5A, 5B, 5C, 5D, 5E, 5F, 5G, 5H, 5I, 5J, 5K:
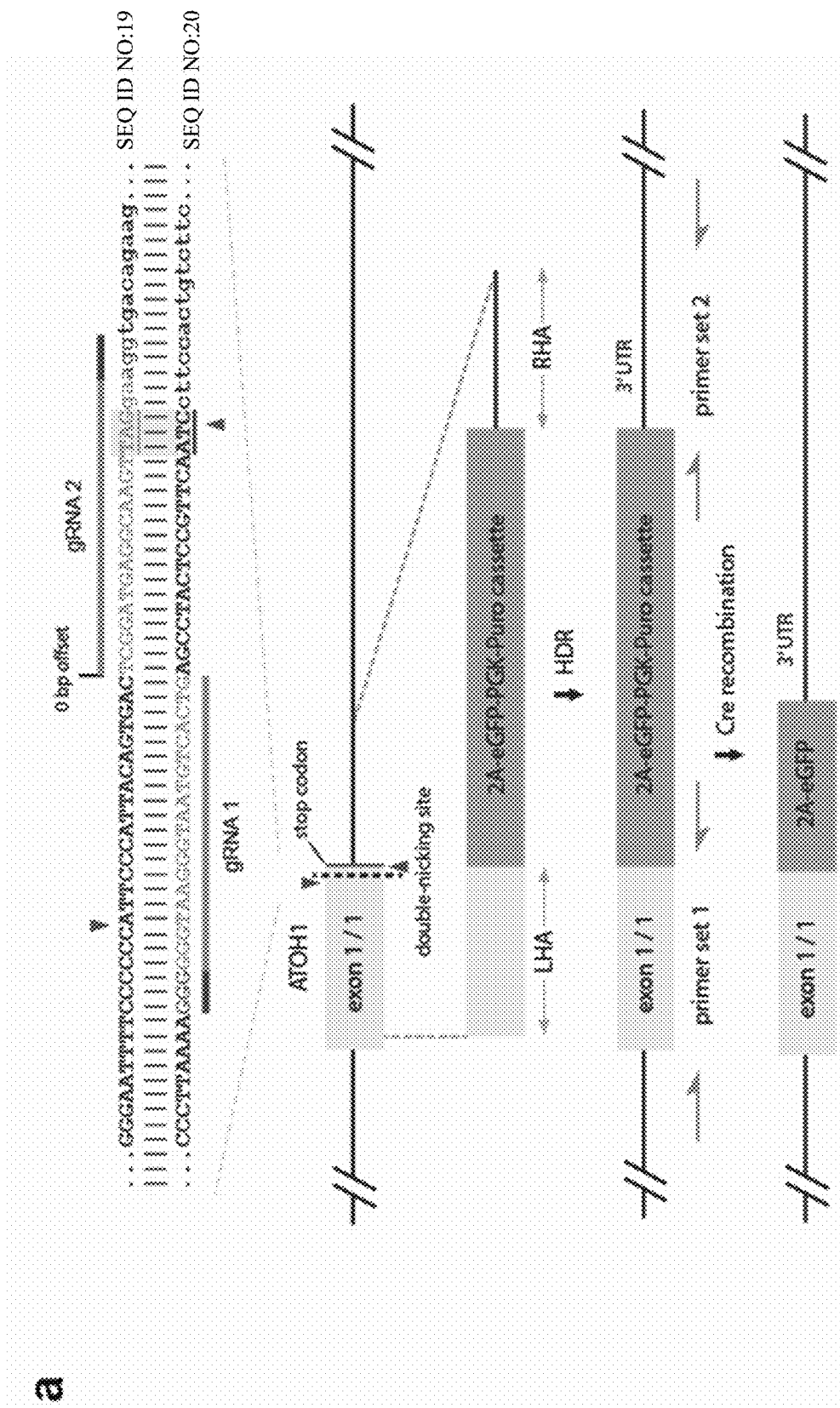
FIGS. 5A-5K demonstrate that hESC-derived hair cells have similar electrophysiological properties to those of native hair cells. a, ATOH1-2A-eGFP CRISPR design. The two guide RNAs (blue, with PAM sequence in red) direct Cas9n to make two nicks (red triangles) near the stop codon (underlined with pink background) of ATOH1. The resulting DNA double strand break is repaired by the donor vector, which has a 2A-eGFP-PGK-Puro cassette and 1 kb left and right homology arms (LHA and RHA). The LoxP-flanked PGK-Puro sub-cassette is subsequently removed by Cre recombinase. In ATOH1 expressing hair cells, eGFP is transcribed along with ATOH1. b-d, Representative live cell images of 2A-eGFP$^+$ hair cells in 50- and 100-day-old inner ear organoids. In panel (b), cartilage nodule (cn) and asterisks denote separate 2A-eGFP$^+$ hair cell patches. The asterisk in panel (c) denotes the approximate location of the hair cells in panel (d). e, Expression of BRN3C in 140-day-old eGFP$^+$ hair cells. f, Expression of ESPN in the hair bundles of 100-day-old eGFP$^+$ hair cells. g, Human organoid hair cells displayed prominent outward currents (d64). h, The cell responded to current injection with rectifying voltage deflections with features similar to those seen in mouse vestibular type II hair cells. i, Human organoid hair cells were able to follow sinusoidal stimuli with an initial peak on the rising phase (excerpt of frequency sweep). j, Although voltage-gated currents were slightly smaller at this point in culture, the gross voltage dependence closely resembled that seen in mouse hair cells (non-leaky recordings pooled for days 64-67, comparison from P4 mouse utricle). k, However, the inward rectifier current, seen below −80 mV in mouse utricular and organoid cells, was not prominent in the human organoid cells. Scale bars, 200 µm (b), 100 µm (c), 25 µm (e), 5 (d, f).
Figures 6A, 6B, 6C, 6D, 6E:
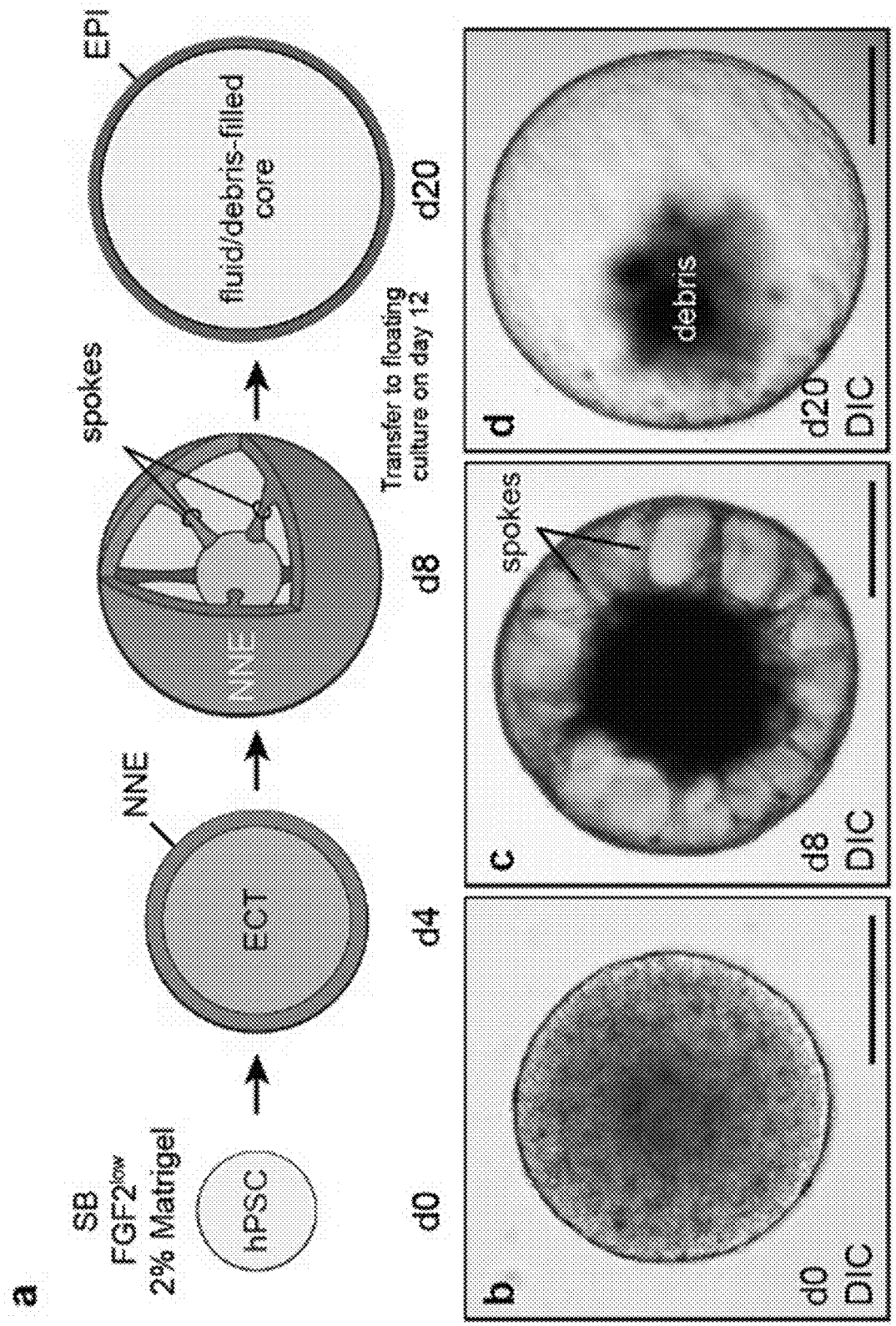
FIGS. 6A-6E demonstrate that SB-treated aggregates generate keratinocytes. a, Overview of non-neural and keratinocyte induction process. b-d, In 3D culture, non-neural ectoderm induction is accompanied by characteristic morphological changes. By days 6-8, the epithelium separates from the core, forming a translucent sphere (c). The epithelium remains connected to the core via spoke-like structures (a, c). After 20 days, spokes from the core are absent, and the epithelial sphere is typically filled with cellular debris (d). e, The day 20 epithelium contains TFAP2+ KRT5+ cells, indicative of epidermal keratinocytes. Scale bars, 250 µm (b-d), 100 µm (e), 5 µm (e').
Figures 7A, 7B, 7C, 7D:
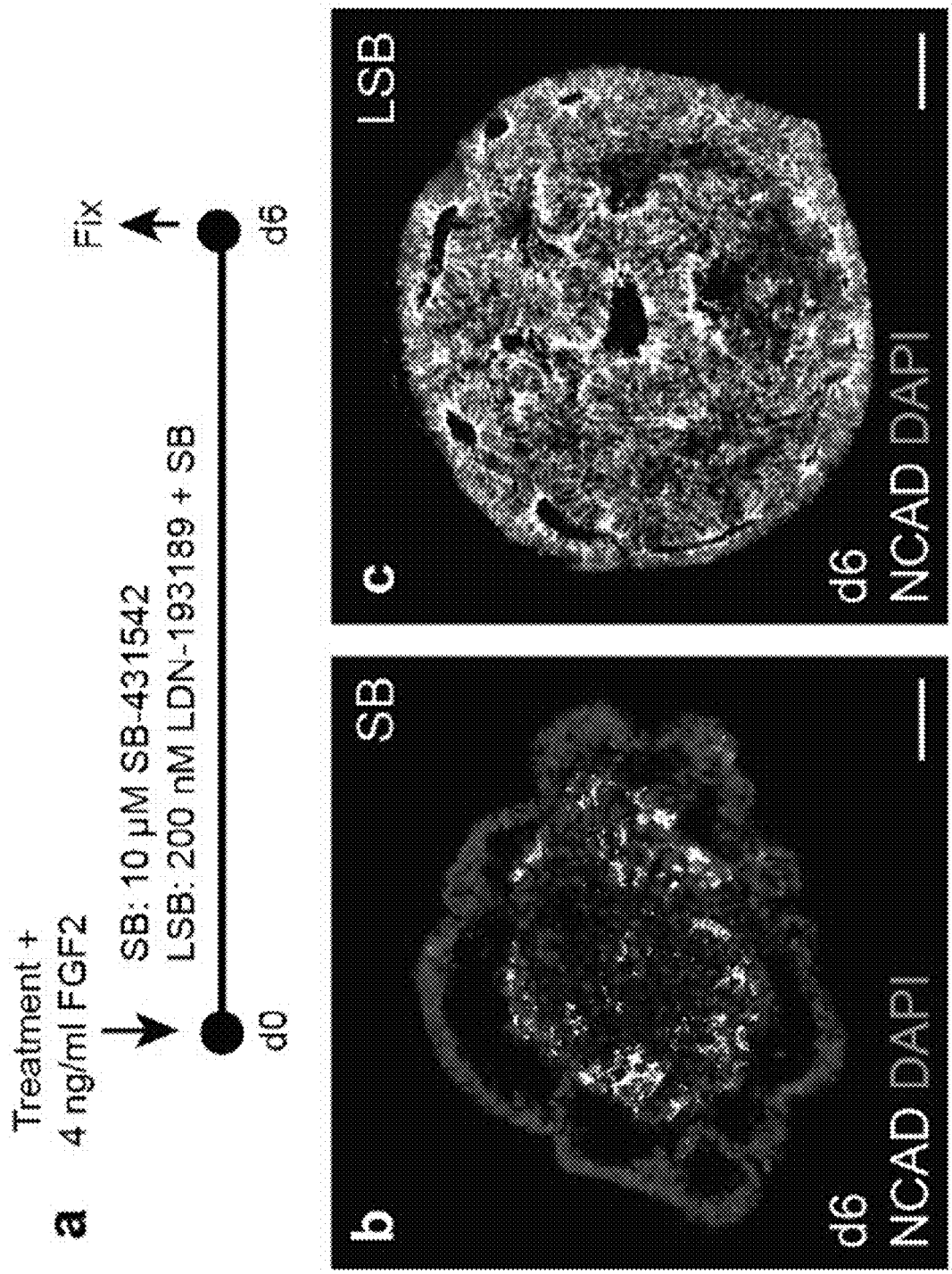
FIGS. 7A-7D demonstrate that non-neural ectoderm induction in SB-treated WA25 aggregates is due to endogenous BMP signaling. a, Overview of experiment to test whether endogenous BMP signaling influence non-neural induction. b-d, LSB treatment leads to NCAD expression throughout the aggregates. Note that a subpopulation of NCAD+ PAX6+ cells (see FIG. 1E) do appear in the core of SB treated aggregates. Scale bars, 50 µm.
Figures 8A, 8B, 8C, 8D, 8E, 8F, 8G:
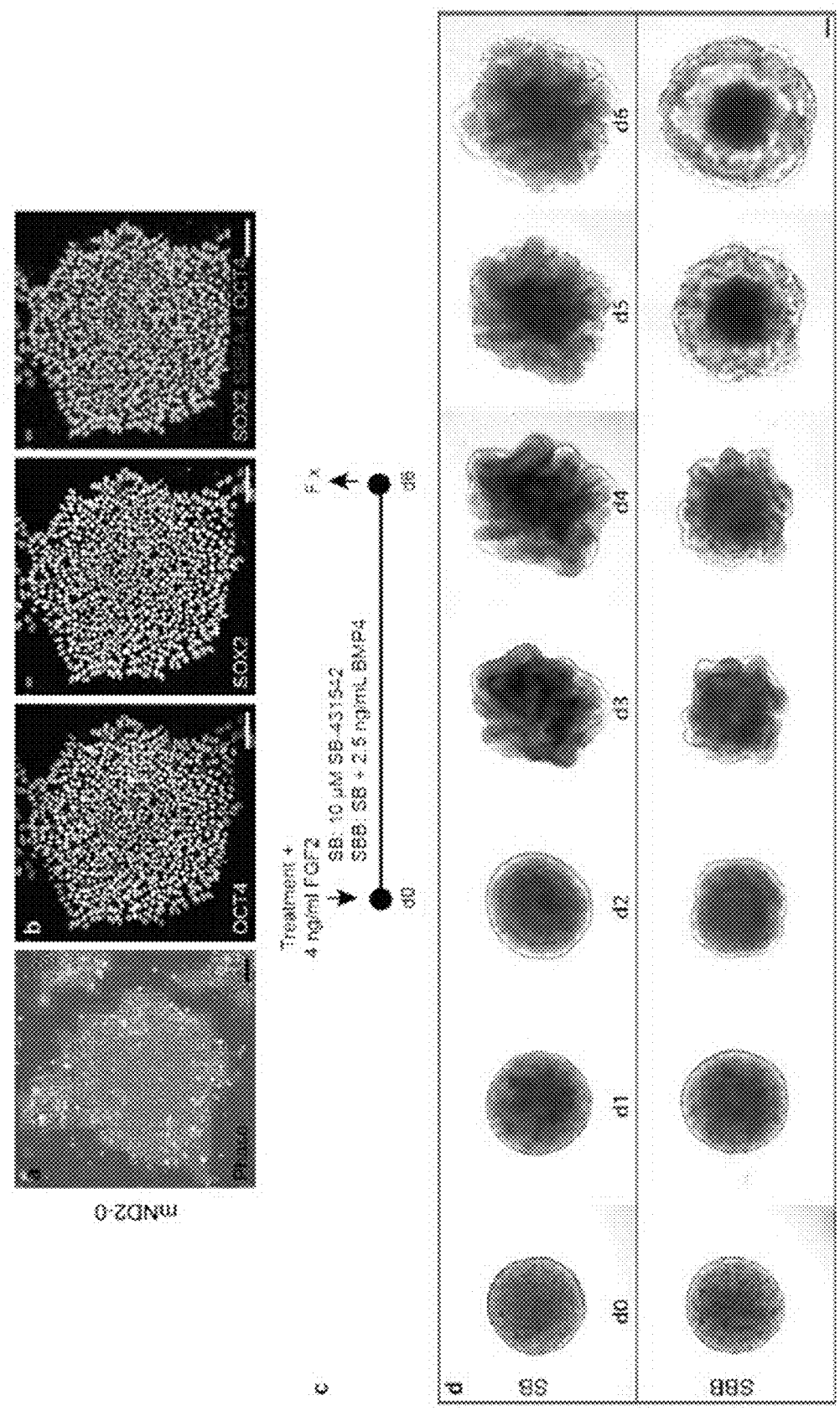
FIGS. 8A-8G demonstrate non-neural ectoderm induction with mND2-0 iPSCs. a, b, WA25 cells maintained on Vitronectin-N-coated plates in E8 medium express markers of primed pluripotent stem cells. c, Overview of differentiation strategy and experimental conditions. Other BMP concentrations were tested in a preliminary experiment (1.25, 2.5, 5, 10, 20, 40 ng/ml), and 2.5 ng/ml was selected as the minimum concentration that produced the morphological changes (i.e., translucent sphere) seen in SB-treated WA25 cells (see FIG. 6C). d, Representative images of SB- or SBB-treated aggregates between days 0-6. e, f, SB-treated aggregates generate PAX6+ NCAD+ epithelia, TFAP2+ migratory cells, and few ECAD+ cells by day 6, suggesting a heterogeneous mix of neuroectoderm and neural crest cells. g, Endogenous BMP signaling is insufficient for non-neural conversion in mND2-0 iPSCs; thus, additional BMP4 is necessary. Scale bars, 100 μm (d), 25 μm (a, b, e, FIGS. 9A-9C demonstrate that non-neural ectoderm induction occurs without off-target induction of mesendodermal cells. Representative Brachyury (BRA) immunohistochemistry in day 4 aggregates treated with 10 ng/ml BMP4 (a), 10 μM SB (b), and 10 μM SB+2.5 ng/ml BMP4 (c) on day 0. Scale bars, 50 μm.
Figures 14A, 14B, 14C, 14D, 14E:
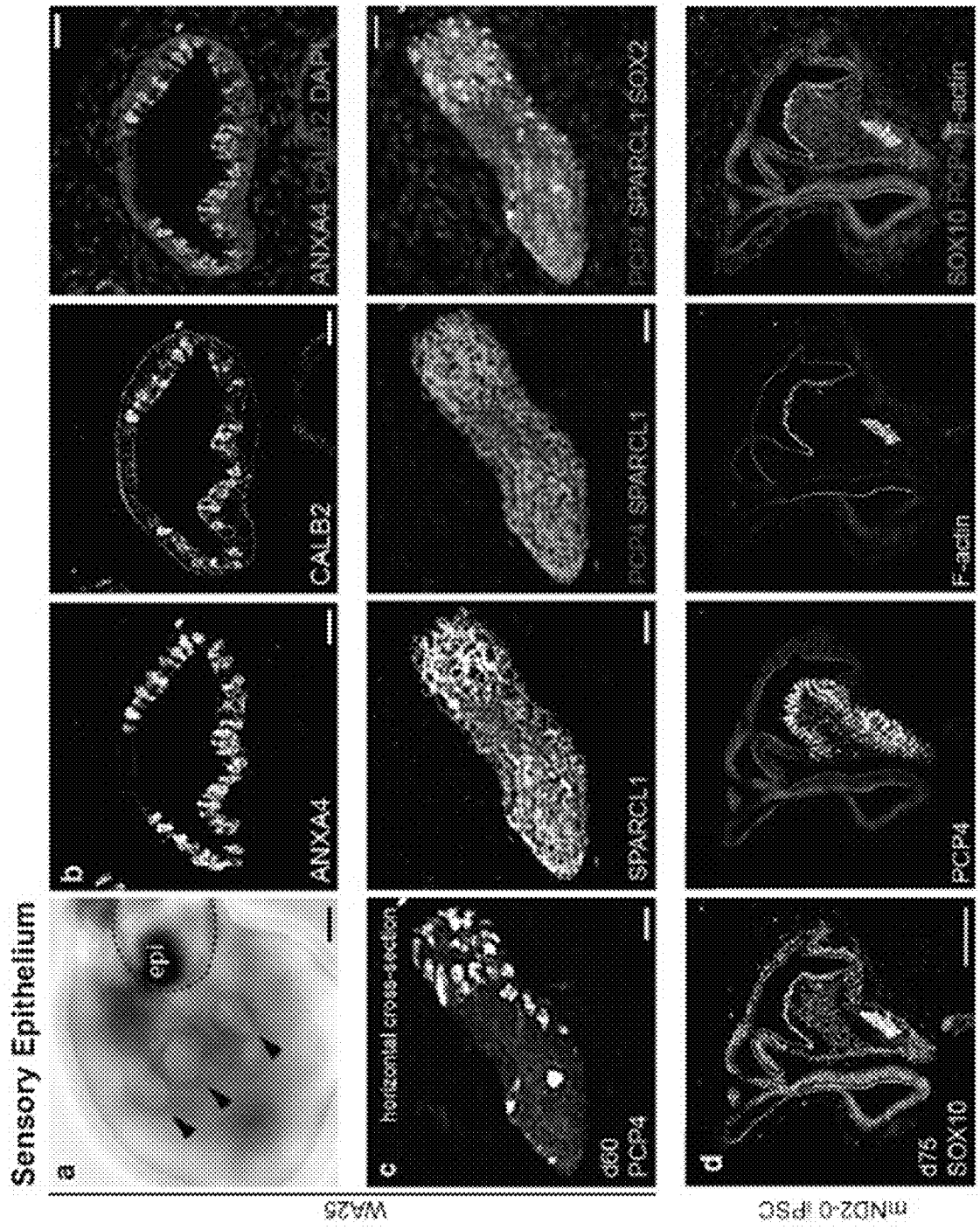
FIGS. 14A-14E demonstrate that inner ear organoids generate vestibular-like sensory epithelia. a, Day 48 aggregate with three visible inner ear organoids (arrowheads). Note that this specimen was derived from a separate experiment than the specimen seen in FIG. 2J. b, Organoid hair cells express the type II vestibular and inner cochlear hair cell marker CALB2. c, Cross-section through a sensory epithelium showing expression of SPARCL1 throughout the supporting cells. SOX2 is expressing in both supporting cells and PCP4+ hair cells. d-f, SOX10 is expressed throughout the supporting and non-sensory epithelial cells. F-actin-rich circumferential belts were observed in both sensory and nonsensory epithelial. Scale bars, 100 μm (a, d, e), 25 μm (b, c), 10 μm (f).

To facilitate live-cell imaging and electrophysiological experiments, we engineered a novel hESC reporter cell line to endogenously label hair cells with enhanced green fluorescent protein (eGFP). We used the CRISPR/Cas9 system to insert a 2A-eGFP gene cassette at the stop codon of the ATOH1 gene, which is highly expressed during hair cell induction and early maturation (FIG. 5A)[7]. We verified inner ear organoid induction from two clones containing the proper bi-allelic insertion of the 2A-eGFP cassette using our established protocol (hereafter ATOH1-2A-eGFP cells). Remarkably, as early as day 39, we observed eGFP$^+$ hair cell-like cells emerging in inner ear organoids (data not shown). We noted that the individual organoids often contained multiple discrete patches with hundreds of eGFP$^+$ cells (FIGS. 5B-5D). Immunostaining with hair cell markers, such as BRN3C and ESPN, confirmed the hair cell identity of eGFP$^+$ cells (FIGS. 5E, 5F). Between days 60-100, 17.4±4.0% of aggregates contained at least one hair cell bearing organoid (n=146, 6 experiments). The seemingly low efficiency of hair cell induction may be due to our inability to detect organoids deep within the aggregates or it could indicate that the endogenous signals required for sensory epithelia formation vary from aggregate-to-aggregate. Notably, all WA25 and mND2-0 aggregates examined between days 60-100 contained organoids with SOX10$^+$ non-sensory epithelia, suggesting that organoid induction may be highly reproducible, but non-sensory inner ear epithelia are preferentially induced (n=17, 4 experiments; FIG. 14E). The 2A-eGFP$^+$ hair cells that develop could be maintained for over 150 days in floating culture and retain hair bundle morphology even after dissection and sub-culturing (FIGS. 5B-F).

Finally, we wondered whether the derived hair cells functioned similar to native mammalian hair cells. Using aggregates produced from ATOH1-2A-eGFP cells, we dissected and flat-mounted inner ear organoids between differentiation days 63-67. To our knowledge, these constitute the first recordings of human hair cells derived from hPSCs. The cells had large outwardly-rectifying currents, but no Na$^+$ current (seen in developing rodent hair cells, but absent in most mature hair cells) was detected in our sample (FIGS. 5G, 5J). The K$^+$ current amplitudes at nominal 100 mV were as follows: day 63: 399, 747, 340 pA; day 64: 4695, 2538, 2609 pA; day 67: 5198, 6528, 6127 pA. This is comparable to the average of 6099 pA for day 22 mouse organoid hair cells. Responses to step and sinusoidal current injection (FIGS. 5H, 5I) resembled that of rodent hair cells, with an initial peak then repolarization, and larger deflections to hyperpolarizing than depolarizing current. However, resting potential of the cells was consistently slightly higher than that seen in rodents: day 64: −43, −45; day 67: −48, −49 mV. Possibly relatedly, the prominent sub-threshold inward rectifier current thought to be carried by Kir2.1 that develops early in hair cell differentiation and is present in all rodent vestibular hair cells and mouse organoid hair cells was absent or greatly reduced in human organoid cells (FIG. 5K)[24,25]. It is possible that development, expression, function, or modulation of Kir2.1 is different in human tissue. Importantly, the constricted lumen morphology seen in most >60-days-old organoids and in all of the organoids used for recording, made direct access to the hair bundles for mechanotransduction analysis challenging (FIGS. 5B-5E). Nonetheless, our data strongly suggest that the human organoids, like mouse inner ear organoids[25], contain immature vestibular hair cells.

In conclusion, we have established a robust culture system for guiding the development of human inner ear organoids in culture (FIG. 15). Our findings further support our previous model of in vitro pre-otic induction and underscore the importance of Wnt signaling in otic progenitor differentiation. Interestingly, the resulting convoluted and multi-chambered morphology of human inner ear organoids bear a remarkable resemblance to the inner ear's membranous labyrinth, which consists of a series of tubes and chambers containing sensory and non-sensory epithelia. In addition, much like mouse organoids, the hPSC-derived organoids appear to form only vestibular sensory epithelia by default; thus, additional signaling manipulation will be needed to initiate cochlear organogenesis[6,25]. We expect that this culture system will be a powerful tool for uncovering mechanisms of human inner ear development and testing potential inner ear therapies.

Methods and Materials hPSC culture: Human PSCs (WA25 hESCs, passage 22-50; mND2-0 iPSCs, passage 28-46) were cultured in Essential 8 (E8) Medium or Essential 8 Flex Medium (E8f) (Invitrogen) supplemented with 100 μg/ml Normocin (Invivogen) on recombinant human Vitronectin-N (Invitrogen)-coated 6-well plates according to an established protocol[12, 13]. At 80% confluency or every 4-5 days, the cells were passaged at a split ratio of 1:10-1:20 using an EDTA solution. Both cell lines were acquired from the WiCell Research Institute and arrived with a statement of verification and authenticity. Additional validation and testing information can be found on the cell line webpages, available at wicell.org/home/stem-cell-lines/catalog-of-stem-cell-lines/wa25.cmsx and wicell.org/home/stem-cell-lines/catalog-of-stem-cell-lines/mirjt7i-mnd2-0.cmsx on the World Wide Web. Cell lines were determined to be mycoplasma contamination-free using the MycoAlert Mycoplasma Detection Kit (Lonza).

hPSC differentiation. To start differentiation, hPSC cells were dissociated with StemPro Accutase (Invitrogen) and distributed, 5,000 cells per well, onto 96-well V-bottom plates in E8 medium containing 20 μM Y-27632 (Stemgent) and Normocin. Following a 48 hour incubation, the aggregates were transferred to 96-well U-bottom plates in 100 μl of Chemically Defined Medium (CDM) containing 4 ng ml$^{-1}$ FGF-2 (Peprotech), 10 μM SB-431542 (Stemgent), and, for some experiments, 2.5 ng ml$^{-1}$ BMP4 (Stemgent), and 2% Growth Factor Reduced (GFR) Matrigel (Corning) to initiate non-neural induction—i.e. differentiation day 0. CDM contained a 50:50 mixture of F-12 Nutrient Mixture with GlutaMAX (Gibco) and Iscove's Modified Dulbecco's Medium with GlutaMAX (IMDM; Gibco) additionally supplemented with 0.5% Bovine Serum Albumin (BSA), 1× Chemically Defined Lipid Concentrate (Invitrogen), 7 ml$^{-1}$ Insulin (Sigma), 15 μg ml$^{-1}$ Transferrin (Sigma), 450 μM Mono-Thioglycerol, and Normocin (see Table 1 for a detailed formulation). After 4 days of incubation, 25 μl of CDM containing a 250 ng ml$^{-1}$ FGF-2 (50 ng/ml final concentration) and 1 μM LDN-193189 (200 nM final concentration) was added to the pre-existing 100 μl of media in each well. After an additional 4 days (8 days total), 25 μl of CDM was added to the media. For some experiments, CDM containing a 18 μM CHIR99021 (3 μM final concentration; Stemgent) was added to the pre-existing 125 μl of media in each well—we determined that this treatment is optional for inner ear organoid production, but may improve induction of otic placode-like cells. On differentiation day 12, the aggregates were pooled together and washed with freshly prepared Organoid Maturation Medium (OMNI) containing a 50:50 mixture of Advanced DMEM:F12 (Gibco) and Neurobasal Medium (Gibco) supplemented with 0.5× N2 Supplement (Gibco), 0.5× B27 without Vitamin A (Gibco), 1× GlutaMAX (Gibco), 0.1 mM ß-Mercaptoethanol (Gibco), and Normocin (see Table 3 for a detailed formulation).

TABLE 3

Organoid Maturation Medium (OMM)

| Component | Supplier | Cat. No. | Stock Concentration | Final Concentration | Volume (50 ml) |
|---|---|---|---|---|---|
| Adv DMEM/F12 | Gibco | 12491-015 | — | 49% (v/v) | 24.5 ml |
| Neurobasal | Gibco | 21103-049 | — | 49% (v/v) | 24.5 ml |
| N2 supplement | Gibco | 17502-048 | 100X | 0.5X | 250 µl |
| B27-Vitamin A | Gibco | 12587-010 | 50X | 0.5X | 500 µl |
| GlutaMAX | Gibco | 35050-079 | 100X | 1X | 500 µl |
| Mercaptoethanol | Gibco | 21985-015 | 55 mM | 0.1 mM | 91 µl |
| Normocin | Invitrogen | Ant-nr-1 | 50 mg/ml | 100 µg/ml | 100 µl |

The formulation set forth in Table 3 provides for 50 mL of medium, which should be used for <2 weeks. OMNI is a custom-made hybrid of two media previously used to generate cerebral and gastric organoids[6,7]. B27 without Vitamin A was used to limit the influence of endogenously produced retinoic acid.

The aggregates were resuspended in ice cold undiluted GFR Matrigel and placed in approximately 25 µl droplets on the surface of a 100 mm bacterial culture plate. After at least 30 minutes of incubation at 37° C., the droplets were bathed in 10 ml of OMNI containing 3 µM CHIR99021. For non-droplet otic induction, the aggregates were washed and plated individually into each well of a 24-well low cell adhesion plate in OMNI containing 3 µM CHIR and 1% GFR Matrigel. After 18 days of differentiation, the CHIR was removed from the medium by washing and the droplet aggregates were moved to a floating culture. Droplets were carefully dislodged using a wide-mouth 1000P tip and transferred to 75 ml of fresh OMNI in a 125 ml disposable spinner flask (Corning). Spinner flasks were maintained on an in-incubator stir plate (Thermo Scientific) at 65 RPM for up to 180 days of differentiation. For some experiments, the aggregates were maintained in individual wells of 24-well low-cell adhesion plates in 1 ml of OMM on an in-incubator orbital shaker (Thermo Scientific) for up to 140 days.

Choice of Media Components: We used two media components that may lead to variability in results due to lack of definition or poor compatibility with human cells: GFR Matrigel and BSA. GFR (Growth Factor Reduced) Matrigel contains, <0.1 pg ml$^{-1}$ FGF-2, <0.5 ng ml$^{-1}$ EGF, 5 ng ml$^{-1}$ IGF-1, <5 pg ml$^{-1}$ PDGF, <0.2 ng ml$^{-1}$ NGF, and 1.7 ng ml$^{-1}$ TGFβ. In particular, the TGFβ in GFR Matrigel may have impacted cell fate specification on day 12 or later because we did not include a TGFβ inhibitor in the media during that phase of culture. GFR Matrigel was chosen because it has been shown to be a reliable inducer of self-organizing epithelia from pluripotent stem cells in 3D culture[26]. GFR Matrigel is a more defined alternative to Matrigel, in which the concentration of growth factors, such as Egf, Igf1, Fgf2, and TGFβ, have been minimized to levels that should have a negligible effect on cell fate specification. In Other alternatives to Matrigel include, without limitation, synthetic hydrogels and recombinant protein-based matrices that support basement membrane formation and self-organization of differentiating PSCs into epithelia. For example, a purified Laminin/Entactin complex (Corning) may be a suitable, fully chemically defined alternative[27]. In the CDM, BSA was chosen as a cost-effective and easy to dissolve alternative to Human Serum Albumin and Polyvinyl Alcohol (PVA), respectively. PVA has been shown to be a suitable chemically defined substitute for BSA in CDM[28].

Signaling molecules and recombinant proteins. The following small molecules and recombinant proteins were used: recombinant human BMP4 (2.5-10 ng ml$^{-1}$; Stemgent), human FGF-2 (25 ng ml$^{-1}$; Peprotech), SB-431542 (10 µM; Tocris Bioscience), CHIR99021 (3 µM; Stemgent), and LDN-193189 (200 nM; Stemgent).

Quantitative PCR. Analysis was performed as previously described on an ABI PRISM 7900HT Sequence Detection System (Applied Biosystems) or a Bio-Rad CFX96 quantitative PCR machine (Bio-Rad)[6]. Data were normalized to L27 expression (internal control) and the fold change was calculated relative to Ct values from d0 WA25 aggregates using the ΔΔCt method. Unless stated otherwise, data represent at least 3 separate biological samples from separate experiments. All indicators of statistical significance refer to comparisons between a given condition and the control group. Refer to Table 4 for primer details.

TABLE 4 qPCR Primers

| Gene | Sequence | Rationale |
|---|---|---|
| L27 Forward | CGTGAAGAACATTGATGATGGC (SEQ ID NO: 1) | Housekeeping |
| Reverse | GCGATCTTCTTCTTGCCCAT (SEQ ID NO: 2) | |
| DLX3 Forward | TACTCGCCCAAGTCGGAATA (SEQ ID NO: 3) | Non-neural Ectoderm |
| Reverse | TTCTTGGGCTTCCCATTCAC (SEQ ID NO: 4) | |
| TFAP2 Forward | TTTCAGCCATGGACCGTCA (SEQ ID NO: 5) | Non-neural Ectoderm |
| Reverse | GGGAGATTGACCTACAGTGC (SEQ ID NO: 6) | |
| CDX2 Forward | GGGCTCTCTGAGAGGCAGGT (SEQ ID NO: 7) | Extraembryonic |

TABLE 4-continued qPCR Primers

| Gene | Sequence | Rationale |
|---|---|---|
| Reverse | CCTTTGCTCTGCGGTTCTG (SEQ ID NO: 8) | |
| BRA Forward | TGCTTCCCTGAGACCCAGTT (SEQ ID NO: 9) | Mesendoderm |
| Reverse | GATCACTTCTTTCCTTTGCATCAAG (SEQ ID NO: 10) | |
| OCT4 Forward | AGTGAGAGGCAACCTGGAGA (SEQ ID NO: 11) | Pluripotency |
| Reverse | ACACTCGGACCACATCCTTC (SEQ ID NO: 12) | |
| NANOG Forward | CATGAGTGTGGATCCAGCTTG (SEQ ID NO: 13) | Pluripotency |
| Reverse | CCTGAATAAGCAGATCCATGG (SEQ ID NO: 14) | |
| EOMES Forward | CAACATAAACGGACTCAATCCCA (SEQ ID NO: 15) | Mesendoderm |
| Reverse | ACCACCTCTACGAACACATTGT (SEQ ID NO: 16) | |

Immunohistochemistry. Aggregates were fixed with 4% paraformaldehyde for 20 min at room temperature or at 4° C. overnight. The fixed specimens were cryoprotected with a graded treatment of 15% and 30% sucrose and then embedded in tissue freezing medium. Frozen tissue blocks were sectioned into 12 μm cryosections on a Leica CM-1860 cryostat. For immunostaining, a 10% goat or horse serum in 0.1% Triton X-100 1×PBS solution was used for blocking, and a 3% goat or horse serum in 0.1% Triton X-100 1×PBS solution was used for primary/secondary antibody incubations. Alexa Fluor conjugated anti-mouse, rabbit, or goat IgG (Invitrogen) were used as secondary antibodies. Prolong Gold with DAPI (Thermo Scientific) was used to mount the samples and visualize cellular nuclei. For wholemount staining, a similar staining paradigm was used; however, the Triton X-100 concentration was increased to 0.5%, and the blocking and primary/secondary incubations were done at 37° C. on a rotating shaker for 24 hours and 48 hours, respectively. Following each incubation, the samples were subjected to three 1-hour washes in 1×PBS containing 0.5% Triton X-100 at 37° C. on a rotating shaker. Wholemount samples were mounted in ScaleA2 clearing solution for 1-2 days or ScaleSQ(5) clearing solution for 1-2 hours prior to imaging[29]. Microscopy was performed on a Lieca DMi8 inverted microscope, a Nikon TE2000 inverted microscope, or an Olympus FV1000-MPE Confocal/Multiphoton Microscope. 3D reconstruction was performed using the Imaris 8 software package (Bitplane) housed at the Indiana Center for Biological Microscopy. For segmentation analysis, 2A-eGFP cells were processed using the 'Spots' module in Imaris. Classification was based on estimated size, quality and signal intensity. Objects touching the border of the image were excluded. The following build parameters were used to identify 2A-eGFP+ cell bodies: estimated XY diameter=3.50 μm; estimated Z diameter=7.00 μm; 'Quality' above 20.0; 'distance to image border XYZ' above 0.001 μm; 'intensity center Ch=1' above 1,500. Movies were generated in Imaris from the raw image files and compiled in Adobe Premiere Pro to add titles and text. See Table 5 for a list of antibodies.

TABLE 5

Antibodies

| Antibody No. | Host | Supplier | Catalog | Dilution |
|---|---|---|---|---|
| N-Cadherin | Mouse | BD Biosciences | 610920 | 1:100 |
| SOX10 | Mouse | eBiosciences | 14-5923-82 | 1:50 |
| E-Cadherin | Mouse | BD Biosciences | 610181 | 1:250 |
| TFAP2 | Mouse | DSHB | 3B5 | 1:5 |
| SOX2 | Mouse | BD Biosciences | 561469 | 1:100 |
| PAX8 | Rabbit | Abcam | AB97477 | 1:100 |
| PAX2 | Rabbit | Invitrogen | 716000 | 1:100 |
| Jagged-1 (JAG1) | Rabbit | LSBio | LSC138530 | 1:50 |
| BRN3C | Mouse | Santa Cruz | SC81980 | 1:25 |
| BRN3A | Mouse | Millipore | AB5945 | 1:50 |
| MYO7A | Rabbit | Proteus | 256790 | 1:100 |
| Acetylated-α-Tubulin (TUBA4A) | Mouse | Sigma | T6793 | 1:100 |
| bIII-Tubulin (TuJ1) | Mouse | Covance | MMS-435P | 1:500 |
| Calretinin (CALB2) | Mouse | Abcam | AB702 | 1:100 |
| SPARCL1 | Mouse | R&D Systems | AF2728-SP | 1:100 |
| PAX6 | Mouse | DSHB | PAX6 | 1:5 |
| ANXA4 | Mouse | R&D Systems | AF4146 | 1:50 |
| PCP4 | Rabbit | Sana Cruz | SC74816 | 1:50 |
| espin (ESPN) | Rabbit | Gift from James Bartles | Not applicable | 1:50 |

Electrophysiological recordings. Human organoids were shipped at day 62 in cold Hibernate A medium supplemented with 1× GlutaMax, 1× B27 Supplement, and Normocin. They were replaced back into OMNI on day 63 in an incubator at 5% $CO_2$ and 37° C. On recording days, organoids were dissected out using sharp tungsten needles (Fine Science Tools) and pinned to glass coverslips. The 2A-eGFP+ signal was used to find areas with hair cells and to target hair cells for recording. Whole-cell patch clamp was performed on the semi-intact tissue with 4-5 MΩ glass electrodes. Data were acquired using an Axopatch 200B amplifier (Molecular Devices), filtered at 5000 Hz, then digitized at 20 kHz through a Digidata 1322A converter. The recording pipette solution contained (in mM): 135 KCl, 5 HEPES, 5 EGTA, 2.5 $MgCl_2$, 2.5 $K_2$-ATP, 0.1 $CaCl_2$, adjusted with KOH to pH 7.4, ~285 mmol $kg^{-1}$. The external solution contained: 137 NaCl, 5.8 KCl, 0.7 $NaH_2PO_4$, 10 HEPES, 1.3 $CaCl_2$, 0.9 $MgCl_2$, 5.6 Glucose, and was supplemented with vitamins and essential amino acids (Invitrogen, Carlsbad, CA), adjusted to pH 7.4 with NaOH, ~310 mmol $kg^{-1}$. Recordings were compensated 40% and cells were held at −66 mV for voltage clamp. Averages are reported ±SEM.

Generation of ATOH1-2A-eGFP reporter cell line. gRNAs (5'-TCGGATGAGGCAAGTTAGGA-3' (SEQ ID NO:17) and 5'-GTCACTGTAATGGGAATGGG-3' (SEQ ID NO:18), offset=0 bp) targeting the stop codon region of ATOH1 were cloned into pSpCas9n(BB) vectors which express Cas9n under the control of CBh promoter (Addgene #48873)[30]. To construct the donor vector, a 2A-eGFP-PGK-Puro cassette (Addgene #31938)[17] flanked by two 1 kb homology arms PCR amplified from extracted WA25 hESC genomic DNA were cloned into a pUC19 backbone. The two gRNA vectors and the donor vector, as well as a vector expressing Cas9n under the control of CMV promoter (Addgene #41816)[18] were transfected into WA25 hESCs with 4D Nucleofector (Lonza) using the P3 Primary Cell 4D-Nucleofector X kit and Program CB-150. After nucleofection, cells were plated in growth medium containing 1× RevitaCell (Thermo Fisher) for improved cell survival rate, and 1 μM of Scr7 (Xcessbio) for higher HDR efficiency[31]. 0.5 μg $μl^{-1}$ puromycin selection was performed for 10 days starting from 48 h post-nucleofection. The PGK-Puro sub-cassette flanked by two LoxP sites was removed from the genome after puromycin selection by nucleofection of a Cre recombinase expressing vector (Addgene #13775). Clonal cell lines were established by low-density seeding (1-3 cells $cm^{-2}$) of dissociated single hESCs followed by isolation of hESC colonies after 5-7 days of expansion. Genotypes of the clonal cell lines were analyzed by PCR amplification followed by gel electrophoresis, and by Sanger sequencing of total PCR amplicons or individual PCR amplicons cloned into TOPO vectors. Cell lines with bi-allelic 2A-eGFP integration were used for inner ear hair cell differentiation.

Statistical analysis. All statistics were performed using GraphPad Prism 7 software. A Shapiro-Wilk normality test was used prior to analysis to determine that the data had a normal distribution. Statistical significance was determined using a one-way analysis of variance (ANOVA) followed by a Dunnett's post-hoc test for multiple comparisons to a control group (e.g. vehicle treated). A Brown-Forsythe test was used to determine that the variation among sample groups was similar. No statistical test was used to predetermine sample size, the investigators were not blinded to the treatment groups, and the samples were not randomized.

Representative Data and Reproducibility. Unless stated otherwise, images are representative of specimens obtained from at least 3 separate experiments. For IHC analysis of aggregates between days 0-12, we typically sectioned 3-6 aggregates from each condition in each experiment. IHC analyses for later stages of the protocol were performed on at least 2 aggregates from each condition per experiment. The finalized culture method was successfully replicated 15 times by four independent investigators using the WA25 (wild-type or ATOH1-2A-eGFP) cell line. The method, with noted modifications, was replicated 3 times using the mND2-0 iPSC line. A replication was deemed successful by confirming pit/vesicle formation during days 12-18 and positively identifying inner ear organoids in at least one aggregate on days 50-100 of differentiation. Experiments were excluded from analysis if no pits were observed during days 12-18.

REFERENCES

1. Géléoc, G. S. G. & Holt, J. R. Sound strategies for hearing restoration. *Science* 344, 1241062 (2014).
2. Müller, U. & Barr-Gillespie, P. G. New treatment options for hearing loss. *Nat Rev Drug Discov* 14, 346-365 (2015).
3. Sergeyenko, Y., Lall, K., Liberman, M. C. & Kujawa, S. G. Age-Related Cochlear Synaptopathy: An Early-Onset Contributor to Auditory Functional Decline. 33, 13686-13694 (2013).
4. DeJonge, R. E., Deig, C. R., Heller, S., Koehler, K. R. & Hashino, E. Modulation of Wnt signaling enhances inner ear organoid development in 3D culture. *PLoS ONE*
5. Koehler, K. R. & Hashino, E. 3D mouse embryonic stem cell culture for generating inner ear organoids. *Nature Protocols* 9, 1229-1244 (2014).
6. Koehler, K. R., Mikosz, A. M., Molosh, A. I., Patel, D. & Hashino, E. Generation of inner ear sensory epithelia from pluripotent stem cells in 3D culture. *Nature* 500, 217-221 (2013).
7. Liu, X.-P., Koehler, K. R., Mikosz, A. M., Hashino, E. & Holt, J. R. Functional development of mechanosensitive hair cells in stem cell-derived organoids parallels native vestibular hair cells. *Nature Communications* (2016).
8. Leung, A. W., Kent Morest, D. & Li, J. Y. H. Differential BMP signaling controls formation and differentiation of multipotent preplacodal ectoderm progenitors from human embryonic stem cells. *Developmental biology* 379, 208-220 (2013).
9. Kwon, H.-J., Bhat, N., Sweet, E. M., Cornell, R. A. & Riley, B. B. Identification of early requirements for preplacodal ectoderm and sensory organ development. *PLoS genetics* 6, e1001133 (2010).
10. Chen, J.-R. et al. Effects of genetic correction on the differentiation of hair cell-like cells from iPSCs with MYO15A mutation. *Cell Death & Differentiation* (2016). doi:10.1038/cdd.2016.16
11. Tang, Z.-H. et al. Genetic Correction of Induced Pluripotent Stem Cells From a Deaf Patient With MYO7A Mutation Results in Morphologic and Functional Recovery of the Derived Hair Cell-Like Cells. *Stem Cells Transl Med* 5, 561-571 (2016).
12. Ohnishi, H. et al. Limited hair cell induction from human induced pluripotent stem cells using a simple stepwise method. *Neuroscience Letters* 599, 49-54 (2015).
13. Ealy, M., Ellwanger, D. C., Kosaric, N., Stapper, A. P. & Heller, S. Single-cell analysis delineates a trajectory toward the human early otic lineage. *PNAS* 201605537 (2016). doi:10.1073/pnas.1605537113
14. Ronaghi, M. et al. Inner Ear Hair Cell-Like Cells from Human Embryonic Stem Cells. *Stem Cells and Development* 23, 1275-1284 (2014).
15. Chen, W. et al. Restoration of auditory evoked responses by human ES-cell-derived otic progenitors. *Nature* 490, 278-282 (2012).
16. Lim, R. & Brichta, A. M. Anatomical and physiological development of the human inner ear. *Hearing research* (2016). doi:10.1016/j.heares.2016.02.004
17. Roberts, R. M. et al. Differentiation of trophoblast cells from human embryonic stem cells: to be or not to be? *Reproduction* 147, D1-12 (2014).
18. Chambers, S. M. et al. Combined small-molecule inhibition accelerates developmental timing and converts human pluripotent stem cells into nociceptors. *Nature Biotechnology* 30, 715-720 (2012).
19. Ladher, R. K., O'Neill, P. & Begbie, J. From shared lineage to distinct functions: the development of the inner ear and epibranchial placodes. *Development* 137, 1777-1785 (2010).
20. Groves, A. K. & Fekete, D. M. Shaping sound in space: the regulation of inner ear patterning. *Development* 139, 245-257 (2012).
21. Ohyama, T., Mohamed, O. A., Taketo, M. M., Dufort, D. & Groves, A. K. Wnt signals mediate a fate decision between otic placode and epidermis. *Development* 133, 865-875 (2006).
22. Hartman, B. H., Durruthy-Durruthy, R., Laske, R. D., Losorelli, S. & Heller, S. Identification and characterization of mouse otic sensory lineage genes. *Frontiers in cellular neuroscience* 9, 79 (2015).
23. Burns, J. C., Kelly, M. C., Hoa, M., Morell, R. J. & Kelley, M. W. Single-cell RNA-Seq resolves cellular complexity in sensory organs from the neonatal inner ear. *Nature Communications* 6, 8557 (2015).
24. Géléoc, G. S. G., Risner, J. R. & Holt, J. R. Developmental acquisition of voltage-dependent conductances and sensory signaling in hair cells of the embryonic mouse inner ear. *The Journal of neuroscience: the official journal of the Society for Neuroscience* 24, 11148-11159 (2004).
25. Liu, X.-P., Koehler, K. R., Mikosz, A. M., Hashino, E. & Holt, J. R. Functional development of mechanosensi- 26. Huch, M. & Koo, B.-K. Modeling mouse and human development using organoid cultures. *Development* 142, 3113-3125 (2015).
27. Nasu, M. et al. Robust Formation and Maintenance of Continuous Stratified Cortical Neuroepithelium by Laminin-Containing Matrix in Mouse ES Cell Culture. *PLoS ONE* 7, e53024 (2012).
28. Hannan, N. R. F., Segeritz, C.-P., Touboul, T. & Vallier, L. Production of hepatocyte-like cells from human pluripotent stem cells. *Nature Protocols* 8, 430-437 (2013).
29. Hama, H. et al. ScaleS: an optical clearing palette for biological imaging. *Nature Neuroscience* 18, 1518-1529 (2015).
30. Ran, F. A. et al. Genome engineering using the CRISPR-Cas9 system. *Nature Protocols* 8, 2281-2308 (2013).
31. Maruyama, T. et al. Increasing the efficiency of precise genome editing with CRISPR-Cas9 by inhibition of non-homologous end joining. *Nature Biotechnology* 33, 538-542 (2015).

Example 2—Modeling Otic Neurogenesis

Figures 16A, 16B, 16C:
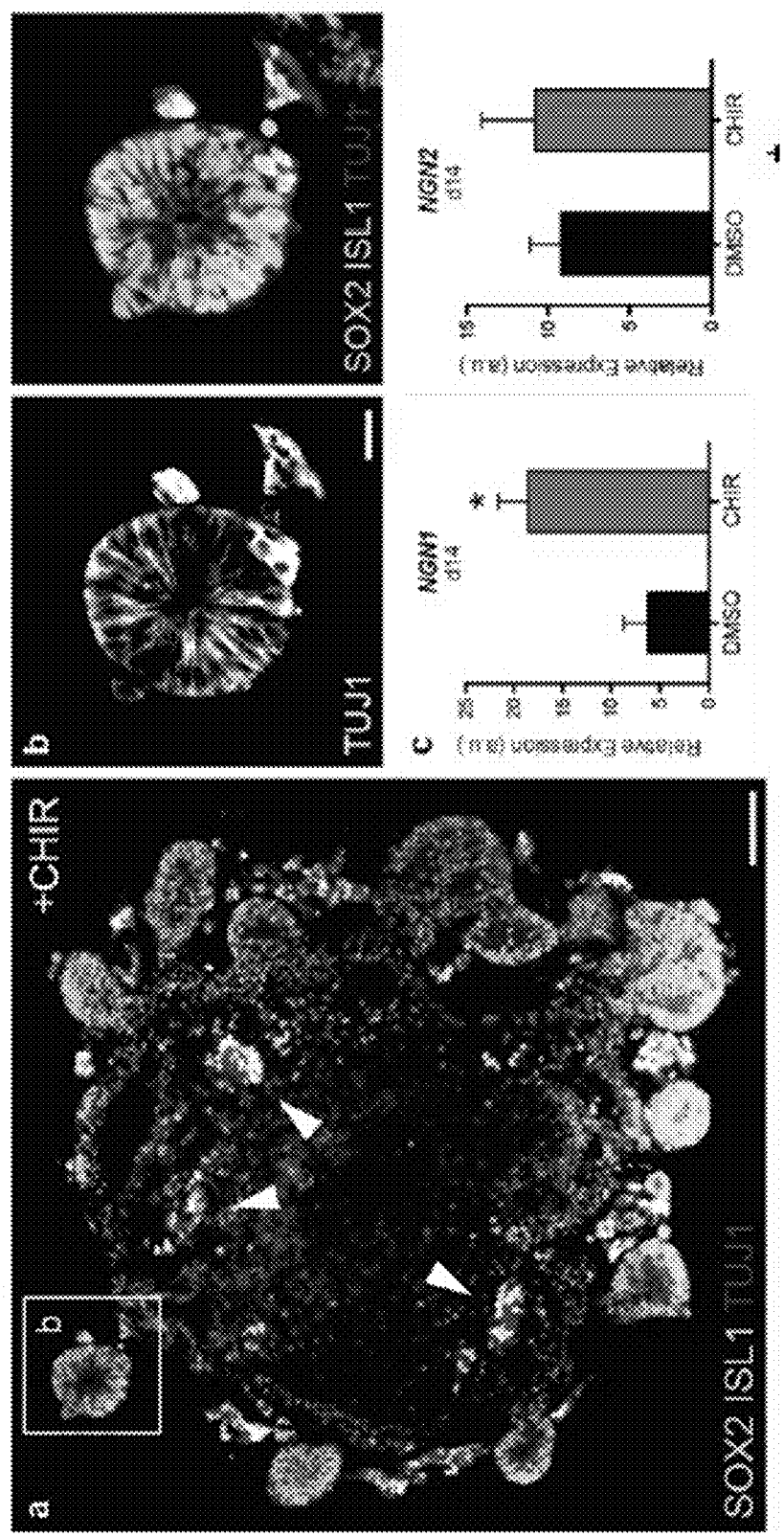
FIGS. 16A-16C demonstrate otic neurogenesis. (a-b) SOX2+ otic vesicles and pits are typically associated with ISL1+ TUJ1+ neuroblasts (day 14). The epithelia of otic vesicles appear to be highly neurogenic at this stage, with weak TUJ1 staining throughout. (c)NGN1 and NGN2 are expressed at day 14 in CHIR-treated samples; normalized to undifferentiated PSCs (n=3). Scale, 100 (a), 20 (b) μm.

In day-12 aggregates, we observed patches of PAX8+ PAX2+ epithelia reminiscent of otic placodes; therefore, we assayed for culture conditions promoting otic vesicle formation. Under control conditions (DMSO), we did not observe vesicle formation (data not shown). Since otic induction is dependent on Wnt signaling, we treated 12-day aggregates with a potent GSK3β inhibitor and known Wnt signaling agonist27, CHIR99021 (CHIR), between days 12-18. Under these conditions, PAX8+ PAX2+ SOX10+ vesicles evaginate from the outer epithelium (~10-30 vesicles per aggregate; see FIGS. 4A-4R). Remarkably, Islet1+ (ISL1+) neuroblasts appear to delaminate from the otic vesicles (FIGS. 16A-16B). We also see neuroblasts in DMSO-treated aggregates and in the non-otic interior of CHIR-treated aggregates (FIG. 16A, arrowheads). Thus, we hypothesized that CHIR-treated aggregates yield a mixture of otic (i.e. vesicle-derived) and epibranchial (i.e. epithelium-derived) neurons (see FIG. 4A). In support of this hypothesis, we confirmed that the neurogenic factors Neurog1 (NGN1), a marker of otic neurons, and Neurog2 (NGN2), a marker of epibranchial neurons, are expressed in CHIR-treated aggregates (FIG. 16C).

Figures 17A, 17B, 17C:
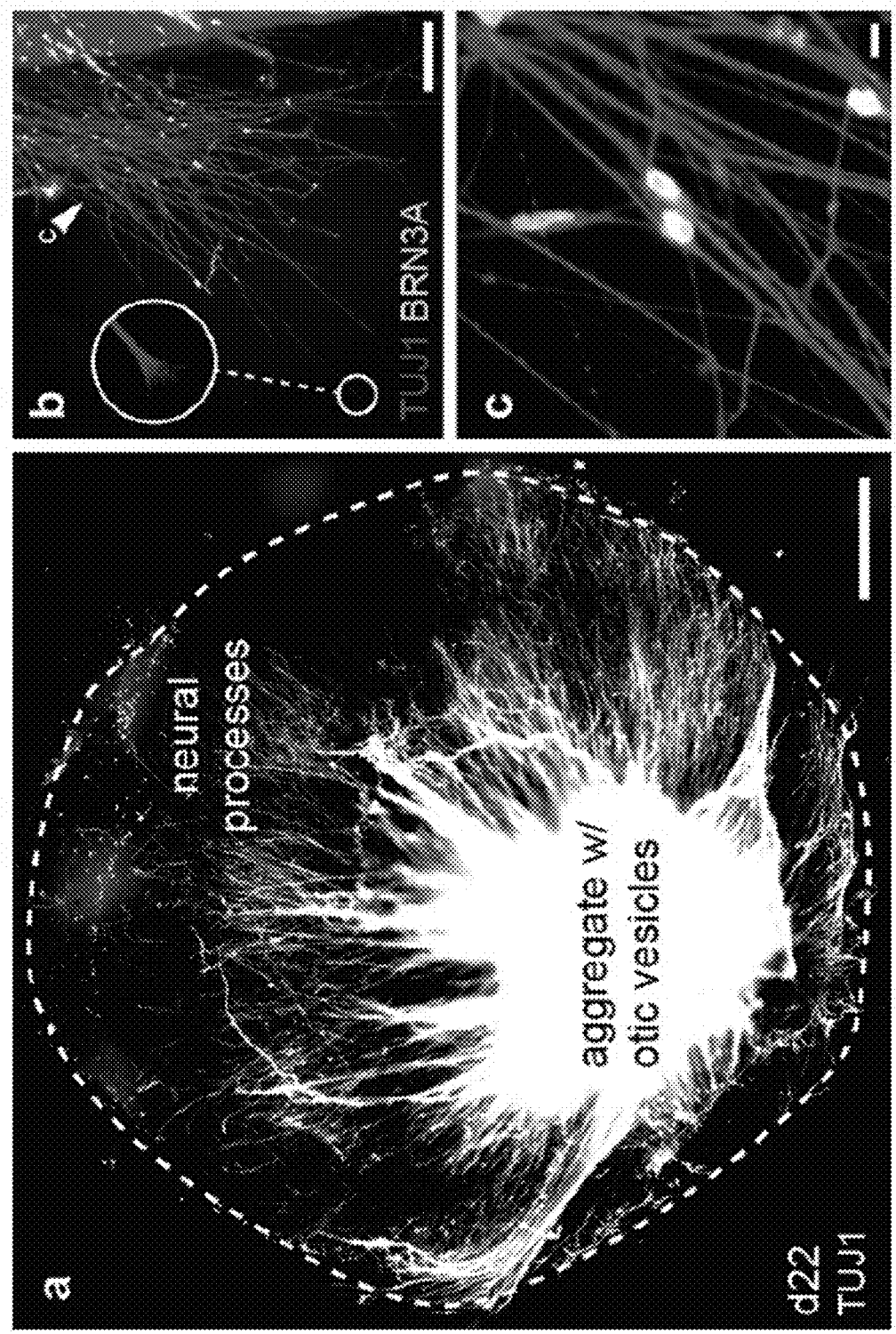
FIGS. 17A-17C demonstrate sensory neuron outgrowth and maturation. HIR-treated organoids plated on Matrigel produce TUJ1+ BRN3A+ neurons with a bipolar morphologies. Growth cone (inset in b). Scale, 500 (a), 50 (b), 10 (c).

After 12 days of differentiation, otic induced aggregates were plated on bacterial dishes in Matrigel droplets in medium containing 3 μM CHIR. See FIGS. 17A-17C. On day 22, the aggregates were fixed and immunostained with antibodies for markers of sensory neurons, BRN3A and BIII-Tubulin (TUJ1). Radially oriented BRN3A+ TUJ1+ neurons produced outgrowing processes with growth cones, confirming widespread sensory neurogenesis in the organoid cultures.

Figures 18A, 18B, 18C:
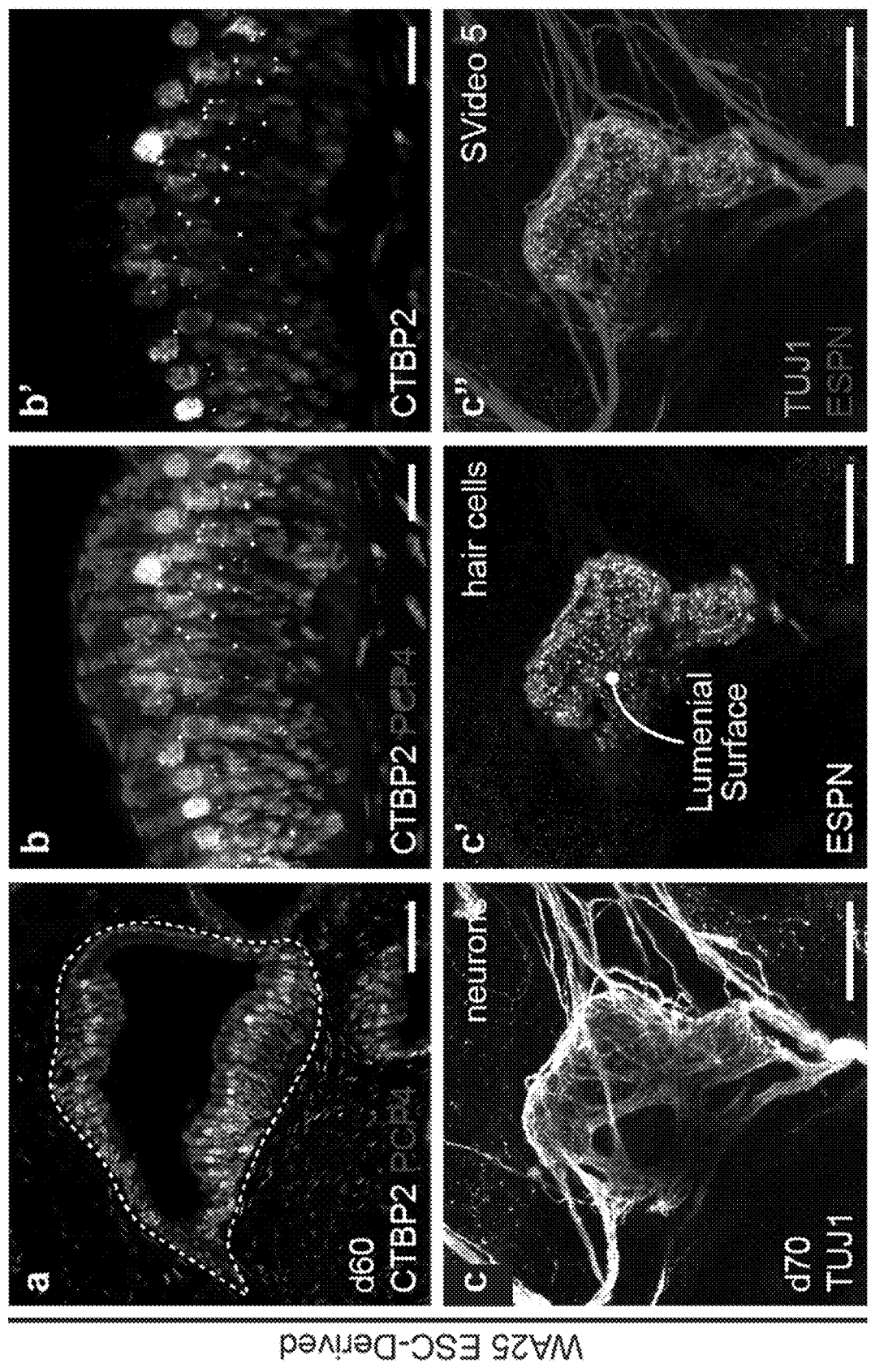
FIGS. 18A-18C demonstrate that inner ear organoid-derived hair cells have ribbon synapse-like structures and are innervated by sensory neurons. A-B, CTBP2-positive puncta in WA25 hESC-derived PCP4-positive hair cells on day 60 of differentiation. C, Representative image of neurons innervating an inner ear organoid sensory epithelium. Scale bars, 100 μm (C), 25 μm (A, B).
Figure 19:
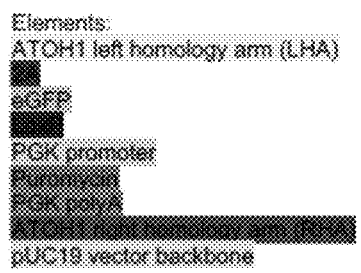
FIG. 19 depicts the ATOH1-2A-eGFP-PGK-Puro donor plasmid sequence (SEQ ID NO:21).

As further evidence of inner ear organogenesis in our culture system, the hair cells displayed CTBP2$^+$ puncta by day 60-70 of culture, indicating putative ribbon synapse-like structures (FIGS. 18A-18B; n=7 sensory epithelia). As noted previously, we observed BRN3a-positive sensory-like neurons in cell aggregates during the vesicle formation stage. Additionally, we observed TUJ1$^+$ neuronal processes targeted to sensory epithelia with hair cells (FIG. 18C). Together, our findings suggest that the human inner ear organoid model may recapitulate assembly of the sensorineural circuit between hair cells and sensory neurons.

Example 3—Exemplary Protocol for In Vitro Production of Inner Ear Organoids

This example describes a protocol for inducing formation of non-neural ectoderm and inner ear sensory tissue from human pluripotent stem cells. As described in greater detail in the following paragraphs, pluripotent stem cells aggregates were cultured in a medium containing Matrigel, which is rich in basement membrane proteins, to induce ectoderm development and production of ectoderm epithelium on the aggregate surface. We then used a combined treatment of bone morphogenetic protein-4 (BMP4) and a transforming growth factor beta (TGFβ) inhibitor such as the small molecule SB-431542 ("SB") to promote non-neural differentiation in the epithelium. To further initiate inner ear induction, BMP signaling was inhibited and fibroblast growth factor (FGF) signaling was activated using recombinant FGF-2 approximately 24 hours after the initial BMP4 and SB treatment. Remarkably, the combined treatment protocol initiated self-organization of otic vesicles that later developed into inner ear organoids containing functional vestibular sensory epithelia.

Methods

ES cell culture in E8 medium on Vitronectin-coated plates (steps 1-7). We maintain our hPS cells in E8 Medium under feeder-free conditions and use EDTA for passaging (see previous protocol by Beers et al.)1 We prefer this method of hPS cell maintenance because, in our hands, it reduces spontaneous differentiation with limited time and effort.

Non-neural ectoderm and pre-otic induction (steps 8-27). To start differentiation, hPS cells are dissociated and distributed, 5,000 cells per well, onto 96-well V-bottom plates. For this initial aggregation step we use E8 medium containing Y-27632, a potent ROCK signaling inhibitor. ROCK signaling inhibition has been shown to limit the amount of dissociation-induced apoptosis in hPS cells. Additionally, we have found that aggregation in E8 medium helps with cell survival and leads to more uniform cell aggregates, which impacts the reproducibility of the protocol. SB treatment inhibits TGFB to induce ectoderm development. Endogenous BMP signaling generates non-neural rather than neural ectoderm. FGF-2 and LDN treatment induces pre-placodal development. By day 8 the outer epithelium begins to express PAX8, indicating an oticepibranchial placode (OEPD)-like character. CHIR treatment on day 8 induces small patches of PAX2+ cells, indicating the earliest signs of otic placode development by day 12.

Otic prosensory vesicle and inner ear organoid formation (steps 28-43). A low concentration of extracellular matrix proteins (e.g., Matrigel™) does not seem to be supportive of otic vesicle formation. To encourage the otic placode-like patches to evaginate and pinch off from the epithelium as an otic vesicle, we embed day 12 aggregates in Matrigel. The Matrigel-embedded aggregates are cured onto the surface of bacterial dishes and bathed in a serum-free medium containing N2 and B27 supplement previously shown to support tissue self-organization (hereafter, Organoid Medium). This supportive environment, combined with continued exposure to CHIR, causes numerous vesicles to bud-off of the epithelium between days 12-18. Otic vesicle formation was observed in >95% of the aggregates (>100 aggregates) across four independent experiments. Additionally, between days 12-18, neuroblasts delaminate from other parts of the epithelium and differentiate into sensory neurons. It is currently unclear whether these sensory neurons are epibranchial neurons such as those of cranial nerves VII, IX, and X, or inner ear neurons such as the vestibular or spiral ganglion neurons. Formation of a mesenchyme containing chondrocyte progenitor cells was also observed. It was unclear, however, whether the chondrocyte progenitor cells arose from ectodermal epithelium or another population of mesodermal cells.

On day 18, the Matrigel®-embedded aggregates were removed from the stationary culture dish and pipetted into spinner flasks containing Organoid Medium devoid of any added growth factors or small molecules. After a total of 22 days, 10-30 vesicles were observed in each aggregate using phase contrast imaging. These vesicles expressed PAX2, PAX8, SOX2, and JAG1 protein indicating an otic cell fate. The vesicles appeared to grow slowly between days 22-35, and it became difficult to observe the vesicles using phase contrast imaging during this period due to the growing density of the mesenchymal cell mass in which they are embedded. By days 35-40, the vesicles were generally more apparent in the aggregate interior. The vesicles typically exhibited convoluted, multi-chambered morphologies, in contrast to the simple spherical and ovoid shaped otic vesicles. By day 45, vesicles have developed $MYO7A^+$ hair cell-like cells and were identified as inner ear organoids. Between days 60-80, we observed $MYO7A^+$ hair cells with F-actin-rich and $Espin^+$ hair bundles, indicating a definitive hair cell identity.

Materials and Reagents hPSC culture: Human PSCs (WA25 hESCs, passage 22-50; mND2-0 iPSCs, passage 28-46) were cultured in Essential 8 (E8) Medium or Essential 8 Flex Medium (E8f) (Invitrogen) supplemented with 100 μg/ml Normocin (Invivogen) on recombinant human Vitronectin-N (Invitrogen)-coated 6-well plates according to an established protocol[12, 13]. At 80% confluency or every 4-5 days, the cells were passaged at a split ratio of 1:10-1:20 using an EDTA solution. Both cell lines were acquired from the WiCell Research Institute and arrived with a statement of verification and authenticity. Additional validation and testing information can be found on the cell line webpages, available at wicell.org/home/stem-cell-lines/catalog-of-stem-cell-lines/wa25.cmsx and wicell.org/home/stem-cell-lines/catalog-of-stem-cell-lines/mirjt7i-mnd2-0.cmsx on the World Wide Web. Cell lines were determined to be mycoplasma contamination-free using the MycoAlert Mycoplasma Detection Kit (Lonza).

Other reagents used in this exemplary protocol are set forth in Table 6.

TABLE 6

REAGENTS

Ham's F-12 Nutrient Mixture (Gibco, cat. no. 31765-035)
Iscove's Modified Dulbecco's Medium (IMDM) (Gibco, cat. no. 31980-030)
Advanced DMEM/F12 (Gibco, cat. no. 12491-015)
2-Mercaptoethanol (Gibco, cat. no. 21985-023)
Normocin (Invivogen, cat. no. ant-nr-1)
N2 Supplement (Gibco, cat. no. 17502-048)
GlutaMax (Gibco, cat. no. 35050-079)
Geltrex (Invitrogen, cat. no. A1413302)
Vitronectin (Invitrogen, cat. no. A14700)
Chemically-defined lipid concentrate (Invitrogen, cat. no. 11905-031)
Albumin from bovine serum (BSA; Sigma, cat. no. A1470)
Insulin solution (Sigma, cat. no. I9278)
Human Transferrin (Sigma, cat. no. T8158)
1-thioglycerol (Sigma, cat. no. M1753)

TABLE 6-continued

REAGENTS

Human BMP-7 (Peprotech, cat. no. 120-03B)
Human FGF-3 (Biolegend, cat. no. 558002)
FGF-2 (Peprotech, cat. no. 100-18B)
SB-431542 in solution (Stemgent, cat. no. 04-0010-05)
LDN-193189 in solution (Stemgent, cat. no. 04-0074-02), a light sensitive solution. Store in the dark at −20° C. per the manufacture's recommendation.
Neurobasal Medium (Gibco, cat. no. 21103-049)
B27 Supplement minus Vitamin A (Gibco, cat. no. 12587-010)
CHIR99021 in solution (Stemgent, cat. no. 04-0004-02)
Y-27632 in solution (Stemgent, cat. no. 04-0012-02)
TrypLE Express (Gibco, cat. no. 12605010)
UltraPure 0.5M EDTA, pH 8.0 (Invitrogen, cat. no. 15575-020)
Dulbecco's Phosphate Buffered Saline (DPBS; Gibco, cat. no. 12605010)
Dimethyl Sulfoxide (DMSO; Sigma, cat. no. D8418)
Paraformaldehyde (PFA, Electron Microscopy Sciences, cat. no. 15710)
Normal goat serum (Vector Laboratories, cat. no. S-1000)
Triton X-100 (Sigma, cat. no. T8787)
Antibodies required for desired characterization Culture Medium and Stock Solutions Human recombinant BMP7 stock solution (100 ng/μL): In the biosafety cabinet, add 100 μL of sterile 4 mM HCl to 10 μg of BMP7; vortex the solution and spin down in a tabletop centrifuge. Store BMP4 solution in 5 μL aliquots at −20° C. for 6 months or at −80° C. for 1 year.

Human recombinant FGF-2 stock solution (200 ng/μL): In the biosafety cabinet, add 250 μL of sterile PBS or 5 mM Tris (pH 7.6) to 50 μg of FGF-2; vortex the solution and spin down in a tabletop centrifuge. Store FGF-2 solution in 6 μL aliquots at −20° C. for 6 months or at −80° C. for 1 year.

Human transferrin stock solution (20 mg/ml): In the biosafety cabinet, dissolve 100 mg of recombinant human transferrin in 5 ml of IMDM. To fully dissolve, vortex the tube and place it on a rotating shaker for 5-10 min at room temperature (RT). Store the transferrin solution in 150 μl aliquots at −20° C. for 6 months or at −80° C. for 1 year.

EDTA Solution (for passaging hES cells): In the biosafety cabinet, mix 50 μl of 0.5 M EDTA into 50 ml DPBS. Filter sterilize the solution. EDTA solution can be stored at RT for 6 months.

Chemically Defined Medium (CDM): To prepare 200 mL CDM, measure out 1 g BSA in a 250 mL bottle. Dissolve the BSA in 100 mL F-12 Nutrient Mixture +GlutaMAX, 100 mL IMDM +GlutaMAX, 2 mL chemically-defined lipid concentrate, 140 μL Insulin, 150 μL Transferrin, and 8 μL 1-thioglycerol. Sterile filter using a low-protein binding filter. CDM should be used for up to 2 weeks and stored at 4° C. Add Normocin to the media just before use at a dilution of 2 μl per 1 mL of CDM. See Table 1 for a quick reference recipe.

Differentiation CDM: In a 50 mL conical tube, add 450 μL of ice cold Geltrex to 34.5 mL of ice cold CDM (1.25% final concentration). Vortex the tube well to fully dissolve the Geltrex. Place 30 mL of this solution in a new 50 mL conical tube. Add 0.6 μL of FGF-2 (4 ng/mL final concentration) and 30 μL of SB-431542 (10 μM final concentration). Vortex the tube well to mix. Differentiation CDM should be made fresh on day 0 of differentiation. Use the remaining 5 mL of CDM +Geltrex to wash the aggregates before plating.

Organoid Maturation Medium (OMM): To prepare 50 mL OMM, combine 24.5 mL Advanced DMEM/F12, 24.5 mL Neurobasal Medium, 500 μL B-27 Supplement without vitamin A, 500 μL GlutaMAX, 250 μL N2-supplement, and 100 μL Normocin in a sterile 50 mL conical tube. OMM can be used for up to 2 weeks if stored at 4° C. See Table 3 for a quick reference recipe.

Procedures

ES Cell Maintenance and Passaging:

1. In the biosafety cabinet, dilute 60 µL of Vitronectin solution in 6 mL of DPBS. Add 1 mL of diluted vitronectin to each well of a 6-well culture plate. Incubate at RT for at least 1 hr and in the mean time proceed to step 2.

2. Equilibrate at least 20 mL of E8 Medium containing Normocin to RT.

3. To begin dissociation of the 70-80% confluent hES cells, aspirate the spent E8 Medium from one well and wash twice with DPBS.

4. Add 1 mL of EDTA solution and incubate in a 37° C. incubator for 4-8 min. Under a microscope, confirm that holes have formed in the center of the colonies.

5. During the EDTA incubation, remove the vitronectin solution from the 6-well plate and quickly add 1.5 mL of E8 Medium to each well before the surface dries.

6. Collect the dissociated cells into 6 mL of E8 Medium. CRITICAL You may need to vigorously triturate the medium to remove the cell clusters from the plate. Do not over pipet the cells, as this will cause apoptosis. Care should be taken to not introduce air bubbles into the medium.

7. Plate the cells on the prepared 6-well plate (from step 5). Select plating density based on when you next wish to split the cells. We typically add 500 mL (passage in 2-3 days) or 250 µL (passage in 4-5 days) of cell suspension to each well. Incubate cells at 37° C. in 5.0% $CO_2$ until ready for passage or use in an experiment.

hES Cell Differentiation (Day −2 to Day 0): Aggregation:

8. In the biosafety cabinet, prepare conical tubes containing 22 mL and 10 mL of E8 Medium with Normocin. Add 44 µL of Y-27632 to the 22 mL tube (20 µM final concentration; hereafter, E8-Y20) and 10 µL of Y-27632 to the 10 mL tube (10 µM final concentration; hereafter, E8-Y10).

9. When cells are 70-80% confluent, aspirate the E8 Medium from one well and wash three times with DPBS at RT.

10. Add 350 µL of TrypLE and incubate at 37° C. for 2-4 min. Following incubation, shake the plate horizontally to break up the cells. Under a microscope, confirm that the cells have rounded and are detached from the surface of the plate.

11. Collect the dissociated cells into 5 mL of E8-Y10 Medium and transfer them into a 15 mL conical tube.

12. Break the cell clumps into single-cells by pipetting with a P1000 tip. Pellet the cells, by centrifugation at 200 g for 5 minutes.

13. Completely remove the supernatant and resuspend the cell pellet in 1 mL of E8-Y10 Medium.

14. Forcefully pipet 1 mL of E8-Y10 Medium through a cell-strainer-top test tube to prime the strainer. Pipet the 1 mL of hES cell suspension drop-wise onto the cell strainer. Next, pipet 1 mL of E8-Y10 Medium drop-wise onto the cell strainer. There should be 3 mL in the test tube. This step is important for ensuring that the cells are completely dissociated into single cells.

15. Mix the cell suspension by pipetting with a P1000 tip and determine the concentration of cells using a hemocytometer or automated cell counter.

16. Dilute the appropriate volume of cell suspension in the 22 mL of E8-Y20 Medium to acquire a final concentration of 50,000 cells per mL (i.e., $1.1 \times 10^6$ total cells). For example, if the cell suspension contains $1 \times 10^6$ cells per mL, dilute 1.1 mL of cell suspension ($1.1 \times 10^6$ divided by $1 \times 10^6$) in 20.9 mL of E8-Y20 Medium. Invert several times to mix.

17. Pour the cell suspension into a reservoir and aliquot 100 µl of cell suspension into each well of two 96-well V-bottom plates using a multichannel pipette.

18. Spin down the plates at 120 g for 5 min at RT.

19. Place the plates in a 37° C. incubator with 5.0% CO2 for 48 hrs. Add 50 µl of fresh E8 Medium (not containing Y-27632) to each well after 24 hrs.

Differentiation Day 0: Transfer to Differentiation CDM:

20. Prepare 30 ml of Differentiation CDM containing Geltrex, FGF-2, and SB-431542. Allow the media to equilibrate to RT.

21. With the multichannel pipette set to 125 µl (i.e. 25 µl less than the volume of each well), carefully the aggregates from each well of the 96-well plate from step 18. Deposit the aggregates in a bacterial dish and then transfer them to a 2-ml tube.

22. Wash the aggregates at least 3 times with CDM to completely remove traces of E8 Medium.

23. Resuspend the aggregates in differentiation CDM and transfer them to a new bacterial dish.

24. Using a P200 pipette, individually transfer each aggregate to each well of two 96-well U-bottom plates in 100 µl of media. It may be difficult to see the aggregates at this stage. We typically place the bacterial dish on a non-reflective white surface (e.g., a Kimwipe) to enhance the contrast of the aggregates.

25. Return plates to the incubator for 4 days. Observe the morphology of the aggregates daily.

Differentiation Day 4: Addition of FGF-2 and LDN-193189 (FGF/LDN):

26. In a 15-ml conical tube, add FGF-2 and LDN-193189 to the CDM at a 5× concentration. For example, we add 6.25 µl of 200 ng/µl FGF-2 and 0.5 µL of 10 mM LDN-193189 to 5 ml of CDM.

27. Add 25 µl of CDM containing FGF/LDN to each well of the plate from step 24. Each well now contains 125 µl of medium with a final concentration of 50 ng/ml FGF-2 and 200 nM LDN-193189. Incubate cells for a further 4 days.

28. In a 15-ml conical tube, add CHIR99021 to the CDM at a 6× concentration. For example, we add 9 µl of 10 mM CHIR99021 to 5 ml of CDM.

29. Add 25 µl of CDM containing CHIR to each well of the plate from step 26. Each well now contains 125 µl of medium with a final concentration of 3 µM CHIR. Incubate cells for a further 4 days.

Differentiation Day 12: Transition to Static ECM Culture:

30. About 2 hrs prior to performing the following steps, remove a 1-ml aliquot of Geltrex from the freezer and allow it to thaw completely on ice or in the refrigerator.

31. Prepare 50 ml of organoid medium in a 50-ml conical tube.

32. Using a cut P1000 pipette tip, transfer the aggregates from each well of the plate in step 28 into a 2-ml tube.

33. Allow the aggregates to settle at the bottom of the tube and then carefully aspirate the media.

34. Wash the aggregates with 1-2 ml of RT organoid medium at least 3 times. Remove as much of the medium as possible following the final wash.

35. Resuspend the aggregates in ice-cold Geltrex. Set the pipette to 20 µl and individually transfer the aggregates to a 100 mm bacterial dish. We typically add 20-30 droplets to each plate. Gentle shaking the plate in different directions helps to flatten and adhere the droplets to the surface of the plate. Geltrex will begin to polymerize after 10-15 minutes at RT. It is recommended to keep a small container of ice in biosafety cabinet where the aggregate/Geltrex mixture can be placed between pipetting steps.

36. Incubate the plates without medium for 30 minutes at 37° C.

37. Add 10-12 ml of organoid medium containing CHIR. Add the orgnaoid medium slowly as to not detach the droplets from the plate. It is fine if some droplets may detach.

38. Incubate cells for a further 6 days. Perform a half media change after 3 days.

Differentiation Day 18: Transition to Spinner Flask:

39. Using a wide-mouth P1000 tip, scrape-off and pipette-up each aggregate from the surface of the bacterial dish. Transfer the aggregates to a 2-ml tube.

40. Wash the aggregates 3 times with organoid medium.

41. Pour 50-75 ml of organoid medium into a 125-ml spinner flask.

42. Add the aggregates to the spinner flask. Confirm that the side ports are opened by a ¼ turn and place the spinner flask in the incubator on the stirrer plate. Set the stirrer controller at 60-65 rpm.

43. Incubate cells for a further 22-42 days. Completely change the medium every week. For longer experiments, aggregates can be maintained in the spinner flask indefinitely. To monitor development, we periodically transfer the aggregates to a bacterial dish using wide-mouth P1000 and image using an inverted microscope.

Timing:
Steps 1-7, Maintenance and passaging hES cells: 30 min
Steps 8-19, hES cell differentiation: Aggregation: 40 min
Steps 20-25, Differentiation day 0: Transfer to Differentiation CDM: 1 hr
Steps 26-27, Differentiation day 4: Addition of FGF-2 and LDN-193189: 20 min
Steps 28-29, Differentiation day 8: Addition of CHIR99021: 20 min
Steps 30-38, Differentiation day 12: Transition to static ECM culture: 45 min
Steps 39-43, Differentiation day 18: Transition to bioreactor: 30 min
Steps 1-43, Total time to generate inner ear organoids: 45-60 days to >1 yr

We claim:

1. A method of obtaining a three-dimensional composition comprising human inner ear sensory tissue, the method comprising the steps of:
   (a) culturing human pluripotent stem cell aggregates in a culture medium comprising Fibroblast Growth Factor-2 (FGF-2), a Bone Morphogenetic Protein (BMP), and a small molecule inhibitor of Transforming Growth Factor Beta (TGFB)-mediated signaling for four days;
   (b) further culturing the cultured aggregates of (a) in the presence of a Fibroblast Growth Factor (FGF) and an inhibitor of BMP signaling for four days;
   (c) contacting the further cultured aggregates of (b) to a Wnt agonist for four days, whereby cells within the contacted aggregates differentiate into pre-otic epithelial cells;
   (d) embedding the pre-otic epithelial cells obtained in step (c) in droplets of a semi-solid medium comprising extracellular matrix;
   (e) culturing the droplets of embedded pre-otic epithelial cells in a static culture in the presence of a Wnt agonist for 6 days under conditions that promote self-assembly of embedded pre-otic epithelial cells into otic vesicles; and
   (f) culturing the droplets of embedded pre-otic epithelial cells of (e) further in a stirring culture for at least 22-42 days, whereby a three-dimensional composition comprising human inner ear sensory tissue is obtained.

2. The method of claim 1, wherein the Wnt agonist is an inhibitor of GSK3.

3. The method of claim 2, wherein the inhibitor of GSK3 is selected from the group consisting of CHIR99021, lithium chloride (LiCl), and 6-bromoindirubin-3'-oxime (BIO).

4. The method of claim 1, wherein the extracellular matrix is a basement membrane extract (BME).

5. The method of claim 1, wherein the three-dimensional composition comprises one or more mechanosensory cells.

6. The method of claim 1, wherein the three-dimensional composition comprises one or more sensory neuron cells.

7. The method of claim 1, wherein the three-dimensional composition comprises one of more sensory neuron cells that form synaptic connections with mechanosensory cells.

8. The method of claim 1, wherein the BMP is selected from the group consisting of BMP2, BMP4, and BMP7.

9. The method of claim 1, wherein the FGF of (b) is FGF-2.

10. The method of claim 1, wherein the inhibitor of BMP signaling is LDN-93189.

11. The method of claim 1, wherein the small molecule inhibitor of TGFβ1-mediated signaling is SB431542.

12. The method of claim 1, wherein the small molecule inhibitor of TGFβ1-mediated signaling is A-83-01.

13. The method of claim 1, wherein the otic vesicles comprise a multi-chambered morphology.

14. The method of claim 1, wherein the three-dimensional composition comprises a hair cell bearing organoid.

15. The method of claim 1, wherein the three-dimensional composition comprises a functional human hair cell.

16. The method of claim 15, wherein the functional human hair cell has an outwardly rectifying current, wherein the functional human hair cell has no sodium current.

17. The method of claim 1, wherein the three-dimensional composition comprises cells expressing mRNA or protein for MYO7A, PCP4, ANXA4, SOX2, and CALB2.

18. The method of claim 1, wherein the three-dimensional composition comprises cells expressing mRNA or protein for SOX10 and SPARCL1.

19. The method of claim 1, wherein the three-dimensional composition comprises cells expressing hair cell markers, wherein the cells expressing hair cell markers have apical stereocilia bundles, and the apical stereocilia bundles contain F-actin and espin, with the apical stereocilia bundles protruding into the vesicle lumen.

20. The method of claim 19, wherein the stereocilia bundles contain acetylated-Tubulin alpha 4a (TUBA4A) kinocilium.

* * * * *

UNITED STATES PATENT AND TRADEMARK OFFICE
CERTIFICATE OF CORRECTION

| | | |
|---|---|---|
| PATENT NO. | : 12,077,778 B2 | Page 1 of 1 |
| APPLICATION NO. | : 16/989554 | |
| DATED | : September 3, 2024 | |
| INVENTOR(S) | : Karl R. Koehler et al. | |

It is certified that error appears in the above-identified patent and that said Letters Patent is hereby corrected as shown below:

In the Claims

Claim 1, Column 45, Line 31, "(TGFB)" should be --(TGFβ)--.

Signed and Sealed this
Eighth Day of October, 2024

*Katherine Kelly Vidal*

Katherine Kelly Vidal
*Director of the United States Patent and Trademark Office*

SEQUENCE LISTING

<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: synthetic primer

<400> SEQUENCE: 1
cgtgaagaac attgatgatg gc                                          22

<210> SEQ ID NO 2
<211> LENGTH: 20
<212> TYPE: DNA
<213> ORGANISM: Artificial Sequence
<220> FEATURE:
<223> OTHER INFORMATION: synthetic primer

<400> SEQUENCE: 2
gcgatcttct tcttgcccat                                             20

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
tactcgccca agtcggaata                                             20

<210> SEQ ID NO 4
<211> LENGTH: 20
<212> TYPE: DNA
<213> ORGANISM: Artificial Sequence
<220> FEATURE:
<223> OTHER INFORMATION: synthetic primer

<400> SEQUENCE: 4
ttcttgggct tcccattcac                                             20

<210> SEQ ID NO 5
<211> LENGTH: 19
<212> TYPE: DNA

```
<213> ORGANISM: Artificial Sequence
<220> FEATURE:
<223> OTHER INFORMATION: synthetic primer

<400> SEQUENCE: 5
tttcagccat ggaccgtca                                                    19

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
gggagattga cctacagtgc                                                   20

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
gggctctctg agaggcaggt                                                   20

<210> SEQ ID NO 8
<211> LENGTH: 19
<212> TYPE: DNA
<213> ORGANISM: Artificial Sequence
<220> FEATURE:
<223> OTHER INFORMATION: synthetic primer

<400> SEQUENCE: 8
cctttgctct gcggttctg                                                    19

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
tgcttccctg agacccagtt                                                   20

<210> SEQ ID NO 10
<211> LENGTH: 25
<212> TYPE: DNA
<213> ORGANISM: Artificial Sequence
<220> FEATURE:
<223> OTHER INFORMATION: synthetic primer

<400> SEQUENCE: 10
gatcacttct tcctttgca tcaag                                              25

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
agtgagaggc aacctggaga                                                   20
```

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
acactcggac cacatccttc                                        20

<210> SEQ ID NO 13
<211> LENGTH: 21
<212> TYPE: DNA
<213> ORGANISM: Artificial Sequence
<220> FEATURE:
<223> OTHER INFORMATION: synthetic primer

<400> SEQUENCE: 13
catgagtgtg gatccagctt g                                      21

<210> SEQ ID NO 14
<211> LENGTH: 21
<212> TYPE: DNA
<213> ORGANISM: Artificial Sequence
<220> FEATURE:
<223> OTHER INFORMATION: synthetic primer

<400> SEQUENCE: 14
cctgaataag cagatccatg g                                      21

<210> SEQ ID NO 15
<211> LENGTH: 23
<212> TYPE: DNA
<213> ORGANISM: Artificial Sequence
<220> FEATURE:
<223> OTHER INFORMATION: synthetic primer

<400> SEQUENCE: 15
caacataaac ggactcaatc cca                                    23

<210> SEQ ID NO 16
<211> LENGTH: 22
<212> TYPE: DNA
<213> ORGANISM: Artificial Sequence
<220> FEATURE:
<223> OTHER INFORMATION: synthetic primer

<400> SEQUENCE: 16
accacctcta cgaacacatt gt                                     22

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
tcggatgagg caagttagga                                        20

<210> SEQ ID NO 18
<211> LENGTH: 20
<212> TYPE: DNA
<213> ORGANISM: Artificial Sequence
<220> FEATURE:

<223> OTHER INFORMATION: synthetic primer

<400> SEQUENCE: 18
gtcactgtaa tgggaatggg                                                      20

<210> SEQ ID NO 19
<211> LENGTH: 64
<212> TYPE: DNA
<213> ORGANISM: Artificial Sequence
<220> FEATURE:
<223> OTHER INFORMATION: synthetic

<400> SEQUENCE: 19
gggaattttc ccccattcc cattacagtg actcggatga ggcaagttag aaggtgaca          60 gaag                                                                       64

<210> SEQ ID NO 20
<211> LENGTH: 64
<212> TYPE: DNA
<213> ORGANISM: Artificial Sequence
<220> FEATURE:
<223> OTHER INFORMATION: synthetic

<400> SEQUENCE: 20
cccttaaaag gggggtaagg gtaatgtcac tgagcctact ccgttcaatc cttccactgt          60
cttc                                                                       64

<210> SEQ ID NO 21
<211> LENGTH: 7354
<212> TYPE: DNA
<213> ORGANISM: Artificial Sequence
<220> FEATURE:
<223> OTHER INFORMATION: synthetic

<400> SEQUENCE: 21
tcgcgcgttt cggtgatgac ggtgaaaacc tctgacacat gcagctcccg gagacggtca          60
cagcttgtct gtaagcggat gccggagcaa gacaagcccg tcagggcgcg tcagcgggtg         120
ttggcgggtg tcggggctgg cttaactatg cggcatcaga gcagattgta ctgagagtgc         180
accatatgcg gtgtgaaata ccgcacagat gcgtaaggag aaaataccgc atcaggcgcc         240
attcgccatt caggctgcgc aactgttggg aagggcgatc ggtgcgggcc tcttcgctat         300
tacgccagct ggcgaaaggg ggatgtgctg caaggcgatt aagttgggta acgccagggt         360
tttcccagtc acgacgttgt aaaacgacgg ccagtgaatt cgagctcggt acccggggat         420
ccccagcccc agccgcatca tctcccgcaa ccgccgccgc cgccgcagcc acctgcaact         480
ttgcaggcga gagagcatcc cgtctacccg cctgagctgt ccctcctgga cagcaccgac         540
ccacgcgcct ggctggctcc cactttgcag ggcatctgca cggcacgcgc cgcccagtat         600
ttgctacatt ccccggagct gggtgcctca gaggccgctg cgccccggga cgaggtggac         660
ggccgggggg agctggtaag gaggagcagc ggcggtgcca gcagcagcaa gagccccggg         720
ccggtgaaag tgcgggaaca gctgtgcaag ctgaaaggcg gggtggtggt agacgagctg         780
ggctgcagcc gccaacgggc cccttccagc aaacaggtga atgggtgcaa gaagcagaga         840
cggctagcag ccaacgccag ggagcggcgc aggatgcatg gctgaacca cgccttcgac          900 cagctgcgca atgttatccc gtcgttcaac aacgacaaga gctgtccaa atatgagacc         960 ctgcagatgg cccaaatcta catcaacgcc ttgtccgagc tgctacaaac gcccagcgga        1020
ggggaacagc caccgccgcc tccagcctcc tgcaaaagcg accaccacca ccttcgcacc        1080

```
gcggcctcct atgaagggggg cgcgggcaac gcgaccgcag ctggggctca gcaggcttcc    1140
ggagggagcc agcggccgac cccgcccggg agttgccgga ctcgcttctc agccccagct    1200
tctgcgggag ggtactcggt gcagctggac gctctgcact tctcgacttt cgaggacagc    1260
gccctgacag cgatgatggc gcaaaagaat ttgtctcctt ctctcccegg gagcatcttg    1320 cagccagtgc aggaggaaaa cagcaaaact tcgcctcggt cccacagaag cgacggggaa    1380 ttttccccce attcccatta cagtgactcg gatgaggcaa gtgctagcgc cactaacttc    1440
tccctgttga acaagcagg ggatgtcgaa gagaatcccg gccaatggt gagcaagggc      1500 gaggagctgt tcaccggggt ggtgcccatc ctggtcgagc tggacggcga cgtaaacggc    1560
cacaagttca gcgtgtccgg cgagggcgag ggcgatgcca cctacggcaa gctgaccctg    1620
aagttcatct gcaccaccgg caagctgccc gtgccctggc ccaccctcgt gaccaccctg    1680
acctacggcg tgcagtgctt cagccgctac cccgaccaca tgaagcagca cgacttcttc    1740
aagtccgcca tgcccgaagg ctacgtccag gagcgcacca tcttcttcaa ggacgacggc    1800
aactacaaga cccgcgccga ggtgaagttc gagggcgaca ccctggtgaa ccgcatcgag    1860
ctgaagggca tcgacttcaa ggaggacggc aacatcctgg ggcacaagct ggagtacaac    1920
tacaacagcc acaacgtcta tatcatggcc gacaagcaga agaacggcat caaggtgaac    1980
ttcaagatcc gccacaacat cgaggacggc agcgtgcagc tcgccgacca ctaccagcag    2040 aacacccca tcggcgacgg ccccgtgctg ctgcccgaca accactacct gagcacccag     2100
tccgccctga gcaaagaccc caacgagaag cgcgatcaca tggtcctgct ggagttcgtg    2160
accgccgccg ggatcactct cggcatggac gagctgtaca agtaagaatt ccgatcatat    2220
tcaataaccc ttaatataac ttcgtataat gtatgctata cgaagttatt aggtctgaag    2280
aggagtttac gtccagccaa gcttaggatc tcgacctcga aattctaccg ggtaggggag    2340
gcgcttttcc caaggcagtc tggagcatgc gctttagcag ccccgctggg cacttggcgc    2400
tacacaagtg gcctctggcc tcgcacacat tccacatcca ccggtaggcg ccaaccggct    2460
ccgttctttg gtggcccctt cgcgccacct tctactcctc ccctagtcag gaagttcccc    2520
cccgccccgc agctcgcgtc gtgcaggacg tgacaaatgg aagtagcacg tctcactagt    2580
ctcgtgcaga tggacagcac cgctgagcaa tggaagcggg taggcctttg gggcagcggc    2640
caatagcagc tttgctcctt cgctttctgg gctcagaggc tgggaagggg tgggtccggg    2700
ggcgggctca ggggcgggct caggggcggg gcgggcgccc gaaggtcctc cggaggcccg    2760
gcattctgca cgcttcaaaa gcgcacgtct ccgcgctgt tctcctcttc ctcatctccg     2820
ggcctttcga cctgcatcca tctagatctc gagcagctga agcttaccat gaccgagtac    2880
aagcccacgg tgcgcctcgc caccegcgac gacgtcccca gggccgtacg caccctcgcc    2940
gccgcgttcg ccgactaccc cgccacgcgc cacaccgtcg atccggaccg ccacatcgag    3000
cgggtcaccg agctgcaaga actcttcctc acgcgcgtcg ggctcgacat cggcaaggtg    3060
tgggtcgcgg acgacggcgc cgcggtggcg gtctggacca cgccggagag cgtcgaagcg    3120
ggggcggtgt cgccgagat cggcccgcgc atggccgagt tgagcggttc ccggctggcc    3180
gcgcagcaac agatggaagg cctcctgcg ccgcaccgge ccaaggagcc cgcgtggttc     3240
ctggccaccg tcggcgtctc gcccgaccac cagggcaagg gtctgggcag cgccgtcgtg    3300
ctccccggag tggaggcggc cgagcgcgcc ggggtgcccg ccttcctgga gacctccgcg    3360
ccccgcaacc tccccttcta cgagcggctc ggcttcaccg tcaccgccga cgtcgaggtg    3420
```

```
cccgaaggac cgcgcacctg gtgcatgacc cgcaagcccg gtgcctgacg cccgcccac    3480 gacccgcagc gcccgaccga aaggagcgca cgaccccatg catcgatgat atcagatccc    3540
cgggatgcag aaattgatga tctattaaac aataaagatg tccactaaaa tggaagtttt    3600
tcctgtcata ctttgttaag aagggtgaga acagagtacc tacattttga atggaaggat    3660
tggagctacg ggggtggggg tggggtggga ttagataaat gcctgctctt tactgaaggc    3720
tctttactat tgctttatga taatgtttca tagttggata tcataattta aacaagcaaa    3780
accaaattaa gggccagctc attcctccca ctcatgatct atagatctat agatctctcg    3840
tgggatcatt gttttctct tgattccac tttgtggttc taagtactgt ggtttccaaa    3900
tgtgtcagtt tcatagcctg aagaacgaga tcagcagcct ctgttccaca tacacttcat    3960
tctcagtatt gttttgccaa gttctaattc catcagaagc tggtcgagat ccggaaccct    4020
taatataact tcgtataatg tatgctatac gaagttatta ggtccctcga agaggttcac    4080
taggcgcgcc gaaggtgaca gaagcctgaa aactgagaca gaaacaaaac tgcccttttcc   4140 cagtgcgcgg gaagccccgc ggttaaagat ccccgcaccc tttaattttt gctctgcgat    4200
ggtcgttgtt tagcaacgac ttggcttcag atggcagcta catttgatgg tttgcaaatg    4260
ccgccgctgt tccaaacttc ctacggtcca tattgtttga tgaaaacttt ctgttaaaat    4320
tgtgtccttt ccgcccacct tctgctcccc ctttagatag atacggtata attgtaggta    4380
cccgtatatg gcatcattat tctagttccc tgctgccaat acgctgctaa aacgtcgcat    4440
cttctctgtc actggtttgg gtttaattta ttttacgccc tgggcatcca tccttgtgtg    4500
ttgcgcactc aagtgtggga gatttagtct tccgaagttg ttttccaaaa tgcacaatga    4560
aacgcaaaat tagtgcttcc aaagtggata acttttgact atggaattgt tagaaaacaa    4620
gaaactttaa ggtttatata ttgtataaac atacccagta tgtgcatccg atcgcgagaa    4680
cgttggcgtc ttttaggaaa ctccgcgcac gcactttatc agccgctgct gcggtggtgg    4740
ctccaggaga aactcaactg ccaattgcag accagttttt tttttttaa acacagccac    4800 ttataattct taagctcttt gcaaatgttt gtttaaaaaa tgaaaaatta aaaaaaatct    4860
agtagtgtca aacgcatttg gtcaattta ttttgctttg ttaatattag aaaacttatt    4920
tattattgtt tgctaccatt tctacttatc ttgattcatt ttttacgttt tctactcgag    4980
atcattttat tttaatttag caaagccaac tgcccttgtt taatgtattt tgttttgcaa    5040
atgattaaaa taaatgtgaa aagaagcctt ttgtcactta ttccttgagt tctagagtcg    5100
acctgcaggc atgcaagctt ggcgtaatca tggtcatagc tgtttcctgt gtgaaattgt    5160
tatccgctca caattccaca acaacatacga gccggaagca taaagtgtaa agcctggggt    5220
gcctaatgag tgagctaact cacattaatt gcgttgcgct cactgcccgc tttccagtcg    5280
ggaaacctgt cgtgccagct gcattaatga atcggccaac gcgcggggag aggcggtttg    5340
cgtattgggc gctcttccgc ttcctcgctc actgactcgc tgcgctcggt cgttcggctg    5400
cggcgagcgg tatcagctca ctcaaaggcg gtaatacggt tatccacaga atcagggat    5460 aacgcaggaa agaacatgtg agcaaaaggc cagcaaaagg ccaggaaccg taaaaaggcc    5520
gcgttgctgg cgttttttcca taggctccgc ccccctgacg agcatcacaa aaatcgacgc    5580
tcaagtcaga ggtggcgaaa cccgacagga ctataaagat accaggcgtt ccccctgga    5640 agctccctcg tgcgctctcc tgttccgacc ctgccgctta ccggatacct gtccgccttt    5700
ctcccttcgg gaagcgtggc gctttctcat agctcacgct gtaggtatct cagttcggtg    5760
taggtcgttc gctccaagct gggctgtgtg cacgaaccccc ccgttcagcc cgaccgctgc    5820
```

```
gccttatccg gtaactatcg tcttgagtcc aacccggtaa gacacgactt atcgccactg   5880
gcagcagcca ctggtaacag gattagcaga gcgaggtatg taggcggtgc tacagagttc   5940
ttgaagtggt ggcctaacta cggctacact agaagaacag tatttggtat ctgcgctctg   6000
ctgaagccaa ttaccttcgg aaaaagagtt ggtagctctt gatccggcaa acaaaccacc   6060
gctggtagcg gtggtttttt tgtttgcaag cagcagatta cgcgcagaaa aaaggatct    6120 caagaagatc ctttgatctt ttctacgggg tctgacgctc agtggaacga aaactcacgt   6180
taagggattt tggtcatgag attatcaaaa aggatcttca cctagatcct tttaaattaa   6240
aaatgaagtt ttaaatcaat ctaaagtata tatgagtaaa cttggtctga cagttaccaa   6300
tgcttaatca gtgaggcacc tatctcagcg atctgtctat ttcgttcatc catagttgcc   6360
tgactccccg tcgtgtagat aactacgata cgggagggct taccatctgg ccccagtgct   6420
gcaatgatac cgcgagaccc acgctcaccg gctccagatt tatcagcaat aaaccagcca   6480
gccggaaggg ccgagcgcag aagtggtcct gcaactttat ccgcctccat ccagtctatt   6540
aattgttgcc gggaagctag agtaagtagt tcgccagtta atagtttgcg caacgttgtt   6600
gccattgcta caggcatcgt ggtgtcacgc tcgtcgtttg gtatggcttc attcagctcc   6660
ggttcccaac gatcaaggcg agttacatga tcccccatgt tgtgcaaaaa agcggttagc   6720
tccttcggtc ctccgatcgt tgtcagaagt aagttggccg cagtgttatc actcatggtt   6780
atggcagcac tgcataattc tcttactgtc atgccatccg taagatgctt ttctgtgact   6840
ggtgagtact caaccaagtc attctgagaa tagtgtatgc ggcgaccgag ttgctcttgc   6900
ccggcgtcaa tacgggataa taccgcgcca catagcagaa ctttaaaagt gctcatcatt   6960
ggaaaacgtt cttcggggcg aaaactctca aggatcttac cgctgttgag atccagttcg   7020
atgtaaccca ctcgtgcacc caactgatct tcagcatctt ttactttcac cagcgtttct   7080
gggtgagcaa aaacaggaag gcaaaatgcc gcaaaaaagg gaataagggc gacacggaaa   7140
tgttgaatac tcatactctt cctttttcaa tattattgaa gcatttatca gggttattgt   7200
ctcatgagcg gatacatatt tgaatgtatt tagaaaaata aacaaatagg ggttccgcgc   7260
acatttcccc gaaaagtgcc acctgacgtc taagaaacca ttattatcat gacattaacc   7320
tataaaaata ggcgtatcac gaggcccttt cgtc                              7354
```

<210> SEQ ID NO 22
<211> LENGTH: 3496
<212> TYPE: DNA
<213> ORGANISM: Artificial Sequence
<220> FEATURE:
<223> OTHER INFORMATION: synthetic

<400> SEQUENCE: 22

```
ctttgattgg ctgctcgcac gcgcctgccc gcgccctcca ttggctgaga agacacgcga     60
ccggcgcgag gaggggttg ggagaggagc gggggagac tgagtggcgc gtgccgcttt    120 ttaaagggc gcagcgcctt cagcaaccgg agaagcatag ttgcacgcga cctggtgtgt    180
gatctccgag tgggtggggg agggtcgagg agggaaaaaa aaataagacg ttgcagaaga    240
gacccggaaa gggccttttt tttggttgag ctggtgtccc agtgctgcct ccgatcctga    300
gcctccgagc ctttgcagtg caatgtcccg cctgctgcat gcagaagagt gggctgaagt    360
gaaggagttg ggagaccacc atcgccagcc cagccgcat catctcccgc aaccgccgcc    420
gccgccgcag ccacctgcaa ctttgcaggc gagagagcat cccgtctacc cgcctgagct    480
```

```
gtccctcctg  acagcaccg  acccacgcgc  ctggctggct  cccactttgc  agggcatctg   540
cacggcacgc  gccgcccagt  atttgctaca  ttccccggag  ctgggtgcct  cagaggccgc   600
tgcgccccgg  gacgaggtgg  acggccgggg  ggagctggta  aggaggagca  gcggcggtgc   660
cagcagcagc  aagagccccg  ggccggtgaa  agtgcgggaa  cagctgtgca  agctgaaagg   720
cggggtggtg  gtagacgagc  tgggctgcag  ccgccaacgg  gccccttcca  gcaaacaggt   780
gaatggggtg  cagaagcaga  gacggctagc  agccaacgcc  agggagcggc  gcaggatgca   840
tgggctgaac  cacgccttcg  accagctgcg  caatgttatc  ccgtcgttca  acaacgacaa   900
gaagctgtcc  aaatatgaga  ccctgcagat  ggcccaaatc  tacatcaacg  ccttgtccga   960
gctgctacaa  acgccagcg   agggggaaca  gccaccgccg  cctccagcct  cctgcaaaag  1020
cgaccaccac  caccttcgca  ccgcggcctc  ctatgaaggg  ggcgcgggca  acgcgaccgc  1080
agctggggct  cagcaggctt  ccggagggag  ccagcggccg  accccgcccg  ggagttgccg  1140
gactcgcttc  tcagcccag   cttctgcggg  agggtactcg  gtgcagctgg  acgtctctgca 1200 cttctcgact  ttcgaggaca  cgccctgac   agcgatgatg  cgcaaaaga   atttgtctcc  1260 ttctctcccc  gggagcatct  tgcagccagt  gcaggaggaa  aacagcaaaa  cttcgcctcg  1320
gtcccacaga  agcgacgggg  aattttcccc  ccattcccat  acagtgact   cggatgaggc  1380 aagtgctagc  gccactaact  tctccctgtt  gaaacaagca  ggggatgtcg  aagagaatcc  1440
cgggccaatg  tgtgagcaagg  gcgaggagct  gttcaccggg  gtggtgccca  tcctggtcga  1500
gctggacggc  gacgtaaacg  gccacaagtt  cagcgtgtcc  ggcgagggcg  agggcgatgc  1560
cacctacggc  aagctgaccc  tgaagttcat  ctgcaccacc  ggcaagctgc  ccgtgccctg  1620
gcccaccctc  gtgaccaccc  tgacctacgg  cgtgcagtgc  ttcagccgct  accccgacca  1680
catgaagcag  cacgacttct  tcaagtccgc  catgcccgaa  ggctacgtcc  aggagcgcac  1740
catcttcttc  aaggacgacg  gcaactacaa  gacccgcgcc  gaggtgaagt  tcgagggcga  1800
caccctggtg  aaccgcatcg  agctgaaggg  catcgacttc  aaggaggacg  gcaacatcct  1860
ggggcacaag  ctggagtaca  actacaacag  ccacaacgtc  tatatcatgg  ccgacaagca  1920
gaagaacggc  atcaaggtga  acttcaagat  ccgccacaac  atcgaggacg  gcagcgtgca  1980
gctcgccgac  cactaccagc  agaacacccc  catcggcgac  ggccccgtgc  tgctgcccga  2040
caaccactac  ctgagcaccc  agtccgccct  gagcaaagac  cccaacgaga  gcgcgatca   2100 catggtcctg  ctggagttcg  tgaccgccgc  cgggatcact  ctcggcatgg  acgagctgta  2160
caagtaagaa  ttccgatcat  attcaataac  ccttaatata  acttcgtata  atgtatgcta  2220
tacgaagtta  ttaggtccct  cgaagaggtt  cactaggcgc  gccgaaggtg  acagaagcct  2280
gaaaactgag  acagaaacaa  aactgcccct  tcccagtgcg  cgggaagccc  cgcggttaaa  2340
gatccccgca  cccttaatt   tttgctctgc  gatggtcgtt  gtttagcaac  gacttggctt  2400
cagatggcag  ctacatttga  tggttttgcaa  atgccgccgc  tgttccaaac  ttcctacggt  2460
ccatattgtt  tgatgaaaac  tttctgttaa  aattgtgtcc  tttccgccca  ccttctgctc  2520
cccctttaga  tagatacggt  ataattgtag  gtacccgtat  atggcatcat  tattctagtt  2580
ccctgctgcc  aatacgctgc  taaaacgtcg  catcttctct  gtcactggtt  tgggtttaat  2640
ttattttacg  ccctgggcat  ccatccttgt  gtgttgcgca  ctcaagtgtg  ggagatttag  2700
tcttccgaag  ttgttttcca  aaatgcacaa  tgaaacgcaa  aattagtgct  tccaaagtgg  2760
ataacttttg  actatggaat  tgttagaaaa  caagaaactt  taaggtttat  atattgtata  2820 aacatacccca  gtatgtgcat  ccgatcgcga  gaacgttggc  gtctttagg   aaactccgcg  2880
```

```
cacgcacttt atcagccgct gctgcggtgg tggctccagg agaaactcaa ctgccaattg    2940
cagaccagtt ttttttttt taaacacagc cacttataat tcttaagctc tttgcaaatg    3000
tttgtttaaa aaatgaaaaa ttaaaaaaaa tctagtagtg tcaaacgcat ttggtcaatt    3060
ttattttgct ttgttaatat tagaaaactt atttattatt gtttgctacc atttctactt    3120
atcttgattc atttttacg ttttctactc gagatcattt tattttaatt tagcaaagcc    3180
aactgccctt gtttaatgta tttgttttg caaatgatta aaataaatgt gaaaagaagc    3240
cttttgtcac ttattccttg agtataacta ctgaaaacaa ttttcaaatg aatgactttg    3300
aagaattgag ttaagtcttc tattcaatgt catttatgcg atcttacagt tttgaagaaa    3360
aatgttgtaa acttggtgcc ttcaggtagt atcaaaaccc cttcaaagaa aagcactcaa    3420
gtcaataatt aaattgtgag ataaaacttc ttccaaattt gcagcacagt tttgcctctt    3480
tgatggccag gatctt                                                    3496
```